United States Patent
Goldby et al.

(10) Patent No.: US 10,562,882 B2
(45) Date of Patent: Feb. 18, 2020

(54) PIPERIDINE DERIVATIVES FOR USE IN THE TREATMENT OR PREVENTION OF PSYCHIATRIC AND NEUROLOGICAL CONDITIONS

(71) Applicant: Takeda Pharmaceutical Company Limited, Osaka (JP)

(72) Inventors: Anne Goldby, Cambridge (GB); Kerry Jenkins, Cambridge (GB); Martin Teall, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 43 days.

(21) Appl. No.: 15/039,650

(22) PCT Filed: Nov. 26, 2014

(86) PCT No.: PCT/GB2014/053499
§ 371 (c)(1),
(2) Date: May 26, 2016

(87) PCT Pub. No.: WO2015/079224
PCT Pub. Date: Jun. 4, 2015

(65) Prior Publication Data
US 2017/0166553 A1    Jun. 15, 2017

(30) Foreign Application Priority Data
Nov. 27, 2013  (GB) .................................. 1320905.1

(51) Int. Cl.
C07D 401/14    (2006.01)
C07D 401/04    (2006.01)

(52) U.S. Cl.
CPC ......... C07D 401/14 (2013.01); C07D 401/04 (2013.01)

(58) Field of Classification Search
CPC .................................................. C07D 401/14
See application file for complete search history.

(56) References Cited

U.S. PATENT DOCUMENTS

2008/0009514 A1    1/2008  Stoit et al.

FOREIGN PATENT DOCUMENTS

| CN | 101484454 A | 7/2009 |
|---|---|---|
| EP | 1302463 A1 | 4/2003 |
| EP | 1657240 A1 | 5/2006 |
| JP | 2009-522283 | 11/2009 |
| WO | 96/006098 A1 | 2/1996 |
| WO | 97/23466 A1 | 7/1997 |
| WO | 97/030998 A1 | 8/1997 |
| WO | 99/003859 A1 | 1/1999 |
| WO | 99/05134 A1 | 2/1999 |
| WO | 00/042044 A1 | 7/2000 |
| WO | 01/029034 A1 | 4/2001 |
| WO | 01/36417 A1 | 5/2001 |
| WO | 01/60821 A1 | 8/2001 |
| WO | 02/08212 A1 | 1/2002 |
| WO | 02/094794 A1 | 11/2002 |
| WO | 02/096912 A1 | 12/2002 |
| WO | 03/087102 A1 | 10/2003 |
| WO | 03/087103 A1 | 10/2003 |
| WO | 03/087104 A1 | 10/2003 |
| WO | 2004/016616 A1 | 2/2004 |
| WO | 2004/016617 A1 | 2/2004 |
| WO | WO 2004/019947 A1 | 3/2004 |
| WO | 2004043929 A1 | 5/2004 |
| WO | 2005100349 A2 | 10/2005 |
| WO | 2005100349 A3 | 10/2005 |
| WO | 2008015271 A1 | 2/2007 |
| WO | 2007062120 | 5/2007 |
| WO | 2007079163 A2 | 7/2007 |
| WO | 2007079163 A3 | 7/2007 |
| WO | 2007079214 A2 | 7/2007 |
| WO | 2007079214 A3 | 7/2007 |
| WO | 2008015271 A2 | 2/2008 |
| WO | 2010077976 A2 | 7/2010 |
| WO | 2010077976 A3 | 7/2010 |
| WO | 2013/179024 | 12/2013 |
| WO | WO-2015082499 A2 * | 6/2015 ........... A61K 31/404 |

OTHER PUBLICATIONS

American Chemical Society. STN Database. (C) Sep. 20, 2013. RN 1452884-03-5.*
Healthline.com. "Inflammatory Bowel Disease." © 2018. Available from: <https://www.healthline.com/health/inflammatory-bowel-disease>.*
WebMD. "Irritable bowel syndrome." © 2018. Available from: <https://www.webmd.com/ibs/tc/irritable-bowel-syndrome-ibs-prevention>.*
Schizophrenia.com. "Preventing Schizophrenia—Tactics and Risk Reduction". © 2018. Available from: <http://schizophrenia.com/prev1.htm>.*
NHS Choices. "Dementia guide." © 2018. Available from: <https://www.nhs.uk/conditions/dementia/dementia-prevention/>.*
Augusta Health. "Pain Prevention." © 2018. Available from: <https://www.augustahealth.com/pain-management-clinic/pain-prevention>.*

(Continued)

Primary Examiner — Andrew D Kosar
Assistant Examiner — John S Kenyon
(74) Attorney, Agent, or Firm — Barnes & Thornburg LLP; Scott Rothenberger

(57) ABSTRACT

The present invention provides compounds of formula (I) and pharmaceutically acceptable salts thereof, in which $R^1$, $R^2$, $R^3$, $R^4$ and $R^5$ are as defined in the specification, processes for their preparation, pharmaceutical compositions containing them and their use in therapy.

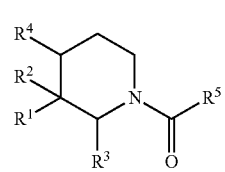

(I)

16 Claims, No Drawings

(56) References Cited

OTHER PUBLICATIONS

"Cognigram Detects Cognitive Impairment in Schizophrenia Patients." (c) Apr. 10, 2014. Available from: <https://www.cogstate.com/cognigram-detects-cognitive-impairment-schizophrenia-patients/>.*
Interntional Search Report and Written Opinion, International Application No. PCT/GB2014/053499, dated Jan. 13, 2015, 14 pages.
Cho et al., "Conformational Refinement of Hydroxamate-Based Histone Deacetylase Inhibitors and Exploration of 3-Piperidin-3-ylindole Analogues of Dacinostat (LAQ824)", J. Met Chem., Jan. 1, 2010, vol. 53, No. 7, 2952-2963.
Julia et al., "Recherches en série indolique.—Sur quelques acides (indolyl-3')-2 glutariques, les glutarimides et pipéridines correspondants", Bulletin de la Société Chimique de France, Société Française de Chimie. Paris, France, Jan. 1, 1964, pp. 1939-1945.
Kovalskiy et al., "Synthesis of 3-(3-Piperidyl)-Isoquinoline and 3-(4-Piperidyl)-Isoquinoline", Chemistry of Heterocyclic Compounds, vol. 45, No. 8, Nov. 20, 2009, pp. 957-964.
Stoit et al., "7-Azaindole derivatives as potential partial nicotinic agonists", Bioorganic & Medicinal Chemistry Letters, Jergamon, Amsterdam, NL, vol. 18, No. 1, Nov. 1, 2007, pp. 188-193.
Trujillo et al., "Novel tetrahydro-beta-carboline-1-caroxylic acids as inhibitors of mitogen activated protein in kinase-activated protein kinase 2 (MK-2)", Bioorganic & Medicinal Chemistry Letters, Pergamon, Amsterdam, NL, vol. 17, No. 16, Jul. 17, 2007, pp. 4657-4663.
Wang et al., "Synthesis and evaluation of 3-aryl piperidine analogs as potent and efficacious dopamine D4 receptor agonists", Bioorganic & Medicinal Chemistry Letters, Pergamon, Amsterdam, GB, vol. 13, No. 15, May 17, 2005, pp. 4667-4678.
Database registry [Online] Chemical Abstracts Service, Columbus, OH, US; Sep. 20, 2013, XP00273405, Database accession No. 1452884-03-5, m1452884-03-5, 1 page.
Database registry [Online] Chemical Abstracts Service, Columbus, OH, US; Sep. 22, 2013, XP002734306, Database accession No. 1452939-05-7, m 1452939-05-7, 1 page.
Database registry [Online] Chemical Abstracts Service, Columbus, OH, US; Sep. 22, 2013, XP002734307, Database accession No. 1452992-07-2, m 1452992-07-2, 1 page.
Database registry [Online] Chemical Abstracts Service, Columbus, OH, US; Sep. 22, 2013, XP002734308, Database accession No. 1453017-19-0, m 1453017-19-0, 1 page.
Miyaura, Norio; Yamada, Kinji ; Suzuki, Akira (1979). "A new stereospecific cross-coupling by the palladium-catalyzed reaction of 1-alkenylboranes with 1-alkenyl or 1-alkynyl halides". Tetrahedron Letters 20 (36): 3437-3440.
Miyaura, Norio; Suzuki, Akira (1995). "Palladium-Catalyzed Cross-Coupling Reactions of Organoboron Compounds". Chemical Reviews 95 (7): 2457-2483.
International Preliminary Report on Patentability, International Application No. PCT/GB2014/053499, dated May 31, 2016, 8 pages.
Search Report issued by UK Patent Office, Application No. GB1320905.1, dated May 21, 2014, 2 pages.
CHEMCATS Accession No. 0147885178, Aurora Screening Library, publication date Jul. 3, 2013; CAS Registry No. 1428016-79-8.
CHEMCATS Accession No. 0132108939, Aurora Screening Library, publication date Jul. 3, 2013; CAS Registry No. 1380857-90-8.
CHEMCATS Accession No. 0132108938, Aurora Screening Library, publication date Jul. 3, 2013; CAS Registry No. 1380854-82-9.
CHEMCATS Accession No. 0132118837, Aurora Screening Library, publication date Jul. 3, 2013; CAS Registry No. 1381044-09-2.
Miyaura et al., "Stereroselective Synthesis of Arylated (E)-Alkenes by the Reaction of Alk-1-enylboranes with Aryl Halides in the Presence of Palladium Catalyst", J.C.S. Chem. Comm. Jan. 1, 1979, pp. 866-867.
Olofson et al., "A New Reagent for the Selective, High-Yield N-Dealkylation of Tertiary Amines: Improved Syntheses of Naltrexone and Nalbuphine", J. Org. Chem., vol. 49, No. 11, 1984, pp. 2081-2082.

Lorenz et al., "A Novel Class of Tunable Zinc Reagents (RXZnCHY2Y) for Efficient Cyclopropanation of Olefins", J. Org. Chem. 2004, 69, pp. 327-334.
Wang, et al., Synthesis and evaluation of 3-aryl piperidine analogs as potent and efficacious dopamine D4 receptor agonists, Bioorganic & Medicinal Chemistry vol. 13, 15 (2005) 4667-4678.
Chemical Abstracts Registry No. 1394453-66-7, Entered STN: Sep. 18, 2012, (2-amino-4-pyridinyl) [3-(7-methyl-1H-benzimidazol-2-yl)-1-piperidinyl].
Chemical Abstracts Registry No. 1394435-52-9, Entered STN: Sep. 18, 2012, [2-(methylamino)-4-pyridinyl] [3-(7-methyl-1H-benzimidazol-2-yl)-1-piperidinyl].
Chemical Abstracts Registry No. 1381674-37-8, Entered STN: Jul. 5, 2012, [3-[3-[(1,1-dimethylethyl)amino] imidazo[1,2-a]pyridin-2-yl]-1-piperidinyl] (3-methyl-4-pyridinyl).
Chemical Abstracts Registry No. 1381666-19-8, Entered STN: Jul. 5, 2012, [3-[3-[(1,1-dimethylethypamino]imidazo[1,2-a]pyridin-2-yl]-1-piperidinyl](2-methoxy-4-pyridinyl).
Chemical Abstracts Registry No. 1214443-17-0, Entered STN: Mar. 25, 2010 [2-(methylamino)-4-pyridinyl] [3-[1-(1- methylethyl)-1H-benzimidazol-2-yl]-1-piperidinyl].
CAS Registry No. 1380854-82-9; Entered STN: Jul. 3, 2012; Methanone [3[6-(methylamino)-2-pyridinyl]-1-piperidinyl] (1-methyl-1H-pyrazol-4-yl).
CAS Registry No. 1422901-07-2; Entered STN: Mar. 11, 2013; Methanone, [3-(7-methyl-1H-benzimidazol-2-yl)-1-piperidinyl] (5-methyl-1-propyl-1H-pyrazol-4-yl).
CAS Registry No. 1422672-40-9; Entered STN: Mar. 8, 2013; Methanone [3-(7-methyl-1H-benzimidazol-2-yl)-1-piperidinyl] (1-methyl-1H-pyrazol-4-yl).
CAS Registry No. 1413422-72-6; Entered STN: Dec. 10, 2012; Methanone, [3-(7-methyl-1H-benzimidazol-2-yl)-1-piperidinyl] [1-(1-methylethyl)-1H-pyrazol-4-yl).
CAS Registry No. 1381742-93-3; Entered STN: Jul. 5, 2012; 3-Quinolinecarboxamide, 6-fluoro-2-[1-[(3-methyl-4-pyridinyl)carbonyl]-3-piperidinyl].
CAS Registry No. 1381742-46-6; Entered STN Jul. 5, 2012; 3-Quinolinecarboxamide, 6-fluoro-2-[1-[(2methoxy-4-pyridinyl)carbonyl]-3-piperidinyl].
CAS Registry No. 1381612-94-7; Entered STN Jul. 5, 2012; Methanone, [3-(3-amino-2-quinolinyl)-1-piperidinyl] (3-methyl-1-propyl-1H-pyrazol-4-yl).
CAS Registry No. 1381563-00-3; Entered STN: Jul. 5, 2012; 3-Quinolinecarboxamide, 2-[1-[(1,3-dimethyl-1H-pyrazol-4-yl)carbonyl)-3-piperidinyl]-6-fluoro.
CAS Registry No. 1381470-79-6; Entered STN: Jul. 4, 2012; 3-Quinolinecarboxamide, 2-[1-[(1, 5-dimethyl-1H-pyrazol-4-yl)carbonyl]-3-piperidinyl]-6-fluoro.
CAS Registry No. 1381451-71-3; Entered STN: Jul. 4, 2012; 3-Quinolinecarboxamide, 6-fluoro-2-[1-[(3-methyl-1-propyl-1H-pyrazol-4-yl)carbonyl]-3-piperidinyl.
CAS Registry No. 1381392-46-6; Entered STN: Jul. 4, 2012; 3-Quinolinecarboxamide, 2-[1-[(1-methyl-1H-pyrazol-4-yl)carbonyl]-3-piperidinyl].
CAS Registry No. 1381358-00-4; Entered STN: Jul. 4, 2012; 3-Quinolinecarboxamide, 2-[1-[(3-methyl-4-pyridinyl)carbonyl]-3-piperidinyl].
CAS Registry No. 1381322-92-4; Entered STN: Jul. 4, 2012; 3-Quinolinecarboxamide, 2-[1-[1(2-methoxy-4-pyridinyl)carbonyl]-3-piperidinyl].
CAS Registry No. 1381261-76-2; Entered STN: Jul. 4, 2012; 3-Quinolinecarboxamide, 2-[1-[(3-methyl-1-propyl-1H-pyrazol-4-yl)carbonyl]-3-piperidinyl].
CAS Registry No. 1381067-93-1; Entered STN: Jul. 4, 2012; Methanone, (1-methyl-1H-pyrazol-4-yl) [3-(6-methyl-2-pyridinyl)-1-piperidinyl].
CAS Registry No. 1380978-21-1; Entered STN: Jul. 4, 2012; Methanone,[6-[1-(1,3-dimethyl-1-H-pyrazol-4-yl)carbonyl]3-piperidinyl]-3-pyridinyl]-1-pyrrolidinyl.
CAS Registry No. 1380951-87-0; Entered STN: Jul. 4, 2012; 2-Pyridinecarboxamide, 6-[1-[(1-methyl-1H-pyrazol-4-yl)carbonyl]-3-piperidinyl].
Chinese Search Report for Chinese Application No. 201480064719X.

(56) References Cited

OTHER PUBLICATIONS

CAS Registry No. 1381322-92-4; Entered STN; Jul. 4, 2012; 3-Quinolinecarboxamide, 2-[1-[(2-methoxy-4-pyridinyl)carbonyl]-3-piperidinyl].

* cited by examiner

PIPERIDINE DERIVATIVES FOR USE IN THE TREATMENT OR PREVENTION OF PSYCHIATRIC AND NEUROLOGICAL CONDITIONS

CROSS-REFERENCE TO RELATED APPLICATIONS

This application is a 35 U.S.C. § 371(b) National Stage Application of International Application No. PCT/GB2014/053499, filed Nov. 26, 2014, and published as WO2015079224 on Jun. 4, 2015, which claims priority from GB 1320905.1, filed Nov. 27, 2013, the contents of which are hereby incorporated in their entirety by reference.

The present invention relates to the use of piperidine derivatives in therapy, particularly for the treatment or prevention of psychiatric and neurological conditions.

Prokineticins are cysteine-rich regulatory peptides that are thought to exert signaling activity via two highly conserved G protein-coupled receptors (GPCR), the prokineticin receptor 1 (PKR1 or PROKR1) and the prokineticin receptor 2 (PKR2 or PROKR2), that belong to the 7-transmembrane domain, G protein-coupled receptor (GPCR) superfamily.

Prokineticin receptor 1 (also known as GPR73) shows 87% homology to Prokineticin Receptor 2 (also known as GPR73L1). Prokineticins (PK1 and PK2) contain 86 and 81 amino acids respectively, sharing 45% amino acid identity. Both prokineticins activate the two prokineticin receptors, PKR1 and PKR2, with similar potency.

PKR1 receptors couple to $G_q/G_{11}$ proteins leading to phospholipase C activation, inositol phosphate production and calcium mobilization. In addition, activation of the mitogen-activated protein kinase (MAPK) pathways has also been described.

PKR1 is broadly distributed throughout peripheral tissues including the intestinal tract, testis, uterus, lung, mouse dorsal root ganglia, macrophage, bone, heart, rectum, white adipose and peripheral blood leukocytes. In addition, the receptor is expressed in the brain particularly in olfactory regions as well as in dorsal root ganglion (DRG) neurons, mouse hippocampus, dentate gyms, cerebellar cortex, cerebral cortex, human hippocampus, amygdala, medulla oblongata and spinal cord.

Prokineticins were originally identified as potent agents mediating gut motility, but were later shown to promote angiogenesis in steroidogenic glands (e.g. adrenal gland), heart and reproductive systems. They also modulate neurogenesis, circadian rhythms, nociception, haematopoiesis as well as the immune response. Prokineticins are thought to be associated with pathologies of the reproductive and nervous systems, myocardial infarction and tumorigenesis.

Consequently, antagonisim of the functions of the prokineticins may have utility in the treatment of disorders or diseases including gastrointestinal motility, angiogenesis, hematopoiesis, diabetes (e.g. as described in International Patent Application Publication No. WO 2010/077976) and pain (e.g. as described in International Patent Application Publication No. WO 2007/079214).

Certain piperidine derivatives are known chemical library compounds with no known use that are available from commercial suppliers such as Chembridge Corporation, Asinex Limited or Aurora Fine Chemicals, in particular the following compounds having Chemical Abstracts Registry Nos. 1394453-66-7, 1394435-52-9, 1381674-37-8, 1381666-19-8, 1214443-17-0, 1428016-79-8, 1381044-09-2, 1380857-90-8 and 1380854-82-9. Other piperidine derivatives which are said to be effective as metabotropic glutamate receptor (mGluR) modulators are known from International Patent Application Publication No. WO 2008/015271.

We have now discovered a new class of compounds that are prokineticin receptor modulators which have desirable activity profiles. The compounds of this invention have beneficial potency, selectivity and/or pharmacokinetic properties.

In accordance with the present invention, there is therefore provided a compound of formula

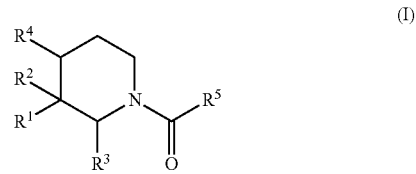

(I)

wherein $R^1$ represents a 6- to 10-membered heteroaromatic group containing from one to three ring heteroatoms selected from nitrogen atoms, the heteroaromatic group being substituted by at least one substituent selected from halogen, cyano, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylcarbonyl, $C_1$-$C_6$ alkylcarbonyloxy, $C_1$-$C_6$ alkoxycarbonyl, —$NR^6R^7$, —$CONR^8R^9$, $C_3$-$C_6$ cycloalkyl, $C_3$-$C_6$ cycloalkyloxy or $C_3$-$C_6$ cycloalkylmethyl;

either $R^2$ represents a hydrogen or fluorine atom or a hydroxyl or $C_1$-$C_3$ alkoxy group, $R^3$ represents a hydrogen atom and $R^4$ represents a hydrogen atom, or, when $R^4$ represents a hydrogen atom, $R^2$ may together with $R^3$ form a carbon-carbon single bond or $R^2$ and $R^3$ may together with the carbon atoms to which they are attached form a cyclopropyl ring, or, when $R^3$ represents a hydrogen atom, $R^2$ may together with $R^4$ form a carbon-carbon single bond or $R^2$ and $R^4$ may together with the carbon atoms to which they are attached form a cyclopropyl ring;

$R^5$ represents a 5- to 6-membered heteroaromatic group containing from one to three ring heteroatoms selected from nitrogen atoms, the heteroaromatic group being substituted by at least one substituent selected from halogen, cyano, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylcarbonyl, $C_1$-$C_6$ alkylcarbonyloxy, $C_1$-$C_6$ alkoxycarbonyl, —$NR^{10}R^{11}$, —$CONR^{12}R^{13}$, $C_3$-$C_6$ cycloalkyl, $C_3$-$C_6$ cycloalkyloxy or $C_3$-$C_6$ cycloalkylmethyl;

$R^6$ and $R^7$ each independently represent a hydrogen atom or a $C_1$-$C_6$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent selected from fluorine, hydroxyl and $C_1$-$C_3$ alkoxy;

$R^8$ and $R^9$ each independently represent a hydrogen atom or a $C_1$-$C_6$ alkyl group, or $R^8$ and $R^9$ may together with the nitrogen atom to which they are attached form a 4- to 7-membered saturated heterocyclic ring;

$R^{10}$ and $R^{11}$ each independently represent a hydrogen atom or a hydroxyl, $C_1$-$C_6$ alkyl, $C_1$-$C_6$ haloalkyl, $C_1$-$C_6$ alkoxy or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent selected from fluorine, hydroxyl and $C_1$-$C_3$ alkoxy; and $R^{12}$ and $R^{13}$ each independently represent a hydrogen atom or a $C_1$-$C_6$ alkyl group, or $R^{12}$ and $R^{13}$ may together with the nitrogen atom to which they are attached form a 4- to 7-membered saturated heterocyclic ring;

provided that the compound of formula (I) is not:
(1) [4-[3-(7-methyl-1H-1,3-benzodiazol-2-yl)piperidine-1-carbonyl]pyridin-2-amine] (CAS No. 1394453-66-7),
(2) [N-methyl-4-[3-(7-methyl-1H-1,3-benzodiazol-2-yl)piperidine-1-carbonyl]pyridin-2-amine (CAS No. 1394435-52-9),
(3) [3-[3-[(1,1-dimethylethyl)amino)imidazo[1,2-a]pyridin-2-yl]-1-piperidinyl](3-methyl-4-pyridinyl)methanone (CAS No. 1381674-37-8),
(4) [3-[3-[(1,1-dimethylethyl)amino)imidazo[1,2-a]pyridin-2-yl]-1-piperidinyl](2-methoxy-4-pyridinyl)methanone (CAS No. 1381666-19-8),
(5) [2-(methylamino)-4-pyridinyl][3-[1-(1-methylethyl)-1H-benzimidazol-2-yl]-1-piperidinyl]methanone (CAS No. 1214443-17-0),
(6) (1,5-dimethyl-1H-pyrazol-4-yl)[3-(6-methyl-1H-benzimidazol-2-yl)-1-piperidinyl]methanone (CAS No. 1428016-79-8),
(7) 6-{1-[(1,3-dimethyl-1H-pyrazol-4-yl)carbonyl]-3-piperidinyl}-N,N-dimethylnicotinamide (CAS No. 1381044-09-2),
(8) (1-methyl-1H-pyrazol-4-yl)[3-(5-methyl-2-pyridinyl)-1-piperidinyl]methanone (CAS No. 1380857-90-8), or
(9) [3-[6-(methylamino)-2-pyridinyl]-1-piperidinyl](1-methyl-1H-pyrazol-4-yl)methanone (CAS No. 1380854-82-9);

or a pharmaceutically acceptable salt thereof.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl.

A $C_1$-$C_6$ hydroxyalkyl substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

The term "heteroaromatic" group, as it is used herein, refers to an aryl group in which from 1 to 3 ring carbon atoms are replaced by nitrogen atoms. The heteroaromatic group may be monocyclic or polycyclic (e.g. bicyclic) in which the two or more rings are fused. The heteroaromatic group can be bonded at any suitable ring atom (i.e. at any carbon or nitrogen atom of the heteroaromatic ring system). Examples of heteroaromatic groups include the following:

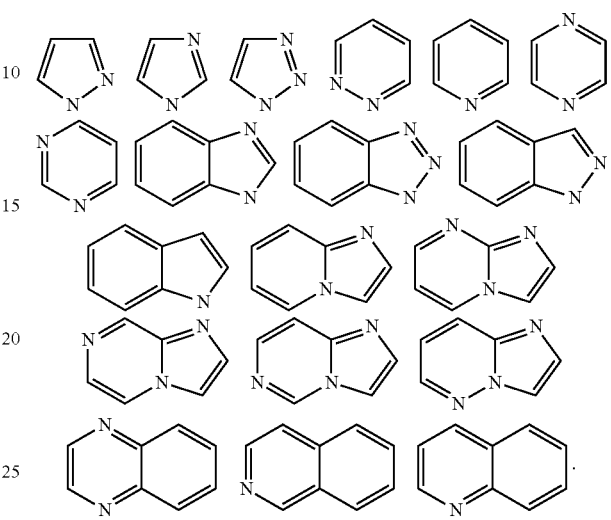

A $C_3$-$C_6$ cycloalkyl group or moiety in a substituent group represents a saturated monocyclic hydrocarbon ring structure containing from three to six carbon atoms.

A 4- to 7-membered saturated heterocyclic ring will contain at least one ring nitrogen atom and may contain one or more (e.g. one or two) further ring heteroatoms independently selected from nitrogen, oxygen and sulphur atoms. It will be understood that the definition is not intended to include unstable structures or any O—O, O—S or S—S bonds and that a substituent, if present, may be attached to any suitable ring atom. Examples of heterocyclic rings include azetidinyl, pyrrolidinyl, piperidinyl, morpholinyl, piperazinyl, 1,4-azathianyl, azepanyl and 1,4-oxaazepanyl.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents a 6-, 7- or 8- to 9- or 10-membered heteroaromatic group containing one, two or three ring heteroatoms selected from nitrogen atoms (e.g. pyridinyl, pyrazinyl, pyrimidinyl, pyridazinyl, triazinyl, benzodiazolyl, indolyl, quinolinyl and quinazolinyl), the heteroaromatic group being substituted by at least one substituent (e.g. one, two, three or four substituents independently) selected from halogen (e.g. fluorine, chlorine or bromine), cyano, $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —$NR^6R^7$, —$CONR^8R^9$, $C_3$-$C_6$ cycloalkyl, $C_3$-$C_6$ cycloalkyloxy or $C_3$-$C_6$ cycloalkylmethyl.

In an embodiment of the invention, $R^1$ represents a 6- to 7-, 8- or 9-membered heteroaromatic group containing one, two or three ring heteroatoms selected from nitrogen atoms, the heteroaromatic group being substituted by at least one substituent (e.g. one, two, three or four substituents independently) selected from halogen (e.g. fluorine, chlorine or bromine), cyano, $C_1$-$C_4$, or $C_1$-$C_3$, or $C_1$-$C_2$ alkyl, $C_2$-$C_4$ alkenyl, $C_2$-$C_4$ alkynyl, $C_1$-$C_2$ haloalkyl, $C_1$-$C_2$ hydroxyalkyl, $C_1$-$C_2$ alkoxy, $C_1$-$C_2$ haloalkoxy, $C_1$-$C_2$ alkylcarbonyl, $C_1$-$C_2$ alkylcarbonyloxy, $C_1$-$C_2$ alkoxycarbonyl, —$NR^6R^7$, —$CONR^8R^9$, $C_3$-$C_6$ or $C_3$-$C_5$ or $C_5$-$C_6$ cycloalkyl, $C_3$-$C_6$ or $C_3$-$C_5$ or $C_5$-$C_6$ cycloalkyloxy or $C_3$-$C_6$ or $C_3$-$C_5$ or $C_5$-$C_6$ cycloalkylmethyl.

In another embodiment of the invention, $R^1$ represents a 6- to 7-, 8- or 9-membered heteroaromatic group containing one or two ring heteroatoms selected from nitrogen atoms (such as pyridinyl, benzodiazolyl or indolyl), the heteroaromatic group being substituted by one or two substituents independently selected from halogen (e.g. fluorine, chlorine or bromine, particularly chlorine), $C_1$-$C_3$ alkyl (e.g. methyl, ethyl or isopropyl) and $C_1$-$C_2$ haloalkyl (e.g. trifluoromethyl).

In a preferred embodiment, $R^1$ represents any one of the following moieties or is selected from a group containing two or more of such moieties in any combination:
  (i) methyl-1,3-benzodiazolyl (e.g. 1-(methyl)-1,3-benzodiazol-2-yl),
  (ii) isopropyl-1,3-benzodiazolyl (e.g. 1-(isopropyl)-1,3-benzodiazol-2-yl),
  (iii) methyl-indolyl (e.g. 1-(methyl)-indol-2-yl),
  (iv) ethyl-indolyl (e.g. 1-(ethyl)-indol-2-yl),
  (v) isopropyl-indolyl (e.g. 1-(isopropyl)-indol-2-yl),
  (vi) di-alkyl substituted indolyl (e.g. (1-ethyl-5-methyl)-indol-2-yl or (1-ethyl-3-methyl)-indol-2-yl),
  (vii) (1-ethyl-5-chloro)-indol-2-yl,
  (viii) (3-methyl-5-chloro)-pyridin-2-yl, and
  (ix) (3-trifluoromethyl-5-chloro)-pyridin-2-yl.

In one embodiment of the invention, $R^2$ represents a hydrogen atom, $R^3$ represents a hydrogen atom and $R^4$ represents a hydrogen atom.

In another embodiment, $R^2$ represents a fluorine atom, $R^3$ represents a hydrogen atom and
$R^4$ represents a hydrogen atom.

In yet another embodiment, $R^2$ represents a hydroxyl group, $R^3$ represents a hydrogen atom and $R^4$ represents a hydrogen atom.

In a further embodiment, $R^2$ represents a $C_1$-$C_3$ alkoxy (particularly methoxy) group, $R^3$ represents a hydrogen atom and $R^4$ represents a hydrogen atom.

Alternatively, when $R^4$ represents a hydrogen atom, $R^2$ may together with $R^3$ form a carbon-carbon single bond, thereby resulting in the formation of a double bond between the carbon atoms to which $R^2$ and $R^3$ are attached, as illustrated below:

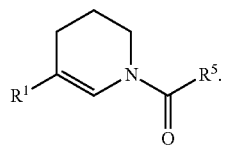

Similarly, when $R^3$ represents a hydrogen atom, $R^2$ may together with $R^4$ form a carbon-carbon single bond, thereby resulting in the formation of a double bond between the carbon atoms to which $R^2$ and $R^4$ are attached, as illustrated below:

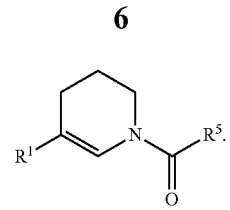

$R^5$ represents a 5- to 6-membered heteroaromatic group containing from one to three ring heteroatoms selected from nitrogen atoms, the heteroaromatic group being substituted by at least one substituent (e.g. one, two, three or four substituents independently) selected from halogen (e.g. fluorine, chlorine or bromine), cyano, $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —$NR^{10}R^{11}$, —$CONR^{12}R^{13}$, $C_3$-$C_6$ cycloalkyl, $C_3$-$C_6$ cycloalkyloxy or $C_3$-$C_6$ cycloalkylmethyl.

Examples of 5- to 6-membered heteroaromatic groups include pyrrolyl, imidazolyl, pyrazolyl, triazolyl, tetrazolyl, pyridinyl, pyrazinyl, pyrimidinyl, pyridazinyl and triazinyl. Preferred groups include pyridinyl, pyridazinyl and pyrazolyl, especially 4-pyridinyl, 4-pyridazinyl, 5-pyridazinyl and 4-pyrazolyl.

In one embodiment, $R^5$ represents a 5- and/or 6-membered heteroaromatic group containing one, two or three ring heteroatoms selected from nitrogen atoms, the heteroaromatic group being substituted by at least one substituent (e.g. one, two, three or four substituents independently) selected from halogen (e.g. fluorine, chlorine or bromine), cyano, $C_1$-$C_4$, or $C_1$-$C_3$, or $C_1$-$C_2$ alkyl, $C_1$-$C_2$ haloalkyl, $C_1$-$C_2$ hydroxyalkyl, $C_1$-$C_4$, or $C_1$-$C_3$, or $C_1$-$C_2$ alkoxy, $C_1$-$C_2$ haloalkoxy, $C_1$-$C_2$ alkylcarbonyl, $C_1$-$C_2$ alkylcarbonyloxy, $C_1$-$C_2$ alkoxycarbonyl, —$NR^{10}R^{11}$, —$CONR^{12}R^{13}$, $C_3$-$C_6$ or $C_3$-$C_5$ or $C_5$-$C_6$ cycloalkyl, $C_3$-$C_6$ or $C_3$-$C_5$ or $C_5$-$C_6$ cycloalkyloxy or $C_3$-$C_6$ or $C_3$-$C_5$ or $C_5$-$C_6$ cycloalkylmethyl.

In a further embodiment, $R^5$ represents a 5- and/or 6-membered heteroaromatic group containing one, two or three ring heteroatoms selected from nitrogen atoms, the heteroaromatic group being substituted by at least one substituent (e.g. one, two, three or four substituents independently) selected from halogen (e.g. fluorine, chlorine or bromine), $C_1$-$C_4$, or $C_1$-$C_3$, or $C_1$-$C_2$ alkyl, or —$NR^{10}R^{11}$.

In a still further embodiment, $R^5$ represents a 5- and/or 6-membered heteroaromatic group containing one or two ring heteroatoms selected from nitrogen atoms such as pyridinyl (particularly 4-pyridinyl), pyridazinyl (particularly 4-pyridazinyl or 5-pyridazinyl) or pyrazolyl (particularly 4-pyrazolyl), the heteroaromatic group being substituted by one or two substituents independently selected from halogen (particularly chlorine), $C_1$-$C_2$ alkyl, and —$NR^{10}R^{11}$.

In a preferred embodiment, $R^5$ represents any one of the following moieties or is selected from a group containing two or more of such moieties in any combination:
  (i) 2-(methylamino)-pyridin-4-yl,
  (ii) 2-(dimethylamino)-pyridin-4-yl,
  (iii) 6-chloro-pyridazin-4-yl,
  (iv) 3-(methylamino)-pyridazin-5-yl,
  (v) 3-(dimethylamino)pyridazin-5-yl,
  (vi) 1-(ethyl)-pyrazol-4-yl, and
  (vii) (1-methyl-3-amino)-pyrazol-4-yl.

$R^6$ and $R^7$ each independently represent a hydrogen atom or a $C_1$-$C_6$, or $C_1$-$C_4$, or $C_1$-$C_2$ alkyl or $C_3$-$C_6$ or $C_3$-$C_5$ or $C_5$-$C_6$ cycloalkyl group, or $R^6$ and $R^7$ may together with the nitrogen atom to which they are attached form a 4-, 5-, 6- or 7-membered saturated heterocyclic ring optionally substituted by at least one substituent (e.g. one or two substituents independently) selected from fluorine, hydroxyl and $C_1$-$C_3$ alkoxy.

In one aspect, the saturated heterocyclic ring may contain a single ring heteroatom (being the nitrogen atom to which $R^6$ and $R^7$ are attached). In an alternative aspect, the saturated heterocyclic ring may contain a second ring heteroatom selected from a nitrogen or oxygen atom.

In a first embodiment, $R^6$ and $R^7$ each independently represent a hydrogen atom or a $C_1$-$C_4$, or $C_1$-$C_3$, or $C_1$-$C_2$ alkyl or $C_3$-$C_6$, particularly cyclopropyl, group, or $R^6$ and $R^7$ may together with the nitrogen atom to which they are attached form a 4- or 5-membered saturated heterocyclic ring (azetidinyl or pyrrolidinyl) optionally substituted by one or two substituents independently selected from fluorine, hydroxyl and $C_1$-$C_3$ alkoxy.

In a second embodiment, $R^6$ and $R^7$ each represent a hydrogen atom.

In a third embodiment, $R^6$ and $R^7$ each represent a $C_1$-$C_3$ alkyl group.

In a fourth embodiment, one of $R^6$ and $R^7$ represents a hydrogen atom and the other of $R^6$ and $R^7$ represents a $C_1$-$C_3$ alkyl group.

In a fifth embodiment, one of $R^6$ and $R^7$ represents a cyclopropyl group and the other of $R^6$ and $R^7$ represents a $C_1$-$C_3$ alkyl group.

In a sixth embodiment, $R^6$ and $R^7$ together with the nitrogen atom to which they are attached form an azetidinyl or pyrrolidinyl ring optionally substituted by one or two substituents independently selected from fluorine and hydroxyl.

In a seventh embodiment, $R^6$ and $R^7$ together with the nitrogen atom to which they are attached form an unsubstituted azetidinyl or pyrrolidinyl ring.

$R^8$ and $R^9$ each independently represent a hydrogen atom or a $C_1$-$C_6$, or $C_1$-$C_4$, or $C_1$-$C_2$ alkyl group, or $R^8$ and $R^9$ may together with the nitrogen atom to which they are attached form a 4- to 7-membered saturated heterocyclic ring.

In an embodiment of the invention, $R^8$ and $R^9$ each independently represent a hydrogen atom or a methyl group.

$R^{10}$ and $R^{11}$ each independently represent a hydrogen atom or a hydroxyl, $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy or $C_3$-$C_6$ or $C_3$-$C_5$ or $C_5$-$C_6$ cycloalkyl group, or $R^{10}$ and $R^{11}$ may together with the nitrogen atom to which they are attached form a 4-, 5-, 6- or 7-membered saturated heterocyclic ring optionally substituted by at least one substituent (e.g. one or two substituents independently) selected from fluorine, hydroxyl and $C_1$-$C_3$ alkoxy.

In one aspect, the saturated heterocyclic ring may contain a single ring heteroatom (being the nitrogen atom to which $R^{10}$ and $R^{11}$ are attached). In an alternative aspect, the saturated heterocyclic ring may contain a second ring heteroatom selected from a nitrogen or oxygen atom.

In a first embodiment, $R^{10}$ and $R^{11}$ each independently represent a hydrogen atom or a hydroxyl, $C_1$-$C_4$, or $C_1$-$C_3$, or $C_1$-$C_2$ alkyl, $C_1$-$C_4$, or $C_1$-$C_3$, or $C_1$-$C_2$ haloalkyl, $C_1$-$C_4$, or $C_1$-$C_3$, or $C_1$-$C_2$ alkoxy or $C_3$-$C_6$, particularly cyclopropyl, group, or $R^{10}$ and $R^{11}$ may together with the nitrogen atom to which they are attached form a 4- or 5-membered saturated heterocyclic ring (azetidinyl or pyrrolidinyl) optionally substituted by one or two substituents independently selected from fluorine, hydroxyl and $C_1$-$C_3$ alkoxy.

In a second embodiment, $R^{10}$ and $R^{11}$ each represent a hydrogen atom.

In a third embodiment, $R^{10}$ and $R^{11}$ each represent a $C_1$-$C_3$ alkyl group.

In a fourth embodiment, one of $R^{10}$ and $R^{11}$ represents a hydrogen atom and the other of $R^{10}$ and $R^{11}$ represents a $C_1$-$C_3$ alkyl group.

In a fifth embodiment, one of $R^{10}$ and $R^{11}$ represents a cyclopropyl group and the other of $R^{10}$ and $R^{11}$ represents a $C_1$-$C_3$ alkyl group.

In a sixth embodiment, $R^{10}$ and $R^{11}$ together with the nitrogen atom to which they are attached form an azetidinyl or pyrrolidinyl ring optionally substituted by one or two substituents independently selected from fluorine and hydroxyl.

In a seventh embodiment, $R^{10}$ and $R^{11}$ together with the nitrogen atom to which they are attached form an unsubstituted azetidinyl or pyrrolidinyl ring.

In an eighth embodiment, one of $R^{10}$ and $R^{11}$ represents a hydrogen atom or a methyl group and the other of $R^{10}$ and $R^{11}$ represents a hydroxyl, methoxy or $C_1$-$C_2$ haloalkyl group.

$R^{12}$ and $R^{13}$ each independently represent a hydrogen atom or a $C_1$-$C_6$, or $C_1$-$C_4$, or $C_1$-$C_2$ alkyl group, or $R^{12}$ and $R^{13}$ may together with the nitrogen atom to which they are attached form a 4- to 7-membered saturated heterocyclic ring.

In an embodiment of the invention, $R^{12}$ and $R^{13}$ each independently represent a hydrogen atom or a methyl group.

Subject to the above provisos, preferred compounds of formula (I) are those in which:
  $R^1$ represents a 6- to 9-membered heteroaromatic group containing one or two ring heteroatoms selected from nitrogen atoms, the heteroaromatic group being substituted by one or two substituents independently selected from halogen, $C_1$-$C_3$ alkyl and $C_1$-$C_2$ haloalkyl;
  $R^2$ represents a hydrogen or fluorine atom or a methoxy group;
  $R^3$ represents a hydrogen atom;
  $R^4$ represents a hydrogen atom;
  $R^5$ represents a 5- to 6-membered heteroaromatic group containing one or two ring heteroatoms selected from nitrogen atoms, the heteroaromatic group being substituted by one or two substituents independently selected from halogen, $C_1$-$C_2$ alkyl and —$NR^{10}R^{11}$; and
  $R^{10}$ and $R^{11}$ each independently represent a hydrogen atom or a $C_1$-$C_6$ alkyl group.

Examples of preferred compounds of formula (I) according to the invention include:
  N,N-Dimethyl-4-{3-[1-(propan-2-yl)-1H-1,3-benzodiazol-2-yl]piperidin-1-carbonyl}pyridin-2-amine,
  N,N-Dimethyl-4-{3-[1-(propan-2-yl)-1H-1,3-benzodiazol-2-yl]piperidine-1-carbonyl}pyridin-2-amine (Enantiomer 1 substantially as hereinbefore described and with reference to Example 2),
  N,N-Dimethyl-4-{3-[1-(propan-2-yl)-1H-1,3-benzodiazol-2-yl]piperidine-1-carbonyl}pyridin-2-amine (Enantiomer 2 substantially as hereinbefore described and with reference to Example 3),
  N,N-Dimethyl-4-[3-(1-methyl-1H-1,3-benzodiazol-2-yl)piperidine-1-carbonyl]pyridin-2-amine,
  2-[1-(6-Chloropyridazine-4-carbonyl)piperidin-3-yl]-1-(propan-2-yl)-1H-1,3-benzodiazole,
  N-Methyl-5-{3-[1-(propan-2-yl)-1H-1,3-benzodiazol-2-yl]piperidine-1-carbonyl}pyridazin-3-amine, 2-[1-(1-Ethyl-1H-pyrazole-4-carbonyl)piperidin-3-yl]-1-(propan-2-yl)-1H-1,3-benzodiazole,
N,N-Dimethyl-4-[3-(1-methyl-1H-indol-2-yl)piperidine-1-carbonyl]pyridin-2-amine,
N-Methyl-5-[3-(1-methyl-1H-indol-2-yl)piperidine-1-carbonyl]pyridazin-3-amine,
4-[3-(1-Ethyl-1H-indol-2-yl)piperidine-1-carbonyl]-N,N-dimethylpyridin-2-amine,
5-[3-(1-Ethyl-1H-indol-2-yl)piperidine-1-carbonyl]-N,N-dimethylpyridazin-3-amine,
5-[3-(1-Ethyl-1H-indol-2-yl)piperidine-1-carbonyl]-N-methylpyridazin-3-amine,
N,N-Dimethyl-5-{3-[1-(propan-2-yl)-1H-indol-2-yl]piperidine-1-carbonyl}pyridazin-3-amine,
N-Methyl-5-{3-[1-(propan-2-yl)-1H-indol-2-yl]piperidine-1-carbonyl}pyridazin-3-amine,
2-{1-[(1-Ethyl-1H-pyrazol-4-yl)carbonyl]piperidin-3-yl}-1-(propan-2-yl)-1H-indole,
1-Methyl-4-{3-[1-(propan-2-yl)-1H-indol-2-yl]piperidine-carbonyl}-1H-pyrazol-3-amine,
1-Ethyl-2-{1-[(1-ethyl-1H-pyrazol-4-yl)carbonyl]piperidin-3-yl}-5-methyl-1H-indole,
5-[3-(1-Ethyl-3-methyl-1H-indol-2-yl)piperidine-1-carbonyl]-N-methylpyridazin-3-amine,
5-[3-(1-Ethyl-5-methyl-1H-indol-2-yl)piperidine-1-carbonyl]-N-methylpyridazin-3-amine,
5-[3-(5-Chloro-1-ethyl-1H-indol-2-yl)piperidine-1-carbonyl]-N-methylpyridazin-3-amine,
5-[3-(1-Ethyl-5-methyl-1H-indol-2-yl)piperidine-1-carbonyl]-N,N-dimethylpyridazin-3-amine,
5-[3-(5-Chloro-1-ethyl-1H-indol-2-yl)piperidine-1-carbonyl]-N,N-dimethylpyridazin-3-amine,
N-Methyl-5-[3-(3-methyl-1H-indol-2-yl)piperidine-1-carbonyl]pyridazin-3-amine,
N,N-Dimethyl-5-[3-(3-methyl-1H-indol-2-yl)piperidine-1-carbonyl]pyridazin-3-amine,
4-[3-(1-Ethyl-3-methyl-1H-indol-2-yl)piperidine-1-carbonyl]-1-methyl-1H-pyrazol-3-amine,
4-[3-(1-Ethyl-5-methyl-1H-indol-2-yl)piperidine-1-carbonyl]-1-methyl-1H-pyrazol-3-amine,
4-[3-(5-Chloro-1-ethyl-1H-indol-2-yl)piperidine-1-carbonyl]-1-methyl-1H-pyrazol-3-amine,
5-[3-(5-Chloro-3-methylpyridin-2-yl)piperidine-1-carbonyl]-N,N-dimethylpyridazin-3-amine,
4-{3-[5-Chloro-3-(trifluoromethyl)pyridin-2-yl]-3-methoxypiperidine-1-carbonyl}-N-methylpyridin-2-amine,
5-{3-[5-Chloro-3-(trifluoromethyl)pyridin-2-yl]-3-methoxypiperidin-1-yl}carbonyl)-N-methylpyridazin-3-amine,
5-{3-[5-Chloro-3-(trifluoromethyl)pyridin-2-yl]-3-methoxypiperidine-1-carbonyl}-N,N-dimethylpyridazin-3-amine,
5-Chloro-2-[1-(1-ethyl-1H-pyrazole-4-carbonyl)-3-methoxypiperidin-3-yl]-3-(trifluoromethyl)pyridine,
4-{3-[5-Chloro-3-(trifluoromethyl)pyridin-2-yl]-3-methoxypiperidine-1-carbonyl}-N,N-dimethylpyridin-2-amine,
4-[3-(5-Chloro-3-methylpyridin-2-yl)-3-methoxypiperidine-1-carbonyl]-N-methylpyridin-2-amine,
4-[3-(5-Chloro-3-methylpyridin-2-yl)-3-fluoropiperidine-1-carbonyl]-N-methylpyridin-2-amine,
5-[3-(5-Chloro-3-methylpyridin-2-yl)-3-methoxypiperidine-1-carbonyl]-N-methylpyridazin-3-amine,
5-[3-(5-Chloro-3-methylpyridin-2-yl)-3-methoxypiperidine-1-carbonyl]-N,N-dimethylpyridazin-3-amine,
5-[3-(5-Chloro-3-methylpyridin-2-yl)-3-fluoropiperidine-1-carbonyl]-N-methylpyridazin-3-amine,
5-[3-(5-Chloro-3-methylpyridin-2-yl)-3-fluoropiperidine-1-carbonyl]-N,N-dimethylpyridazin-3-amine,
5-Chloro-2-[1-(1-ethyl-1H-pyrazole-4-carbonyl)-3-methoxypiperidin-3-yl]-3-methylpyridine,
5-Chloro-2-[1-(1-ethyl-1H-pyrazole-4-carbonyl)-3-fluoropiperidin-3-yl]-3-methylpyridine,
4-[3-(5-Chloro-3-methylpyridin-2-yl)-3-methoxypiperidine-1-carbonyl]-1-methyl-1H-pyrazol-3-amine,
4-[3-(5-Chloro-3-methylpyridin-2-yl)-3-fluoropiperidine-1-carbonyl]-1-methyl-1H-pyrazol-3-amine,
and pharmaceutically acceptable salts of any one thereof.

It should be noted that each of the chemical compounds listed above represents a particular and independent aspect of the invention.

Compounds of formula (I) and pharmaceutically acceptable salts thereof as defined above may be prepared by a process comprising reacting a compound of formula

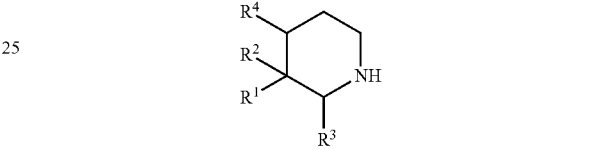

wherein $R^1$, $R^2$, $R^3$ and $R^4$ are as defined in formula (I) or a salt thereof (e.g. a hydrochloride salt), with a compound of formula

wherein $R^5$ is as defined in formula (I);

and optionally thereafter carrying out one or more of the following procedures:
removing any protecting groups
converting a compound of formula (I) into another compound of formula (I)
forming a pharmaceutically acceptable salt.

Reaction conditions for the process above will typically require activation of the carboxylic acid of formula (III) which can be achieved by many of the widely known 'amide coupling' agents such as 1-ethyl-3-(3-dimethylaminopropyl)carbodiimide (EDC) or propylphosphonic anhydride (commercially available under the trade mark "T3P"). This can be carried out in a suitable solvent such as dichloromethane, in the presence of a base such as triethylamine. The compound of formula (II), or salt thereof, may be present during activation of the carboxylic acid of formula (III), or may be added a short while afterwards. The reactions will typically occur at ambient room temperature (20 to 25° C.). As an alternative to carrying out the activation in situ, 'pre-activated' variants of the compound of formula (III) such as acid halides, acid anhydrides and esters (e.g. pentafluorophenyl esters) thereof can be used to react with the amine of formula (II) to form compounds of formula (I) under the appropriate conditions which will be known to the person skilled in the art.

Compounds of formula (II) in which $R^2$ is hydrogen, $R^3$ is hydrogen and $R^4$ is hydrogen may be prepared by reacting a compound of formula (IV), $R^1$—$B(OR^{20})_2$, where $R^{20}$ represents a hydrogen atom, an alkyl group, or both groups $OR^{20}$ together with the boron atom to which they are attached form a dioxoborolane ring (such as a pinacol borane) or a N-methyliminodiacetic acid boronate ester (MIDA boronate ester), and $R^1$ is as defined in formula (II), with 3-iodopyridine or 3-bromopyridine in the presence of a palladium catalyst according to the Suzuki-Miyaura reaction (see, for example, the following references:

1. Miyaura, Norio; Yamada, Kinji; Suzuki, Akira (1979). "A new stereospecific cross-coupling by the palladium-catalyzed reaction of 1-alkenylboranes with 1-alkenyl or 1-alkynyl halides". *Tetrahedron Letters* 20 (36): 3437-3440.
2. Miyaura, Norio; Suzuki, Akira (1979). "Stereoselective synthesis of arylated (E)-alkenes by the reaction of alk-1-enylboranes with aryl halides in the presence of palladium catalyst". *Chem. Comm.* (19): 866-867.
3. Miyaura, Norio; Suzuki, Akira (1995). "Palladium-Catalyzed Cross-Coupling Reactions of Organoboron Compounds". *Chemical Reviews* 95 (7): 2457-2483.

followed by a reduction step using hydrogen gas and a platinum (IV) oxide catalyst. In some instances removal of a protecting group, if present, may be performed prior to the reduction step. In other instances removal of a protecting group, if present, and alkylation of the deprotected atom may be performed prior to the reduction step.

Alternatively, compounds of formula (II) in which $R^2$ is hydrogen, $R^3$ is hydrogen and $R^4$ is hydrogen may be prepared as illustrated in Scheme 1 below:

Scheme 1

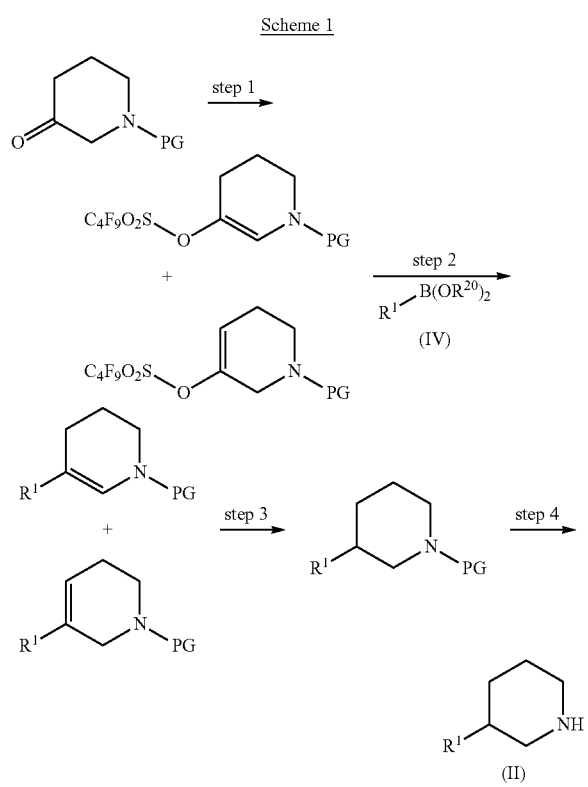

In Scheme 1, 'PG' denotes a nitrogen-protecting group. Step 1 is carried out in the presence of lithium bis(trimethylsilyl)amide and 1,1,2,2,3,3,4,4,4-nonafluorobutane-1-sulfonyl fluoride. The reaction product obtained can be a mixture of enol nonaflate isomers which, individually or taken as a mixture, is then reacted in step 2 with a compound of formula (IV) as described above under Suzuki-Miyaura reaction conditions. The product of step 2 is hydrogenated in step 3 using, for example, transition metal catalysed hydrogenation (e.g. palladium on carbon, $Pd(OH)_2$ on carbon, or platinum (IV) oxide) and, finally, the protecting group is removed in step 4, for example, using trifluoroacetic acid or hydrochloric acid in dichloromethane, when PG is tert-butoxycarbonyl (Boc) to give a compound of formula (II). Alternatively, where PG is benzyl or 4-methoxy benzyl, the deprotection may occur concomitantly with hydrogenation, or may proceed stepwise, typically effected by raising either the temperature and/or pressure of hydrogenation and/or by extending the reaction time of hydrogenation such that hydrogenolysis of the PG also occurs. Alternatively, where PG is benzyl or 4-methoxy benzyl, the deprotection may be effected by treatment with α-chloroethyl chloroformate (ACE-Cl) in a suitable solvent such as dichloromethane or dichloroethane followed by treatment with methanol according to the protocol of Olofson as described in the following reference: Olofson, Martz (1984). "A New Reagent for the Selective, High-Yield N-Dealkylation of Tertiary Amines: Improved Syntheses of Naltrexone and Nalbuphine". *J. Org. Chem.* 49: 2081-2082.

Compounds of formula (II) in which $R^2$ is other than hydrogen may be prepared as illustrated in Scheme 2 below:

Scheme 2

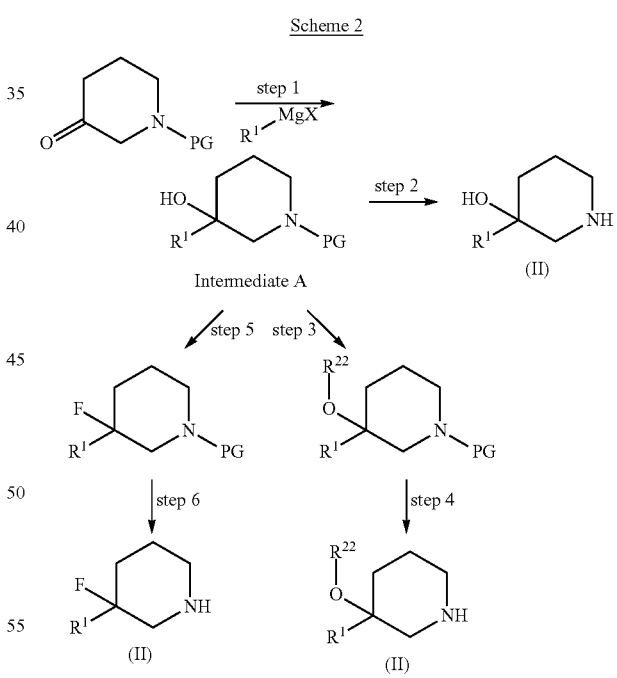

In Scheme 2, 'PG' denotes a nitrogen-protecting group, $R^{22}$ denotes a $C_1$-$C_3$ alkyl group and '$R^1$' has the same meaning as in formula (I). Step 1 is carried out in the presence of an organometallic reagent (eg aryl Grignard, $R^1$—MgX) and then the protecting group is removed in step 2, for example, using trifluoroacetic acid or hydrochloric acid in dichloromethane when PG is tert-butoxycarbonyl (Boc) to give a compound of formula (II) in which $R^2$ represents hydroxyl. Alternatively the product from step 1

(Intermediate A) can be alkylated (e.g. using a $C_1$-$C_3$ alkyl halide and a strong base, e.g. sodium hydride) (step 3) and the protecting group removed in step 4 by a procedure analogous to step 2 to give compounds of formula (II) in which $R^2$ represents $C_1$-$C_3$ alkoxy. Intermediate A may also be treated with a fluorinating agent (e.g. diethylaminosulfur trifluoride) (step 5) followed by removal of the protecting group in step 6 using a procedure analogous to step 2 to give a compound of formula (II) in which $R^2$ represents fluorine.

Compounds of formula (II) in which either $R^2$ and $R^3$ form a carbon-carbon single bond or $R^2$ and $R^4$ form a carbon-carbon single bond can be prepared by treating the product obtained from step 2 of Scheme 1 above with ACE-Cl followed by methanol (vide supra) to remove the protecting group.

Compounds of formula (II) in which $R^2$ and $R^3$ together with the carbon atoms to which they are attached form a cyclopropyl ring, or, $R^2$ and $R^4$ together with the carbon atoms to which they are attached form a cyclopropyl ring may be prepared by treating the product from step 2 of Scheme 1 with a Simmons-Smith cyclopropanating reagent such as an organozinc derived from diiodomethane, diethyl zinc and trifluoroacetic acid, for example, as described in the reference by J. C. Lorenz, J. Long, Z. Yang, S. Xue, X. Xie, Y. Shi, "A Novel Class of Tunable Zinc Reagents (RXZnCH$_2$Y) for Efficient Cyclopropanation of Olefins", *J. Org. Chem.*, 2004, 69, 327-334. The reaction may be followed by a deprotection step to remove any protecting groups, e.g. using ACE-Cl, or transition metal (e.g. platinum (IV) oxide) catalytic hydrogenolysis, to give the compound of formula (II).

Certain intermediates of formula (II) are novel compounds. Accordingly, the present invention also provides novel intermediate compounds of formula (II), such as compounds of formula (II) in which $R^1$ represents a pyridinyl group substituted by one or two substituents independently selected from halogen (e.g. fluorine, chlorine or bromine, particularly chlorine), $C_1$-$C_3$ alkyl (e.g. methyl, ethyl or isopropyl) and $C_1$-$C_2$ haloalkyl (e.g. trifluoromethyl).

Compounds of formulae (III) and (IV) are either commercially available, are well known in the literature or may be prepared using known techniques.

It will be appreciated by those skilled in the art that in the above processes certain functional groups such as phenol, hydroxyl or amino groups in the reagents may need to be protected by protecting groups. Thus, the preparation of compounds of formula (I) may involve, at an appropriate stage, the introduction and/or removal of one or more protecting groups.

The protection and deprotection of functional groups is described in Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) defined above may bear one or more radiolabels. Such radiolabels may be introduced by using radiolabel-containing reagents in the synthesis of the compounds of formula (I) or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly carbon atoms are to be understood to include $^{12}C$, $^{13}C$ and $^{14}C$, nitrogen atoms are to be understood to include 14N and, $^{15}N$ and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) above are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as prokineticin receptor modulators, and thus may be used in the treatment of schizophrenia and other psychotic disorders (e.g., schizophreniform disorder, schizoaffective disorder and psychosis); dementia (including behavioural and psychological symptoms of dementia, BPSD) and other cognitive disorders; anxiety disorders (e.g., generalized anxiety disorder, post-traumatic stress disorder and panic attack); mood disorders (e.g., depressive disorders, major depressive disorders, bipolar disorders including bipolar I and II, bipolar mania, bipolar depression); sleep disorders; disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); pain (e.g. neuropathic pain including chemotherapy induced pain, or visceral pain, or gastrointestinal pain); inflammatory conditions such as inflammatory bowel disease (e.g. Crohn's disease, Coeliac disease, ileitis, ulcerative colitis, enteropathy associated with seronegative arthropathies, microscopic or collagenous colitis, eosinophilic gastroenteritis, or pouchitis resulting after proctocolectomy and ileoanal anastomosis), cholecystitis, cholangitis, Behcet's disease, pericholangitis, graft versus host disease, sarcoidosis and chronic gastritis (e.g., autoimmune gastritis); neurodegenerative disorders (e.g. Parkinson's or Alzheimer's disease or multiple sclerosis); gastrointestinal disorders (e.g. irritable bowel syndrome (IBS) and functional dyspepsia); autoimmune disorders (e.g. rheumatoid arthritis); and addiction (e.g. drug addiction, alcohol addiction and nicotine addiction).

Thus, the present invention provides a compound of formula (I) or a pharmaceutically acceptable salt thereof as hereinbefore defined for use in therapy, in particular for the treatment of conditions whose development or symptoms are linked to prokineticin receptor activity.

The present invention also provides the use of a compound of formula (I) or a pharmaceutically acceptable salt thereof as hereinbefore defined for the preparation of a medicament for the treatment of conditions whose development or symptoms are linked to prokineticin receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of formula (I) and their pharmaceutically acceptable salts as defined above may be used in the treatment of the positive symptoms of schizophrenia, schizophreniform disorder or schizoaffective disorder (e.g. voices or hallucinations), cognitive disorders (such as dementia and impaired learning), pain (such as neuropathic pain), irritable bowel diseases, and also irritable bowel syndrome.

The invention also provides a method of treating at least one symptom or condition associated with schizophrenia and other psychotic disorders (e.g., schizophreniform disorder, schizoaffective disorder and psychosis); dementia (including behavioural and psychological symptoms of dementia, BPSD) and other cognitive disorders; anxiety disorders (e.g., generalized anxiety disorder, post-traumatic stress disorder and panic attack); mood disorders (e.g., depressive disorders, major depressive disorders, bipolar disorders including bipolar I and II, bipolar mania, bipolar depression); sleep disorders; disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); pain (e.g. neuropathic pain including chemotherapy induced pain, or visceral pain, or gastrointestinal pain); inflammatory conditions such as inflammatory bowel disease (e.g. Crohn's disease, Coeliac disease, ileitis, ulcerative colitis, enteropathy associated with seronegative arthropathies, microscopic or collagenous colitis, eosinophilic gastroenteritis, or pouchitis resulting after proctocolectomy and ileoanal anastomosis), cholecystitis, cholangitis, Behcet's disease, pericholangitis, graft versus host disease, sarcoidosis and chronic gastritis (e.g., autoimmune gastritis); neurodegenerative disorders (e.g. Parkinson's or Alzheimer's disease or multiple sclerosis); gastrointestinal disorders (e.g. irritable bowel syndrome (IBS) and functional dyspepsia); autoimmune disorders (e.g. rheumatoid arthritis); and addiction (e.g. drug addiction, alcohol addiction and nicotine addiction) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of a compound according to the invention (i.e. a compound of formula (I) or a pharmaceutically acceptable salt thereof), if inhaled, may be in the range from 0.05 micrograms per kilogram body weight (m/kg) to 100 micrograms per kilogram body weight (μg/kg). Alternatively, if the compound is administered orally, then the daily dosage of the compound of the invention may be in the range from 0.01 micrograms per kilogram body weight (m/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of formula (I) and pharmaceutically acceptable salts thereof as defined above may also be administered in conjunction with other compounds used for the treatment of the above conditions.

The invention therefore further relates to combination therapies wherein a compound of formula (I) or a pharmaceutically acceptable salt thereof as previously defined or a pharmaceutical composition or formulation comprising a compound of formula (I) or a pharmaceutically acceptable salt thereof as previously defined is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrigine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof;

(vii) Parkinson's therapies including, for example, deprenyl, L-dopa, Requip, Mirapex, monoamine oxidase type B (MAO-B) inhibitors such as selegiline and rasagiline, catechol-O-methyl transferase (COMT) inhibitors such as Tasmar, A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;

(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;

(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;

(xi) neuropathic pain therapies including, for example, gabapentin, lidoderm, and pregablin, and equivalents and pharmaceutically active isomer(s) and/or metabolite(s) thereof;

(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;

(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xv) 5HT1B ligands such as, for example, compounds disclosed in WO 99/05134 and WO 02/08212;

(xvi) mGluR2 agonists;

(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xviii) chemokine receptor CCR1 inhibitors; and (xix) delta opioid agonists such as, for example, compounds disclosed in WO 97/23466 and WO 02/094794.

Such combination products employ the compound of formula (I) or a pharmaceutically acceptable salt thereof as previously defined within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents independently selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples, in which the starting materials and reagents used are available from commercial suppliers.

Nuclear magnetic resonance (NMR) spectra were recorded at 400 MHz and at 300.3K unless otherwise stated; the chemical shifts ($\delta$) are reported in parts per million. Spectra were recorded using either a Bruker 400 Avance instrument fitted with a 5 mm BBFO probe or DUL probe with instrument controlled by Bruker TopSpin 2.1 software, or by a Jeol Lambda spectrometer (JN-LMA400) instrument fitted with a 5 mm Jeol TH5 probe with instrument controlled by Jeol Delta software v4.3.5.

In respect of NMR analysis, compounds of the formula (I) frequently exhibit signal splitting and/or broadening due to conformationally restricted motion of the pendant substituents of the N-acyl piperidine ring. These effects are temperature and solvent dependent and can complicate the assignment of signals and coupling constants. For the avoidance of doubt, such split or broadened signals have been assigned a chemical shift range as observed and have been designated as multiplets.

Purity was assessed using one or more of the following:

UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia. Mass spectra were recorded with a Waters SQD single quadrupole mass spectrometer using atmospheric pressure ionisation.

Perkin Elmer 200 series system equipped with Agilent Poroshell 120 column (SB-C18, 4.6 mm id×30 mm, 2.7 m) operated at 20° C. Mobile phases consisted of acetonitrile and water, both containing 0.1% v/v formic acid. Mass spectra were recorded with a PE SCIEX API 2000 MS/MS mass spectrometer. The system was controlled by Analyst software (version 1.5.1).

Compounds were purified using normal phase chromatography on silica, using Biotage or Isolute KP-Sil cartridges or Kinesis Telos Silica cartridges, or on basic silica, using Biotage or Isolute KP-NH cartridges, or by reverse phase chromatographic methods, using Biotage or Isolute KP-C18-HS cartridges or by SCX-2 catch-release cartridges, or by Preparative HPLC, or by Supercritical Fluid Chromatography (SFC).

Preparative HPLC was performed using one or more of the following:

Agilent Technologies 1100 Series system or a Waters autopurification LC/MS system typically using Waters 19 mm id×100 mm long C18 columns such as XBridge or SunFire 5 μm materials at room temperature.

Gilson HPLC system using Waters XBridge Column (C18, 5 μm, 19 mm id×250 mm), controlled by UniPoint software (version 2.10)

Waters autopurification LC/MS system using Varian Column (C18, 5 μm, 21.2 mm id×150 mm), controlled by MassLynx software (version 4.0 SP4) Mobile phases typically consisted of acetonitrile or methanol mixed with water containing either 0.1% formic acid or 0.1% ammonia, unless stated otherwise.

Room temperature in the following examples means the temperature ranging from 20° C. to 25° C.

The following abbreviations are used in the Examples:
ACE-Cl α-chloroethyl chloroformate
ACN acetonitrile
aq. aqueous
CHCl$_3$ chloroform
CV column volumes
DCM dichloromethane
DMAP 4-(dimethylamino)pyridine
DMSO dimethyl sulfoxide
DMF dimethylformamide
DPPF 1,1'-bis(diphenylphosphanyl) ferrocene
EDC 1-ethyl-3-(3-dimethylaminopropyl)carbodiimide
EtOAc ethyl acetate
EtOH ethanol
g grams
HBr hydrobromic acid
HCl hydrochloric acid
HOAt 1-hydroxy-7-azabenzotriazole
HPLC high pressure liquid chromatography
LCMS liquid chromatographic mass spectrometry
LiHMDS lithium bis(trimethylsilyl)amide
MgSO$_4$ magnesium sulphate
MeOH methanol
mg milligrams
mins minutes
mL milliliters
mmol millimoles
MS mass spectrometry
NaHCO$_3$ sodium hydrogen carbonate
NaOH sodium hydroxide
Na$_2$SO$_4$ sodium sulphate
NH$_3$ ammonia
NH$_4$Cl ammonium chloride
NMP 1-methyl-2-pyrrolidone
NMR nuclear magnetic resonance
ppm parts per milion
Rt retention time
sat. saturated
SFC supercritical fluid chromatography
TFA trifluoroacetic acid
THF tetrahydrofuran

1. INTERMEDIATES

Intermediate 1 6-Chloropyridazine-4-carboxylic acid

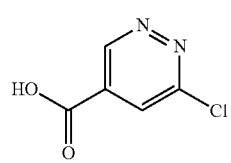

To a stirred solution of methyl 6-chloropyridazine-4-carboxylate (CAS 1093860-48-0, 5.05 g, 29.3 mmol) in THF (10 mL)/water (20 mL) was added lithium hydroxide (1.402 g, 58.5 mmol). After 90 minutes the reaction mixture was acidified to pH 1-2 with conc. HCl (11.8 M, 5 mL) and concentrated in vacuo to remove the THF. The resultant precipitate was stirred in the predominantly aqueous medium at ambient temperature for approximately 30 minutes and was then filtered through a sinter under vacuum and dried in a vacuum oven afford the title compound.

MS ES$^+$:159

Intermediate 2
1-Methyl-2-(piperidin-3-yl)-1H-indole

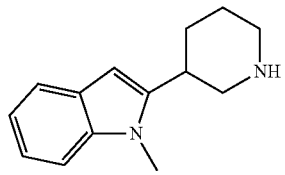 [SMILES: Cn1c(C2CCCNC2)cc2ccccc21]

To a stirred solution of 2-(1-benzyl-1,2,5,6-tetrahydropyridin-3-yl)-1-methyl-1H-indole (Intermediate 3; 0.217 g, 0.718 mmol) in ethanol (10 mL) was added ammonium formate (0.452 g, 7.18 mmol) and palladium hydroxide on carbon (20 wt. %, 0.050 g). The reaction mixture was heated to reflux under an atmosphere of nitrogen for 5.5 hours. The reaction was then removed from heat and allowed to cool and was filtered through diatomaceous earth. The solvent was removed in vacuo and the crude product was purified by reverse phase preparative HPLC eluted with acetonitrile/water (with 0.1% ammonia) to afford the title compound.

MS ES$^+$:215

Intermediate 3 2-(1-Benzyl-1,2,5,6-tetrahydropyridin-3-yl)-1-methyl-1H-indole

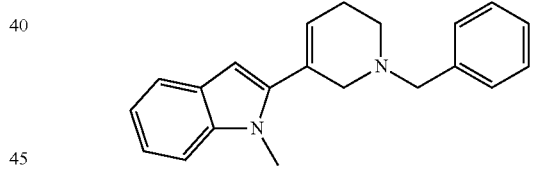

A microwave vial was charged with 1-benzyl-1,2,5,6-tetrahydropyridin-3-yl 1,1,2,2,3,3,4,4,4-nonafluorobutane-1-sulfonate (Intermediate 4; 0.986 g, 2.093 mmol), 1-methyl-2-(4,4,5,5-tetramethyl-1,3,2-dioxaborolan-2-yl)-1H-indole (CAS 596819-10-2; 0.565 g, 2.197 mmol) and potassium carbonate (0.868 g, 6.28 mmol) in dioxane (15 mL)/water (3.75 mL). The stirred mixture was degassed by bubbling nitrogen through it for 5 minutes. Tetrakis(triphenylphosphine)palladium(0) (0.121 g, 0.105 mmol) was added and the mixture was degassed for another minute before being sealed and irradiated in a microwave reactor at 100° C. for 20 minutes. The reaction mixture was diluted with EtOAc and washed with water then brine and the organic part was loaded onto a pre-equilibrated cation exchange cartridge (SCX-2) and was eluted with EtOAc then EtOAc/[1M NH$_3$ in MeOH] (4:1) and then EtOAc/[2M NH$_3$ in MeOH] (4:1). The product containing fractions were combined and reduced in vacuo to afford the title compound.

MS ES$^+$:303

Intermediate 4
1-Benzyl-1,2,5,6-tetrahydropyridin-3-yl 1,1,2,2,3,3,4,4,4-nonafluorobutane-1-sulfonate

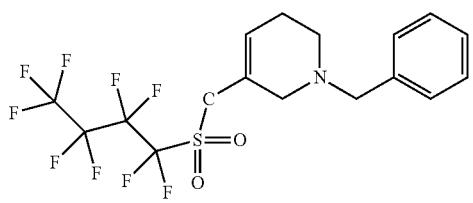 [SMILES: O=S(=O)(CC1=CCCN(Cc2ccccc2)C1)C(F)(F)C(F)(F)C(F)(F)C(F)(F)F]

1-Benzylpiperidin-3-one hydrate hydrochloride (CAS 50606-58-1) was freshly converted to free base by dissolving in water/ACN (1:1, 0.1 g/mL) and loading onto an SCX-2 cartridge (5 g sorbent/1 g substrate). The cartridge was washed with water/acetonitrile (10 vols), acetonitrile (10 vols) then the free base eluted with acetonitrile/[2M NH$_3$ in MeOH] (4:1) (50 vols). 1-Benzylpiperidin-3-one (6.45 g, 34.1 mmol) was dissolved in anhydrous THF (100 mL) and the solution was stirred at −78° C. under a nitrogen atmosphere. To the stirred solution was added LiHMDS [1.0M in THF] (47.7 ml, 47.7 mmol) over 5 minutes. To the stirred reaction mixture was added 1,1,2,2,3,3,4,4,4-nonafluorobutane-1-sulfonyl fluoride (CAS 375-72-4; 9.18 ml, 51.1 mmol). After 75 minutes the reaction mixture removed from the cold-bath and allowed to warm to ambient temperature. After 1 hour the reaction was quenched with saturated aqueous NaHCO$_3$, concentrated in vacuo to approximately one third (⅓) volume and extracted into diethyl ether. The organic phase was back extracted with brine and dried over Na$_2$SO$_4$. The crude product was purified by column chromatography (silica gel) eluted with 0-20% EtOAc in petroleum ether 40-60 to give the title compound.
MS ES$^+$:472

Intermediate 5 2-{1-(6-Chloropyridazine-4-carbonyl)piperidin-3-yl]-1-methyl-1H-indole

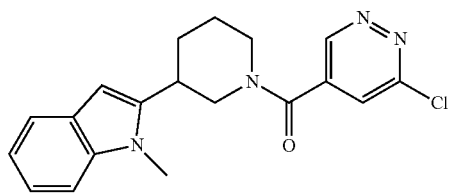 [SMILES: Cn1c(C2CCCN(C(=O)c3cnnc(Cl)c3)C2)cc2ccccc21]

To a stirred solution of 1-methyl-2-(piperidin-3-yl)-1H-indole (Intermediate 2; 0.083 g, 0.387 mmol) and 6-chloropyridazine-4-carboxylic acid (Intermediate 1; 0.074 g, 0.465 mmol) in dichloromethane (2 mL) was added triethylamine (0.108 ml, 0.775 mmol) and then 2,4,6-tripropyl-1,3,5,2,4,6-trioxatriphosphinane 2,4,6-trioxide (50 wt. % solution in EtOAc) (0.577 ml, 0.968 mmol). The reaction mixture was stirred at ambient temperature for 20 hours. The reaction was quenched with saturated aqueous NaHCO$_3$ and the mixture was separated using a phase separator cartridge. The aqueous was extracted with more DCM and the combined organics were eluted through a cation exchange cartridge (SCX-2, 1 g). The solvent was removed in vacuo afford the title compound which was used without further purification.
MS ES$^+$:355

Intermediate 6 1-Ethyl-2-(piperidin-3-yl)-1H-indole

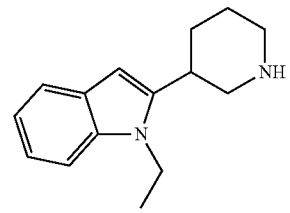 [SMILES: CCn1c(C2CCCNC2)cc2ccccc21]

A solution of 2-(1-benzyl-1,2,5,6-tetrahydropyridin-3-yl)-1-ethyl-1H-indole (Intermediate 7; 0.27 g, 0.853 mmol) in MeOH (30 mL) was cycled through a hydrogen generating flow reactor fitted with a 20% palladium(II) hydroxide on carbon catalyst cartridge at ambient temperature and pressure at 1.0 ml/min flow rate. After 5 hours hydrogen generation was stopped and the eluent was flushed from the reactor and the system was washed through with MeOH and concentrated in vacuo to afford the title compound.
MS ES$^+$:229

Intermediate 7 2-(1-Benzyl-1,2,5,6-tetrahydropyridin-3-yl)-1-ethyl-1H-indole

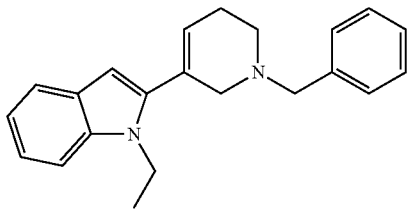 [SMILES: CCn1c(C2=CCCN(Cc3ccccc3)C2)cc2ccccc21]

To a stirred solution of 2-(1-benzyl-1,2,5,6-tetrahydropyridin-3-yl)-1H-indole (Intermediate 8; 0.5 g, 1.734 mmol) in DMF (5 mL) was added sodium hydride (60 wt. % in mineral oil) (0.083 g, 2.081 mmol). After 20 minutes iodoethane (0.209 ml, 2.60 mmol) was added. The vial was purged with nitrogen, sealed and stirred at ambient temperature. After 16.5 hours the reaction quenched with saturated aqueous NH$_4$Cl. The mixture was partitioned between EtOAc and saturated aqueous NaHCO$_3$, the aqueous layer was removed and the organic phase was washed with water then brine. The crude product was purified by column chromatography (silica gel) eluted with 0-25% ethyl acetate/petrol to afford the title compound.
MS ES$^+$:317

Intermediate 8 2-(1-Benzyl-1,2,5,6-tetrahydropyridin-3-yl)-1H-indole

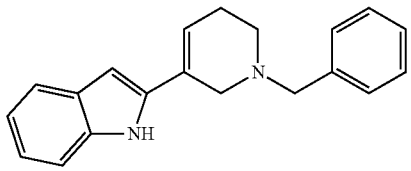 [SMILES: C1=C(c2cc3ccccc3[nH]2)CN(Cc2ccccc2)CC1]

To a stirred solution of tert-butyl 2-(1-benzyl-1,2,5,6-tetrahydropyridin-3-yl)-1H-indole-1-carboxylate (Intermediate 9; 3.44 g, 8.85 mmol) in DCM (45 mL) was added TFA (5 mL). The reaction was stirred at ambient temperature. After 18 hours the reaction mixture was concentrated in vacuo, azeotroped with DCM and the residue was neutralised by addition of 2 M ammonia in methanol and concentrated in vacuo. The crude product was dissolved in DCM and loaded onto pre-equilibrated cation exchange cartridge (SCX-2, 50 g). This was washed with DCM then eluted off with DCM/[2M NH$_3$ in MeOH]. The crude product was purified by column chromatography (silica gel) eluted with 0-15% {EtOAc/[2M NH$_3$ in MeOH (9:1)]}/petroleum ether 40-60 to afford the title compound.

MS ES$^+$:289

Intermediate 9 tert-Butyl 2-(1-benzyl-1,2,5,6-tetra-hydropyridin-3-yl)-1H-indole-1-carboxylate

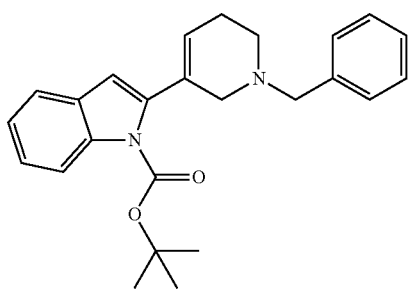 [SMILES: CC(C)(C)OC(=O)n1c(C2=CCCN(Cc3ccccc3)C2)cc2ccccc21]

Prepared as described for 2-(1-benzyl-1,2,5,6-tetrahydropyridin-3-yl)-1-methyl-1H-indole (Intermediate 3) from 1-benzyl-1,2,5,6-tetrahydropyridin-3-yl 1,1,2,2,3,3,4,4,4-nonafluorobutane-1-sulfonate (Intermediate 4; 5.62 g, 11.92 mmol) and {1-[(tert-butoxy)carbonyl]-1H-indol-2-yl}boronic acid (CAS 213318-44-6; 3.11 g, 11.92 mmol) using tetrakis(triphenylphosphine)palladium(0) (0.689 g, 0.596 mmol) and potassium carbonate (4.94 g, 35.8 mmol) in water (8 mL) and 1,4-dioxane (32 mL) and irradiated in a microwave at 100° C. for 20 minutes to afford the title compound.

MS ES$^+$:389

Intermediate 10 2-[1-(6-Chloropyridazine-4-carbonyl)piperidin-3-yl]-1-ethyl-1H-indole

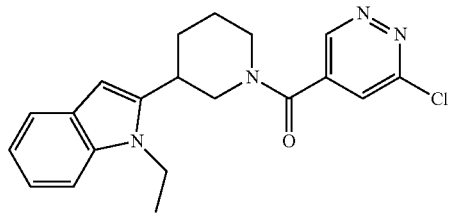 [SMILES: CCn1c(C2CCCN(C(=O)c3cnnc(Cl)c3)C2)cc2ccccc21]

Prepared as described for Intermediate 5, from 6-chloropyridazine-4-carboxylic acid (Intermediate 1; 65.8 mg, 0.415 mmol) and 1-ethyl-2-(piperidin-3-yl)-1H-indole (Intermediate 6; 79 mg, 0.346 mmol) to afford the title compound.

MS ES$^+$:369

Intermediate 11 2-[1-(6-Chloropyridazine-4-carbonyl)piperidin-3-yl]-1-(propan-2-yl)-1H-indole

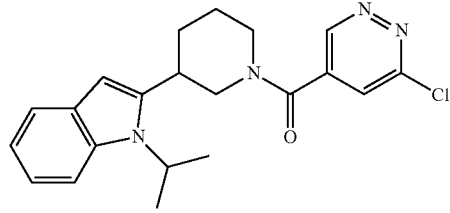 [SMILES: CC(C)n1c(C2CCCN(C(=O)c3cnnc(Cl)c3)C2)cc2ccccc21]

Prepared as described for 2-{1-(6-chloropyridazine-4-carbonyl)piperidin-3-yl]-1-methyl-1H-indole (Intermediate 5) from 6-chloropyridazine-4-carboxylic acid (Intermediate 1; 0.076 g, 0.480 mmol) and 2-(piperidin-3-yl)-1-(propan-2-yl)-1H-indole (Intermediate 12; 0.097 g, 0.400 mmol) to afford the title compound.

MS ES$^+$:383

Intermediate 12 2-(Piperidin-3-yl)-1-(propan-2-yl)-1H-indole

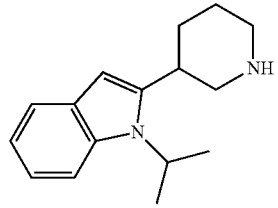 [SMILES: CC(C)n1c(C2CCCNC2)cc2ccccc21]

Prepared as described for 1-ethyl-2-(piperidin-3-yl)-1H-indole (Intermediate 6) from 2-(1-benzyl-1,2,5,6-tetrahydropyridin-3-yl)-1-(propan-2-yl)-1H-indole (Intermediate 13; 0.3 g, 0.908 mmol), except that the reaction cycling time was 2.5 hours, to afford the title compound.

MS ES$^+$:243

Intermediate 13 2-(1-Benzyl-1,2,5,6-tetrahydropyridin-3-yl)-1-(propan-2-yl)-1H-indole

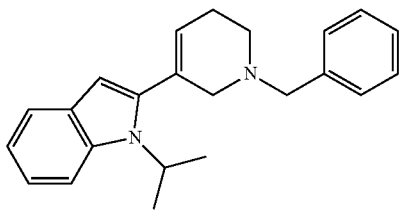 [SMILES: CC(C)n1c(C2=CCCN(Cc3ccccc3)C2)cc2ccccc21]

To a stirred solution of palladium(II) acetate (5.88 mg, 0.026 mmol) and 1,3-bis-(2,6-diisopropylphenyl)-imidazolium chloride (0.011 g, 0.026 mmol) in toluene (1.0 mL) was added potassium 2-methylpropan-2-olate (0.117 g, 1.047 mmol). The reaction mixture was stirred at ambient temperature in a sealed tube under a nitrogen atmosphere for 10 minutes after which time a solution of 2-[2-(1-benzyl-1,2,5,6-tetrahydropyridin-3-yl)ethynyl]-N-(propan-2-yl)aniline (Intermediate 14; 0.173 g, 0.524 mmol) in toluene (1 mL)

was added. The reaction mixture was heated to 80° C. for 50 minutes and then allowed to cool to ambient temperature before being diluted with EtOAc and washed with saturated aqueous NaHCO₃ and then brine. The combined organics were dried over MgSO₄ and purified by column chromatography (silica gel) eluted with 0-25% ethyl acetate/petroleum 40-60 to afford the title compound.

MS ES⁺:331

Intermediate 14 2-[2-(1-Benzyl-1,2,5,6-tetrahydropyridin-3-yl)ethynyl]-N-(propan-2-yl)aniline

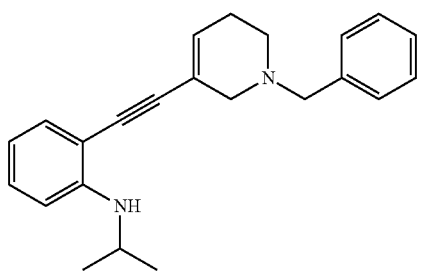 [SMILES: CC(C)Nc1ccccc1C#CC1=CCCN(Cc2ccccc2)C1]

To a stirred solution of 2-ethynyl-N-(propan-2-yl)aniline (Intermediate 15; 0.242 g, 1.520 mmol) and 1-benzyl-1,2,5,6-tetrahydropyridin-3-yl 1,1,2,2,3,3,4,4,4-nonafluorobutane-1-sulfonate (Intermediate 4; 0.716 g, 1.520 mmol) in DMF (7.5 mL) was added triethylamine (0.636 ml, 4.56 mmol), palladium(II) acetate (0.014 g, 0.061 mmol), copper (I) iodide (0.014 g, 0.076 mmol) and DPPF (0.051 g, 0.091 mmol). The reaction flask was purged with nitrogen and heated at 70° C. under nitrogen. After 2 hours the reaction was allowed to cool, diluted with EtOAc, washed with water then brine. The crude product was purified by column chromatography (silica gel) eluted with 0-25% EtOAc/petroleum ether 40-60 to afford the title compound.

MS ES⁺:331

Intermediate 15 2-Ethynyl-N-(propan-2-yl)aniline

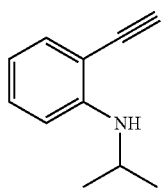

To a stirred solution of 2-ethynylaniline (CAS 52670-38-9; 1 g, 8.54 mmol) in dichloromethane (25 mL) was added acetic acid (1.955 ml, 34.1 mmol), 2-methoxyprop-1-ene (CAS 116-11-0; 3.27 ml, 34.1 mmol) and then sodium triacetoxyborohydride (2.71 g, 12.80 mmol). The reaction was stirred at ambient temperature for 20 hours and then quenched with saturated aqueous NaHCO₃. The organic phase was separated and the aqueous was extracted with DCM. The crude product was purified by column chromatography (silica gel) eluted with 0-10% ethyl acetate/petroleum ether 40-60 to afford the title compound.

¹H NMR (400 MHz, CDCl₃) δ ppm 1.28 (d, J=6.32 Hz, 6H) 3.42 (s, 1H) 3.59-3.80 (m, 1H) 6.55-6.69 (m, 2H) 7.14-7.27 (m, 1H) 7.35 (dd, J=7.58, 1.52 Hz, 1H)

Intermediate 16 tert-Butyl N-(1-methyl-4-{3-[1-(propan-2-yl)-1H-indol-2-yl]piperidine-1-carbonyl}-1H-pyrazol-3-yl)carbamate

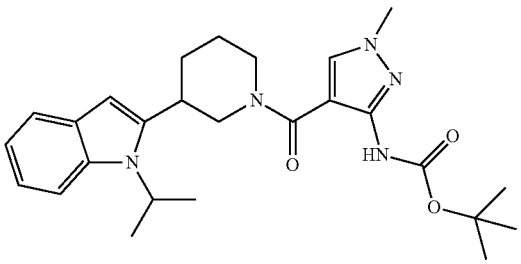 [SMILES: CC(C)n1c(C2CCCN(C(=O)c3cn(C)nc3NC(=O)OC(C)(C)C)C2)cc2ccccc21]

Prepared as described for 2-{1-(6-chloropyridazine-4-carbonyl)piperidin-3-yl]-1-methyl-1H-indole (Intermediate 5) from 2-(piperidin-3-yl)-1-(propan-2-yl)-1H-indole (Intermediate 12; 0.048 g, 0.198 mmol) and 3-{[tert-butoxy)carbonyl]amino}-1-methyl-1H-pyrazole-4-carboxylic acid (Intermediate 17; 0.057 g, 0.238 mmol) in dichloromethane (1 mL), except that the work-up was performed as follows:

The reaction mixture was quenched by addition of saturated aqueous NaHCO₃ and then diluted in EtOAc and washed first with saturated aqueous NaHCO₃ and then dilute aqueous HCl (3%) and then brine. The solvent was removed in vacuo to afford the title compound which was used without further purification.

MS ES⁺:466

Intermediate 17 3-{[(tert-Butoxy)carbonyl]amino}-1-methyl-1H-pyrazole-4-carboxylic acid

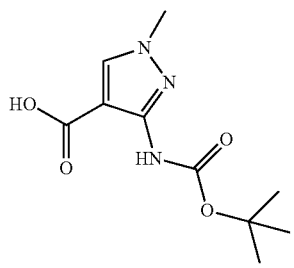 [SMILES: Cn1cc(C(=O)O)c(NC(=O)OC(C)(C)C)n1]

To a stirred suspension of ethyl 3-{bis[(tert-butoxy)carbonyl]amino}-1-methyl-1H-pyrazole-4-carboxylate (Intermediate 18; 2.18 g, 5.90 mmol) in EtOH (30 mL) was added sodium hydroxide solution (2M, 5.90 mL, 11.80 mmol) under a nitrogen atmosphere. The reaction was heated to reflux for 4 hours. Additional sodium hydroxide (2M, 5.90 mL, 11.80 mmol) was added and the reaction was heated to reflux for a further 2 hours. The reaction mixture was concentrated in vacuo and was acidified with aqueous hydrogen chloride (2M) then partitioned between ethyl acetate and water. The phases were separated and the aqueous phase extracted with ethyl acetate. The combined organics were dried (MgSO₄) and concentrated in vacuo to afford the title compound that was used without purification.

MS ES⁻:240

Intermediate 18 Ethyl 3-{bis[(tert-butoxy)carbonyl]amino}-1-methyl-1H-pyrazole-4-carboxylate

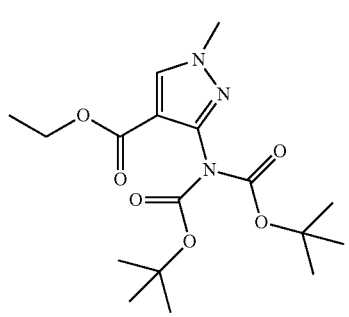 [SMILES: CCOC(=O)c1cn(C)nc1N(C(=O)OC(C)(C)C)C(=O)OC(C)(C)C]

To a mixture of ethyl 3-amino-1-methyl-1H-pyrazole-4-carboxylate (CAS 21230-43-3; 1 g, 5.91 mmol), triethylamine (2.472 mL, 17.73 mmol) and DMAP (0.01 g, 0.082 mmol) in THF (30 mL) was added di-tert-butyl dicarbonate (3.23 g, 14.78 mmol). The reaction was heated to reflux for 48 hours. Additional di-tert-butyl dicarbonate (3.23 g, 14.78 mmol) is was added and the solution heated to reflux overnight. The mixture was partitioned between ethyl acetate and water. The phases were separated and the aqueous extracted with ethyl acetate. The combined organics were washed with brine, passed through a phase separator cartridge to remove the aqueous phase and concentrated in vacuo to afford the title compound, used in the next step without further purification.

MS ES$^+$:370

Intermediate 19 1-Ethyl-5-methyl-2-(piperidin-3-yl)-1H-indole hemi-formate

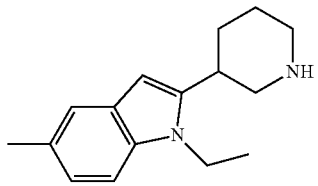 [SMILES: CCn1c(C2CCCNC2)cc2cc(C)ccc21]

To a solution of 1-ethyl-5-methyl-2-(pyridin-3-yl)-1H-indole (Intermediate 20; 0.75 g, 3.17 mmol) and HCl (32%, 0.27 mL, 3.17 mmol) in EtOH (30 mL) under an atmosphere of nitrogen was added platinum(IV) oxide (0.072 g, 0.317 mmol). The reaction vessel was evacuated and back-filled with hydrogen gas and the reaction was stirred at ambient temperature for 2 days during which time the hydrogen atmosphere was replenished three times. The reaction mixture was filtered through diatomaceous earth, concentrated in vacuo and purified by reverse phase preparative HPLC eluted with acetonitrile/water (with 0.1% formic acid) to afford the title compound.

MS ES$^+$:243

Intermediate 20 1-Ethyl-5-methyl-2-(pyridin-3-yl)-1H-indole

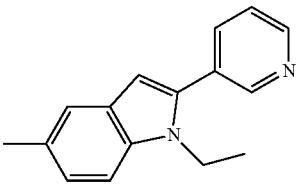 [SMILES: CCn1c(-c2cccnc2)cc2cc(C)ccc21]

To a stirred suspension of sodium hydride (60% in mineral oil, 0.428 g, 10.69 mmol) in DMF (70 mL) at 0° C. was added a solution of 5-methyl-2-(pyridin-3-yl)-1H-indole (Intermediate 21; 1.485 g, 7.13 mmol) in DMF (15 mL), dropwise, over 20 minutes. Iodoethane (2.22 g, 14.26 mmol) was added and the reaction mixture was stirred at 0° C. for 1 hour, and then allowed to warm to ambient temperature and stirred for another 3 hours. The reaction mixture was poured onto ice/water and extracted with DCM. The combined organics were dried (Na$_2$SO$_4$) and the crude product was purified by column chromatography (silica gel) eluted with 12% EtOAc in petroleum ether to afford the title compound.

MS ES$^+$:237

Intermediate 21 5-Methyl-2-(pyridin-3-yl)-1H-indole

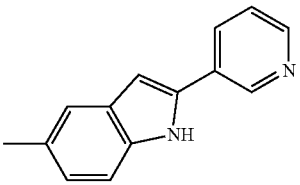 [SMILES: Cc1ccc2[nH]c(-c3cccnc3)cc2c1]

To a stirred solution of tert-butyl 5-methyl-2-(pyridin-3-yl)-1H-indole-1-carboxylate (Intermediate 22, 3.37 g, 10.93 mmol) in DCM (33.7 mL) was added anisole (16.85 mL) and TFA (33.7 mL). The reaction mixture was stirred at ambient temperature overnight and was then concentrated in vacuo, quenched with saturated aqueous NaHCO$_3$ and extracted with DCM. The organic phase was further treated with saturated aqueous NaHCO$_3$, dried (Na$_2$SO$_4$), concentrated in vacuo and triturated with diethyl ether to afford the title compound.

MS ES$^+$:209

Intermediate 22 tert-Butyl 5-methyl-2-(pyridin-3-yl)-1H-indole-1-carboxylate

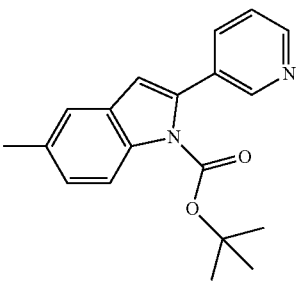 [SMILES: Cc1ccc2c(c1)cc(-c1cccnc1)n2C(=O)OC(C)(C)C]

To a stirred mixture of 3-iodopyridine (CAS 1120-90-7; 2.03 g, 9.91 mmol) and {1-[(tert-butoxy)carbonyl]-5-methyl-1H-indol-2-yl}boronic acid (CAS 475102-14-8, 3.0 g, 10.91 mmol) in toluene (50 mL) and EtOH (12.2 mL) was added aqueous sodium carbonate solution (2.0M, 14.72 mL, 29.73 mmol). The reaction mixture was degassed with nitrogen and tetrakis(triphenylphosphine)palladium(0) (0.389 g, 0.33 mmol) was added. The reaction mixture was heated at 90° C. for 16 hours and then allowed to cool and was diluted with EtOAc, washed with water and brine. The organics were dried (Na$_2$SO$_4$) and the crude product was purified by column chromatography (silica gel) eluted with 20% EtOAc in petroleum ether 40-60 to afford the title compound.

MS ES$^+$:309

Intermediate 23 2-[1-(6-Chloropyridazine-4-carbonyl)piperidin-3-yl]-1-ethyl-3-methyl-1H-indole

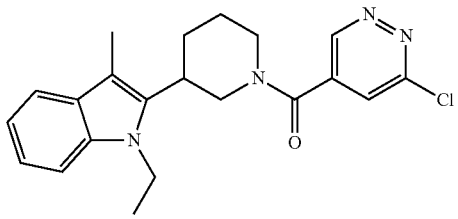 [SMILES: CCn1c(C2CCCN(C(=O)c3cnnc(Cl)c3)C2)c(C)c2ccccc21]

Prepared as described for 2-{1-(6-chloropyridazine-4-carbonyl)piperidin-3-yl]-1-methyl-1H-indole (Intermediate 5) from 6-chloropyridazine-4-carboxylic acid (Intermediate 1; 88 mg, 0.552 mmol) and 1-ethyl-3-methyl-2-(piperidin-3-yl)-1H-indole hemi-formate salt (Intermediate 24; 132 mg, 0.502 mmol) with the exception that column chromatography (silica gel) using 0-100% EtOAc in petroleum ether 40-60 was used in place of solid phase extraction to afford the title compound.

MS ES$^+$:383

Intermediate 24 1-Ethyl-3-methyl-2-(piperidin-3-yl)-1H-indole hemi-formate salt

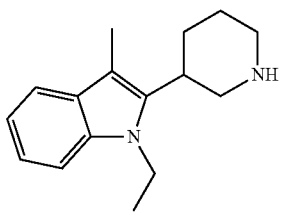 [SMILES: CCn1c(C2CCCNC2)c(C)c2ccccc21]

Prepared as described for 1-ethyl-5-methyl-2-(piperidin-3-yl)-1H-indole hemi-formate (Intermediate 19) from 1-ethyl-3-methyl-2-(pyridin-3-yl)-1H-indole (Intermediate 25; 1.3 g, 5.51 mmol), except that a solution of HCl in 1,4-dioxane (4M, 1.37 mL, 5.48 mmol) was used. The crude product was purified by reverse phase preparative HPLC eluted with acetonitrile/water (with 0.1% formic acid) to afford the title compound.

MS ES$^+$:243

Intermediate 25 1-Ethyl-3-methyl-2-(pyridin-3-yl)-1H-indole

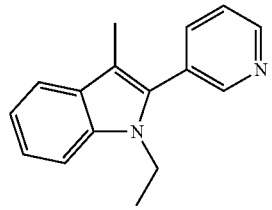 [SMILES: CCn1c(-c2cccnc2)c(C)c2ccccc21]

Prepared as described for 1-ethyl-5-methyl-2-(pyridin-3-yl)-1H-indole (Intermediate 20) from 3-methyl-2-(pyridin-3-yl)-1H-indole (Intermediate 26, free-base; 4 g, 19 mmol) and iodoethane (6 g, 38 mmol) except that the reaction was maintained at 0° C. for 1 hour before being poured onto ice/water and extracted into DCM. The combined organics were washed with water and brine and was concentrated in vacuo and the residue was then partitioned between diethyl ether and brine and then water and was then purified by column chromatography (silica gel) eluted with DCM to afford the title compound.

MS ES$^+$:237

Intermediate 26 3-Methyl-2-(pyridin-3-yl)-1H-indole hydrochloride

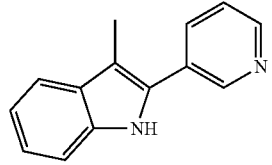 [SMILES: Cc1c(-c2cccnc2)[nH]c2ccccc12]

To a stirred solution of crude 3-[1-(2-phenylhydrazin-1-ylidene)propyl]pyridine (Intermediate 27, not isolated) in EtOH (100 mL) was added a solution of HCl in 1,4-dioxane (4.0M, 37.1 mL, 148.4 mmol) and the reaction mixture was heated to reflux for 3 hours. The reaction mixture was allowed to cool to ambient temperature and was poured onto ice. The resulting precipitate was collected by filtration, washed with THF and air dried to afford the title compound used in the next step without further purification.

MS ES$^+$:209

Intermediate 27 3-[1-(2-Phenylhydrazin-1-ylidene)propyl]pyridine

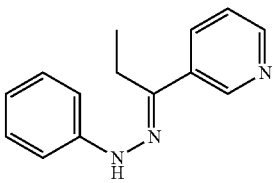 [SMILES: CC/C(=N\Nc1ccccc1)c1cccnc1]

A stirred solution of 1-(pyridin-3-yl)propan-1-one (CAS 1570-48-5; 5.08 g, 37.6 mmol) and phenyl hydrazine hydrochloride (5.44 g, 37.6 mmol) in EtOH (100 mL) was heated at reflux for 1 hour to afford the title compound which was used in the next step without isolation or further purification.
MS ES+:226

Intermediate 28 2-[1-(6-Chloropyridazine-4-carbonyl)piperidin-3-yl]-1-ethyl-5-methyl-1H-indole

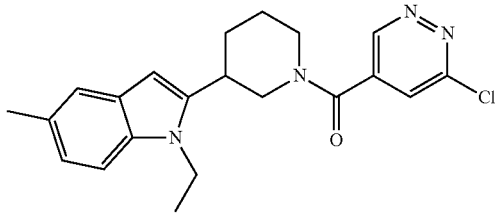 [SMILES: CCn1c(C2CCCN(C(=O)c3cnnc(Cl)c3)C2)cc2cc(C)ccc21]

Prepared as described for 2-{1-(6-chloropyridazine-4-carbonyl)piperidin-3-yl]-1-methyl-1H-indole (Intermediate 5) from 6-chloropyridazine-4-carboxylic acid (Intermediate 1; 104 mg, 0.655 mmol) and 1-ethyl-5-methyl-2-(piperidin-3-yl)-1H-indole hemi-formate salt (Intermediate 19; 156 mg, 0.596 mmol) with the exception that purification was carried out by column chromatography (silica gel) eluted with 0-100% EtOAc in petroleum ether 40-60 was used in place of solid phase extraction to afford the title compound.
MS ES+:383

Intermediate 29 5-Chloro-2-[1-(6-chloropyridazine-4-carbonyl)piperidin-3-yl]-1-ethyl-1H-indole

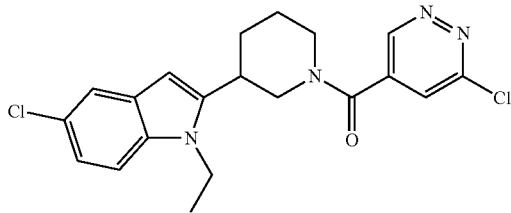 [SMILES: CCn1c(C2CCCN(C(=O)c3cnnc(Cl)c3)C2)cc2cc(Cl)ccc21]

Prepared as described for 2-{1-(6-chloropyridazine-4-carbonyl)piperidin-3-yl]-1-methyl-1H-indole (Intermediate 5) from 6-chloropyridazine-4-carboxylic acid (Intermediate 1; 93 mg, 0.585 mmol) and 5-chloro-1-ethyl-2-(piperidin-3-yl)-1H-indole hemi-formate salt (Intermediate 30; 150 mg, 0.532 mmol) with the exception that column chromatography (silica gel) eluted with 0-100% EtOAc in petroleum ether 40-60 was used in place of solid phase extraction to afford the title compound.
MS ES+:403

Intermediate 30 5-Chloro-1-ethyl-2-(piperidin-3-yl)-1H-indole hemi-formate

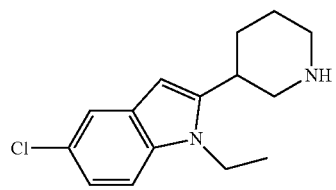 [SMILES: CCn1c(C2CCCNC2)cc2cc(Cl)ccc21]

To a stirred solution of 5-chloro-1-ethyl-2-(pyridin-3-yl)-1H-indole (Intermediate 31; 500 mg, 1.95 mmol) in absolute EtOH (25 mL) was added HCl (37%, 0.16 mL, 1.95 mmol). The reaction vessel was evacuated and back filled with nitrogen gas then platinum(IV) oxide (44 mg, 0.195 mmol) was added and the reaction vessel was evacuated and back filled with hydrogen gas. The reaction mixture was stirred at ambient temperature under a hydrogen atmosphere overnight. The reaction mixture was filtered through diatomaceous earth and concentrated in vacuo. The crude product was purified by reverse phase preparative HPLC eluted with acetonitrile/water (with 0.1% formic acid) to afford the title compound.
MS ES+:263

Intermediate 31 5-Chloro-1-ethyl-2-(pyridin-3-yl)-1H-indole

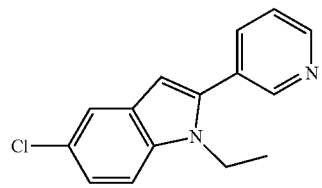 [SMILES: CCn1c(-c2cccnc2)cc2cc(Cl)ccc21]

To a stirred suspension of sodium hydride (60% dispersion in mineral oil, 490 mg, 12.73 mmol) in DMF (30 mL) at 0° C. was added a solution of 5-chloro-2-(pyridin-3-yl)-1H-indole (Intermediate 32; 1.94 g, 8.84 mmol) in DMF (20 mL) over 20 minutes. To the stirred mixture was added iodoethane (1.37 mL, 16.97 mmol). After 90 minutes the reaction mixture was allowed to warm to ambient temperature and was stirred for a further 3 hours. The reaction mixture was carefully poured onto ice/water and extracted into DCM. The combined organics were dried (Na₂SO₄), filtered and concentrated in vacuo to afford the title compound which was used in the next step without further purification.
MS ES+:257

Intermediate 32
5-Chloro-2-(pyridin-3-yl)-1H-indole

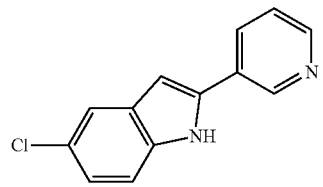 [SMILES: Clc1ccc2[nH]c(-c3cccnc3)cc2c1]

To a stirred solution of tert-butyl 5-chloro-2-(pyridin-3-yl)-1H-indole-1-carboxylate (Intermediate 33; 2.5 g, 7.604 mmol) and anisole (10 mL, 92.01 mmol) in DCM (75 mL) was added trifluoroacetic acid (15 mL, 196 mmol) and the reaction was stirred at ambient temperature under a nitrogen atmosphere overnight. The reaction mixture was concentrated in vacuo and the crude product was partitioned between EtOAc and saturated aqueous sodium bicarbonate solution. The organic phase was dried (Na₂SO₄), filtered and concentrated in vacuo and triturated with DCM to afford the title compound which was used in the next step without further purification.

MS ES+:229

Intermediate 33 tert-Butyl 5-chloro-2-(pyridin-3-yl)-1H-indole-1-carboxylate

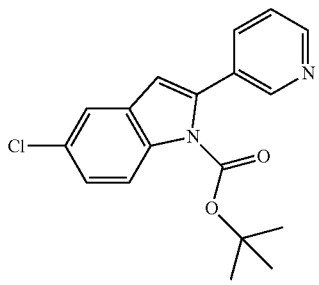 [SMILES: CC(C)(C)OC(=O)n1c(-c2cccnc2)cc2cc(Cl)ccc21]

To a stirred solution of 3-iodopyridine (3.15 g, 15.37 mmol) and {1-[(tert-butoxy)carbonyl]-5-chloro-1H-indol-2-yl}boronic acid (5.0 g, 16.92 mmol) in toluene (80 mL) and absolute EtOH (19 mL) under an atmosphere of nitrogen was added sodium carbonate solution (2 M, 23 mL, 46 mmol). The reaction mixture was degassed by bubbling nitrogen through it for 10 minutes then tetrakis(triphenylphosphine)palladium(0) (665 mg, 0.575 mmol) was added and the reaction mixture was heated at 90° C. for 3.5 hours. The reaction was allowed to cool to ambient temperature and was diluted in EtOAc and water. The organic phase was separated, washed with brine, dried (Na₂SO₄), filtered and concentrated in vacuo and purified by column chromatography (silica gel) eluted with 5-25% EtOAc in petroleum ether to afford the title compound.

MS ES+:329

Intermediate 34 2-[1-(6-Chloropyridazine-4-carbonyl)piperidin-3-yl]-3-methyl-1H-indole

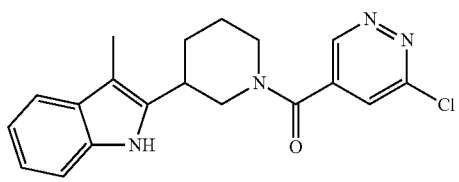 [SMILES: Cc1c(C2CCCN(C(=O)c3cnnc(Cl)c3)C2)[nH]c2ccccc12]

Prepared as described for 2-{1-(6-chloropyridazine-4-carbonyl)piperidin-3-yl]-1-methyl-1H-indole (Intermediate 5) from 6-chloropyridazine-4-carboxylic acid (Intermediate 1; 111 mg, 0.700 mmol) and 3-methyl-2-(piperidin-3-yl)-1H-indole (Intermediate 35; 150 mg, 0.700 mmol) with the exception that reverse phase preparative HPLC eluted with acetonitrile/water (with 0.1% ammonia) was used in place of solid phase extraction to afford the title compound.

MS ES+:355

Intermediate 35 3-Methyl-2-(piperidin-3-yl)-1H-indole

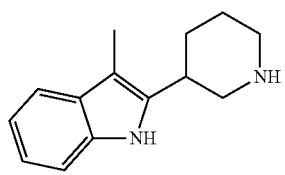 [SMILES: Cc1c(C2CCCNC2)[nH]c2ccccc12]

Prepared as described for 1-ethyl-5-methyl-2-(piperidin-3-yl)-1H-indole hemi-formate (Intermediate 19) from 3-methyl-2-(pyridin-3-yl)-1H-indole hydrochloride (Intermediate 26, 2 g, 8.2 mmol) and platinum(IV) oxide (0.4 g, 1.76 mmol) except that no HCl was added and the title compound was isolated by filtration and used without further purification.

MS ES+:215

Intermediate 36 tert-Butyl N-{4-[3-(1-ethyl-3-methyl-1H-indol-2-yl)piperidine-1-carbonyl]-1-methyl-1H-pyrazol-3-yl)carbamate

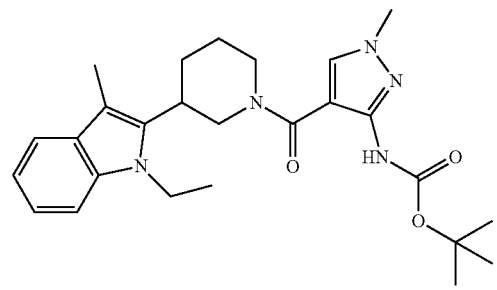 [SMILES: CCn1c(C2CCCN(C(=O)c3cn(C)nc3NC(=O)OC(C)(C)C)C2)c(C)c2ccccc21]

Prepared as described for 2-{1-(6-chloropyridazine-4-carbonyl)piperidin-3-yl]-1-methyl-1H-indole (Intermediate 5) from 1-ethyl-3-methyl-2-(piperidin-3-yl)-1H-indole hemi-formate salt (Intermediate 24; 132 mg, 0.502 mmol) and 3-{[(tert-butoxy)carbonyl]amino}1-1-methyl-1H-pyrazole-4-carboxylic acid (Intermediate 17; 0.133 g, 0.552 mmol) in dichloromethane (2 mL), except the work-up was performed as follows:

The reaction mixture was quenched by addition of saturated aqueous NaHCO₃ and the organic phase was separated using a phase separator cartridge. The aqueous phase was extracted with DCM and the combined organics were concentrated in vacuo to afford the title compound which was used without further purification.

MS ES+:466

Intermediate 37 tert-Butyl N-{4-[3-(1-ethyl-5-methyl-1H-indol-2-yl)piperidine-1-carbonyl]-1-methyl-1H-pyrazol-3-yl}carbamate

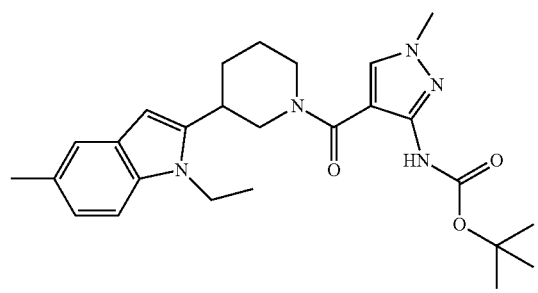 [SMILES: CCn1c(C2CCCN(C(=O)c3cn(C)nc3NC(=O)OC(C)(C)C)C2)cc2cc(C)ccc21]

Prepared as described for 2-{1-(6-chloropyridazine-4-carbonyl)piperidin-3-yl]-1-methyl-1H-indole (Intermediate 5) from 1-ethyl-5-methyl-2-(piperidin-3-yl)-1H-indole hemi-formate (Intermediate 19; 156 mg, 0.596 mmol) and 3-{[(tert-butoxy)carbonyl]amino}-1-methyl-1H-pyrazole-4-carboxylic acid (Intermediate 17; 0.158 g, 0.655 mmol) in dichloromethane (2 mL), except the work-up was performed as follows:

The reaction mixture was quenched by addition of saturated aqueous NaHCO$_3$ and the organic phase was separated using a phase separator cartridge. The aqueous phase was extracted with DCM and the combined organics were concentrated in vacuo to afford the title compound which was used without further purification.

MS ES$^+$:466

Intermediate 38 tert-Butyl N-{4-[3-(5-chloro-1-ethyl-1H-indol-2-yl)piperidine-1-carbonyl]-1-methyl-1H-pyrazol-3-yl)carbamate

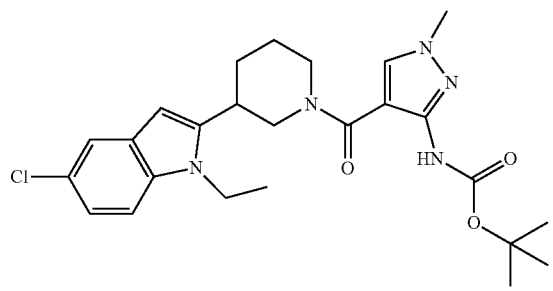 [SMILES: CCn1c(C2CCCN(C(=O)c3cn(C)nc3NC(=O)OC(C)(C)C)C2)cc2cc(Cl)ccc21]

Prepared as described for 2-{1-(6-chloropyridazine-4-carbonyl)piperidin-3-yl]-1-methyl-1H-indole (Intermediate 5) from 5-chloro-1-ethyl-2-(piperidin-3-yl)-1H-indole hemi-formate (Intermediate 30; 150 mg, 0.532 mmol) and 3-{[(tert-butoxy)carbonyl]amino}-1-methyl-1H-pyrazole-4-carboxylic acid (Intermediate 17; 0.141 g, 0.585 mmol) in dichloromethane (2 mL), except the work-up was performed as follows:

The reaction mixture was quenched by addition of saturated aqueous NaHCO$_3$ and the organic phase was separated using a phase separator cartridge. The aqueous phase was extracted with DCM and the combined organics were concentrated in vacuo to afford the title compound which was used without further purification.

MS ES$^+$:486

Intermediate 39 3-Chloro-5-[3-(5-chloro-3-methyl-pyridin-2-yl)piperidine-1-carbonyl]pyridazine

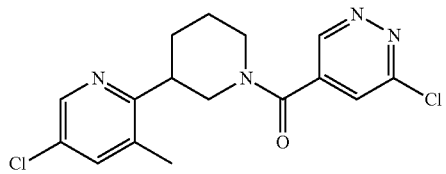 [SMILES: Cc1cc(Cl)cnc1C1CCCN(C(=O)c2cnnc(Cl)c2)C1]

Prepared as described for 2-{1-(6-chloropyridazine-4-carbonyl)piperidin-3-yl]-1-methyl-1H-indole (Intermediate 5) from 5-chloro-3-methyl-2-(piperidin-3-yl)pyridine (Intermediate 40; 0.09 g, 0.427 mmol) and 6-chloropyridazine-4-carboxylic acid (Intermediate 1; 74 mg, 0.470 mmol) in DCM (2 mL), except the work-up was performed as follows:

The reaction mixture was diluted in DCM, washed with saturated aqueous NaHCO$_3$ and the organic phase was separated using a phase separator cartridge and concentrated in vacuo and purified by column chromatography (silica gel) eluted with 0-50% EtOAc in petroleum ether 40-60 to afford the title compound.

MS ES$^+$:351

Intermediate 40 5-Chloro-3-methyl-2-(piperidin-3-yl)pyridine

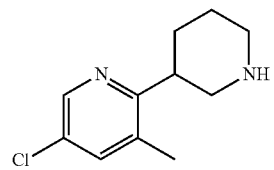

To a stirred solution of 2-(1-benzylpiperidin-3-yl)-5-chloro-3-methylpyridine (Intermediate 41; 0.14 g, 0.465 mmol) and triethylamine (0.097 ml, 0.698 mmol) in dichloromethane (3 mL) was added ACE-Cl (0.066 ml, 0.605 mmol) under a nitrogen atmosphere. The reaction was stirred at room temperature for 1 hour and was then concentrated in vacuo and the residue taken up in methanol and stirred for 1.5 hours then concentrated. The crude product was purified by column chromatography (basic silica) eluted with 0-10% ethyl acetate/methanol to afford the title compound.

MS ES$^+$:211

Intermediate 41 2-(1-Benzylpiperidin-3-yl)-5-chloro-3-methylpyridine

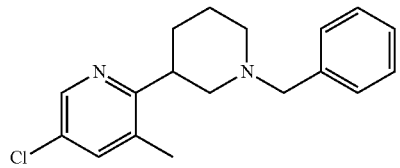 [SMILES: Cc1cc(Cl)cnc1C1CCCN(Cc2ccccc2)C1]

A flask charged with platinum(IV) oxide (0.016 g, 0.072 mmol) and 2-(1-benzyl-1,2,5,6-tetrahydropyridin-3-yl)-5-chloro-3-methylpyridine (Intermediate 42; 0.215 g, 0.720 mmol) was evacuated and purged with nitrogen three times. Ethanol (2 mL) and ethyl acetate (2 mL) were added under reduced pressure and hydrogen was introduced to the reaction vessel. The suspension was stirred under an atmosphere of hydrogen for 7 hours. The suspension was filtered through diatomaceous earth and the filtrate concentrated in vacuo to give the title compound which was used without further purification.

MS ES$^+$:301

Intermediate 42 2-(1-Benzyl-1,2,5,6-tetrahydropyridin-3-yl)-5-chloro-3-methylpyridine

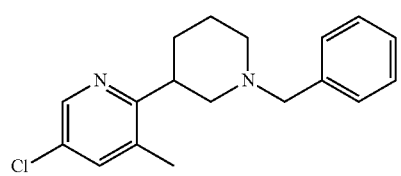 [SMILES: Cc1cc(Cl)cnc1C1CCCN(Cc2ccccc2)C1]

Prepared as described for 2-(1-benzyl-1,2,5,6-tetrahydropyridin-3-yl)-1-methyl-1H-indole (Intermediate 3) from 1-benzyl-5-(tetramethyl-1,3,2-dioxaborolan-2-yl)-1,2,3,6-tetrahydropyridine (CAS 1313738-80-5; 0.5 g, 1.671 mmol), 2-bromo-5-chloro-3-methylpyridine (CAS 65550-77-8; 0.380 g, 1.838 mmol), tetrakis-(triphenylphosphine)palladium(0) (0.097 g, 0.084 mmol) and potassium carbonate (0.693 g, 5.01 mmol) in 1,4-dioxane (10 mL) and water (2.5 mL) and irradiation in a microwave at 110° C. for 30 minutes. The workup was performed by diluting with ethyl acetate, washing with 2 M NaOH then saturated brine and purification by column chromatography (basic silica) eluted with 0-20% ethyl acetate/petroleum ether 40-60 to afford the title compound.

MS ES$^+$:299

Intermediate 43 5-Chloro-2-(3-methoxypiperidin-3-yl)-3-(trifluoromethyl) pyridine hydrochloride

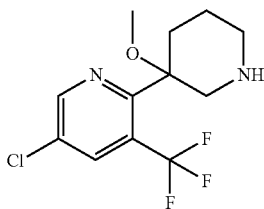 [SMILES: COC1(c2ncc(Cl)cc2C(F)(F)F)CCCNC1]

To a stirred solution of tert-butyl 3-[5-chloro-3-(trifluoromethyl)pyridin-2-yl]-3-methoxypiperidine-1-carboxylate (Intermediate 44; 0.1 g, 0.25 mmol) in 1,4-dioxane (1 mL) at 0° C. was added a solution of HCl in 1,4-dioxane (4.0 M, 1 mL, 4 mmol) in a dropwise fashion. After 10 minutes the reaction mixture was allowed to warm and was stirred at ambient temperature overnight. The reaction mixture was concentrated in vacuo and was triturated with diethyl ether to afford the title compound which was used in the next step without further purification.

MS ES$^+$:295

Intermediate 44 tert-Butyl 3-[5-chloro-3-(trifluoromethyl)pyridin-2-yl]-3-methoxypiperidine-1-carboxylate

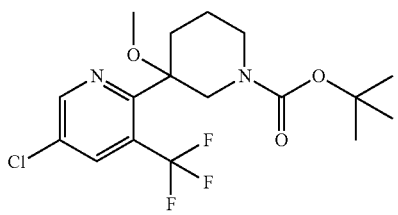 [SMILES: COC1(c2ncc(Cl)cc2C(F)(F)F)CCCN(C(=O)OC(C)(C)C)C1]

To a stirred solution of tert-butyl 3-[5-chloro-3-(trifluoromethyl)pyridin-2-yl]-3-hydroxypiperidine-1-carboxylate (Intermediate 45; 1.4 g, 3.68 mmol) in THF (20 mL) at 0° C. was added sodium hydride (60% dispersion in mineral oil, 0.22 g, 3.5 mmol) in portions over 15 minutes. To the reaction mixture was added iodomethane (0.78 g, 5.5 mmol) and the reaction mixture was allowed to warm to ambient temperature and was stirred overnight. The reaction was diluted in water and extracted into EtOAc, dried (Na$_2$SO$_4$), filtered and concentrated in vacuo and purified by column chromatography (silica gel) eluted with 20% EtOAc in hexane to afford the title compound.

MS ES$^+$:339 [M—butyl]H$^+$

Intermediate 45 tert-Butyl 3-[5-chloro-3-(trifluoromethyl)pyridin-2-yl]-3-hydroxypiperidine-1-carboxylate

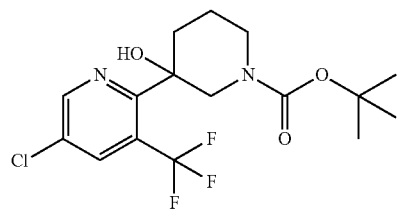 [SMILES: CC(C)(C)OC(=O)N1CCCC(O)(c2ncc(Cl)cc2C(F)(F)F)C1]

To a stirred solution of 2-bromo-5-chloro-3-(trifluoromethyl)pyridine (Intermediate 46; 11.4 g, 43.8 mmol) in toluene (230 mL) at −78° C. under a nitrogen atmosphere was added n-butyllithium in hexanes solution (2.5M, 19.3 mL, 48.2 mmol) dropwise over 20 minutes. After 15-20 mins a solution of tert-butyl 3-oxopiperidine-1-carboxylate (CAS 98977-36-7, 9.6 g, 48.1 mmol) in toluene (50 mL) was added over 5 minutes. The solution was stirred at −78° C. for 45 minutes and was then allowed to warm to ambient temperature for 1 hour. The solvent was removed in vacuo and the crude product was taken up in EtOAc and water. The organic phase was removed and the aqueous phase was extracted with EtOAc and the combined organics were washed with water and brine, dried (Na$_2$SO$_4$), filtered and concentrated in vacuo and purified by column chromatography (silica gel) eluted with 0.2% MeOH/DCM to afford the title compound after triturating with hexanes.

MS ES$^+$:325 [M—butyl]H$^+$

Intermediate 46
2-Bromo-5-chloro-3-(trifluoromethyl)pyridine

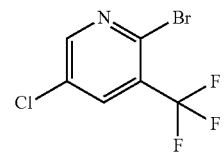 [SMILES: FC(F)(F)c1cc(Cl)cnc1Br]

To a stirred solution of 5-chloro-3-(trifluoromethyl)pyridin-2-amine (Intermediate 47; CAS 79456-33-0, 10 g, 50.9 mmol) in aqueous HBr (48%, 56.7 g, 336 mmol) at −10° C. was added bromine (23.6 g, 147.5 mmol) dropwise over 20 minutes, followed by a solution of sodium nitrite (10.2 g, 147.8 mmol) in water (18 mL). The reaction was stirred at ambient temperature for 2 hours and was basified (pH 9-10) and extracted into diethyl ether. The organic was washed with brine, dried (Na$_2$SO$_4$), filtered and concentrated in vacuo to afford the title compound without further purification.

MS ES$^+$:262

Intermediate 47
5-Chloro-3-(trifluoromethyl)pyridin-2-amine

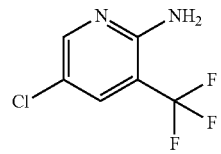 [SMILES: Nc1ncc(Cl)cc1C(F)(F)F]

To a stirred solution of 3-(trifluoromethyl)pyridin-2-amine (CAS 183610-70-0, 25 g, 154 mmol) in DMF (200 mL) under a nitrogen atmosphere was added N-chlorosuccinimide (21.63 g, 162 mmol) in portions. The reaction mixture was heated to 60° C. for 1 hour. The reaction was allowed to cool to ambient temperature and was concentrated in vacuo, re-dissolved in DCM and passed through a pad of silica gel. The DCM was removed in vacuo and the crude product was taken up in diethyl ether, washed with water then brine, dried ($Na_2SO_4$), filtered and concentrated in vacuo to afford the title compound without further purification.
MS $ES^+$:197

Intermediate 48 3-Chloro-5-{3-[5-chloro-3-(trifluoromethyl)pyridin-2-yl]-3-methoxypiperidine-1-carbonyl}pyridazine

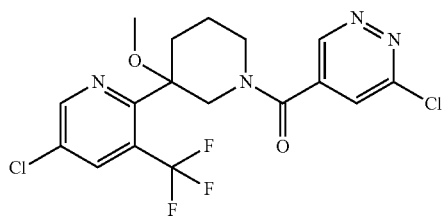 [SMILES: COC1(c2ncc(Cl)cc2C(F)(F)F)CCCN(C(=O)c2cnnc(Cl)c2)C1]

Prepared as described for 2-{1-(6-chloropyridazine-4-carbonyl)piperidin-3-yl]-1-methyl-1H-indole (Intermediate 5) from 5-chloro-2-(3-methoxypiperidin-3-yl)-3-(trifluoromethyl)pyridine hydrochloride (Intermediate 43; 132 mg, 0.400 mmol) and 6-chloropyridazine-4-carboxylic acid (Intermediate 1; 76 mg, 0.480 mmol) in dichloromethane (1.5 mL), except the work-up was performed as follows: The reaction mixture was quenched by addition of saturated aqueous $NaHCO_3$ and the aqueous was extracted into DCM. The combined organics were concentrated in vacuo to afford the title compound which was used without further purification.
MS $ES^+$:435

Intermediate 49 5-Chloro-2-(3-methoxypiperidin-3-yl)-3-methylpyridine hydrochloride

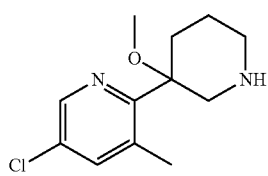 [SMILES: COC1(c2ncc(Cl)cc2C)CCCNC1]

Prepared as described for 5-chloro-2-(3-methoxypiperidin-3-yl)-3-(trifluoromethyl)pyridine hydrochloride (Intermediate 43) from tert-butyl 3-(5-chloro-3-methylpyridin-2-yl)-3-methoxypiperidine-1-carboxylate (Intermediate 50; 820 mg, 2.41 mmol) in 1,4-dioxane (25 mL) using HCl in 1,4-dioxane solution (4.0 M, 35 mL, 337.4 mmol) to afford the title compound.
MS $ES^+$:241

Intermediate 50 tert-Butyl 3-(5-chloro-3-methylpyridin-2-yl)-3-methoxypiperidine-1-carboxylate

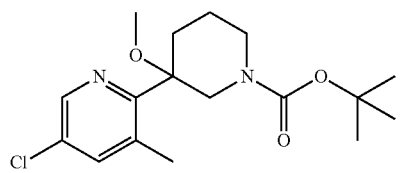 [SMILES: COC1(c2ncc(Cl)cc2C)CCCN(C(=O)OC(C)(C)C)C1]

Prepared as described for tert-butyl 3-[5-chloro-3-(trifluoromethyl)pyridin-2-yl]-3-methoxypiperidine-1-carboxylate (Intermediate 44) from tert-butyl 3-(5-chloro-3-methylpyridin-2-yl)-3-hydroxypiperidine-1-carboxylate (Intermediate 51; 2.0 g, 6.132 mmol) in THF (140 mL) using sodium hydride (60% dispersion in mineral oil, 1.1 g, 27.6 mmol) and iodomethane (1.7 mL, 27.6 mmol). The crude product was purified by column chromatography (silica gel) eluted with 2-5% EtOAc/petroleum ether to afford the title compound.
MS $ES^+$:341

Intermediate 51 tert-Butyl 3-(5-chloro-3-methylpyridin-2-yl)-3-hydroxypiperidine-1-carboxylate

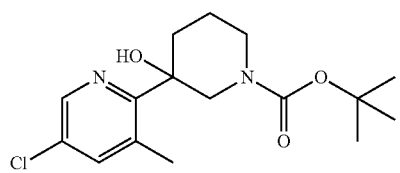 [SMILES: Cc1cc(Cl)cnc1C1(O)CCCN(C(=O)OC(C)(C)C)C1]

To a stirred solution of 2-bromo-5-chloro-3-methylpyridine (CAS 65550-77-8, 19.0 g, 92.0 mmol) in diethyl ether (350 mL) at −70° C. under a nitrogen atmosphere was added n-butyllithium in hexanes solution (2.5M, 40.5 mL, 101.2 mmol) dropwise over 20 minutes. After 90 minutes a solution of tert-butyl 3-oxopiperidine-1-carboxylate (CAS 98977-36-7, 20.2 g, 101.2 mmol) in diethyl ether (100 mL) was added dropwise over 25 minutes. The solution was stirred at −70° C. for 2 hours and was then allowed to warm to ambient temperature and was stirred overnight. The reaction mixture was quenched with saturated aqueous $NH_4Cl$ and was extracted with diethyl ether. The combined organics were dried ($Na_2SO_4$), filtered and concentrated in vacuo and purified by column chromatography (silica gel) eluted with 2-8% EtOAc/toluene to afford the title compound.
MS $ES^+$:327

Intermediate 52 5-Chloro-2-(3-fluoropiperidin-3-yl)-3-methylpyridine hydrochloride

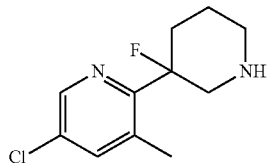

Prepared as described for 5-chloro-2-(3-methoxypiperidin-3-yl)-3-(trifluoromethyl)pyridine hydrochloride (Intermediate 43) from tert-butyl 3-(5-chloro-3-methylpyridin-2-yl)-3-fluoropiperidine-1-carboxylate (Intermediate 53; 620 mg, 1.89 mmol) in 1,4-dioxane (25 mL) using HCl in 1,4-dioxane solution (4.0 M, 35 mL, 337.4 mmol) to afford the title compound.
MS ES+:229

Intermediate 53 tert-Butyl 3-(5-chloro-3-methyl-pyridin-2-yl)-3-fluoropiperidine-1-carboxylate

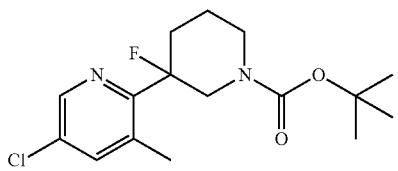 [SMILES: Cc1cc(Cl)cnc1C1(F)CCCN(C(=O)OC(C)(C)C)C1]

To a stirred solution of tert-butyl 3-(5-chloro-3-methyl-pyridin-2-yl)-3-hydroxypiperidine-1-carboxylate (Intermediate 51; 5.0 g, 15.33 mmol) in DCM (250 mL) at −78° C. under a nitrogen atmosphere was added N,N-diethylamino-suflur trifluoride (6.1 mL, 45.99 mmol) dropwise. The temperature was maintained at −70° C. for 5.5 hours and the reaction was quenched with MeOH and water. The organic phase was separated, washed with brine, dried (Na$_2$SO$_4$), filtered and concentrated in vacuo and then purified by column chromatography (silica gel) eluted with 5% EtOAc/toluene to afford the title compound.
MS ES+:273 [M—butyl]H+

Intermediate 54 3-Chloro-5-[3-(5-chloro-3-methyl-pyridin-2-yl)-3-methoxypiperidine-1-carbonyl]pyridazine

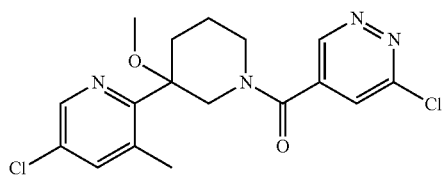 [SMILES: COC1(c2ncc(Cl)cc2C)CCCN(C(=O)c2cnnc(Cl)c2)C1]

Prepared as described for 2-{1-(6-chloropyridazine-4-carbonyl)piperidin-3-yl]-1-methyl-1H-indole (Intermediate 5) from 5-chloro-2-(3-methoxypiperidin-3-yl)-3-methyl-pyridine hydrochloride (Intermediate 49; 100 mg, 0.361 mmol) and 6-chloropyridazine-4-carboxylic acid (Intermediate 1; 86 mg, 0.541 mmol) in dichloromethane (2 mL), except the work-up was performed as follows:

The reaction mixture was quenched by addition of saturated aqueous NaHCO$_3$ and the aqueous was extracted into DCM. The combined organics were concentrated in vacuo to afford the title compound which was used without further purification.
MS ES+:381

Intermediate 55 3-Chloro-5-{[3-(5-chloro-3-methyl-pyridin-2-yl)-3-fluoropiperidin-1-yl]carbonyl}pyridazine

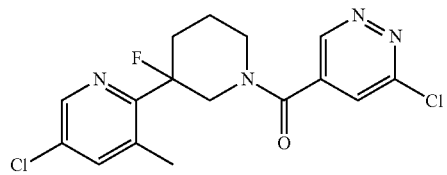 [SMILES: Cc1cc(Cl)cnc1C1(F)CCCN(C(=O)c2cnnc(Cl)c2)C1]

Prepared as described for 2-{1-(6-chloropyridazine-4-carbonyl)piperidin-3-yl]-1-methyl-1H-indole (Intermediate 5) from 5-chloro-2-(3-fluoropiperidin-3-yl)-3-methylpyridine hydrochloride (Intermediate 52; 100 mg, 0.377 mmol) and 6-chloropyridazine-4-carboxylic acid (Intermediate 1; 90 mg, 0.566 mmol) in dichloromethane (2 mL), except the work-up was performed as follows:

The reaction mixture was quenched by addition of saturated aqueous NaHCO$_3$ and the aqueous was extracted into DCM. The combined organics were concentrated in vacuo to afford the title compound which was used without further purification.
MS ES+:369

Intermediate 56 tert-Butyl N-{4-[3-(5-chloro-3-methylpyridin-2-yl)-3-methoxypiperidine-1-carbonyl]-1-methyl-1H-pyrazol-3-yl}carbamate

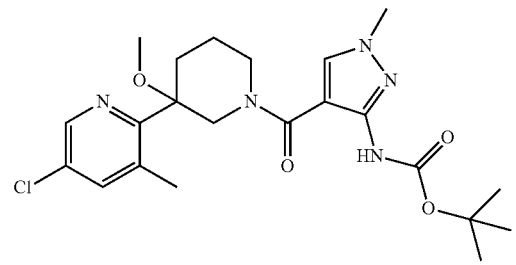 [SMILES: COC1(c2ncc(Cl)cc2C)CCCN(C(=O)c2cn(C)nc2NC(=O)OC(C)(C)C)C1]

Prepared as described for 2-{1-(6-chloropyridazine-4-carbonyl)piperidin-3-yl]-1-methyl-1H-indole (Intermediate 5) from 5-chloro-2-(3-methoxypiperidin-3-yl)-3-methyl-pyridine hydrochloride (Intermediate 49; 50 mg, 0.180 mmol) and 3-{[tert-butoxy)carbonyl]amino}1-1-methyl-1H-pyrazole-4-carboxylic acid (Intermediate 17; 0.057 g, 0.234 mmol) in dichloromethane (1 mL), except the work-up was performed as follows: The reaction mixture was quenched by addition of saturated aqueous NaHCO$_3$ and the aqueous was extracted into DCM. The combined organics were concentrated in vacuo to afford the title compound which was used without further purification.
MS ES+:464

Intermediate 57 tert-Butyl N-{4-[3-(5-chloro-3-methylpyridin-2-yl)-3-fluoropiperidin-1-carbonyl]-1-methyl-1H-pyrazol-3-yl}carbamate

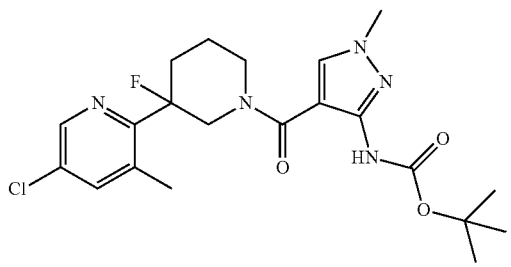 [SMILES: Cc1cc(Cl)cnc1C1(F)CCCN(C(=O)c2cn(C)nc2NC(=O)OC(C)(C)C)C1]

Prepared as described for 2-{1-(6-chloropyridazine-4-carbonyl)piperidin-3-yl]-1-methyl-1H-indole (Intermediate 5) from 5-chloro-2-(3-fluoropiperidin-3-yl)-3-methylpyridine hydrochloride (Intermediate 52; 50 mg, 0.189 mmol) and 3-{[tert-butoxy)carbonyl]amino}-1-methyl-1H-pyrazole-4-carboxylic acid (Intermediate 17; 0.059 g, 0.245 mmol) in dichloromethane (1 mL), except the work-up was performed as follows:

The reaction mixture was quenched by addition of saturated aqueous $NaHCO_3$ and the aqueous was extracted into DCM. The combined organics were concentrated in vacuo to afford the title compound which was used without further purification.

MS $ES^+$:452

2. EXAMPLES

Example 1

N,N-Dimethyl-4-{3-[1-(propan-2-yl)-1H-1,3-benzodiazol-2-yl]piperidin-1-carbonyl}pyridin-2-amine (racemic)

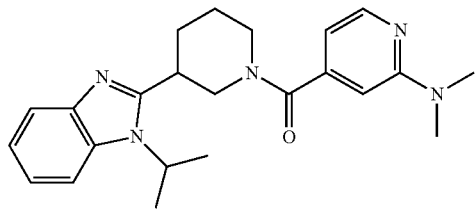 [SMILES: CC(C)n1c(C2CCCN(C(=O)c3ccnc(N(C)C)c3)C2)nc2ccccc21]

To a stirred suspension of 2-(dimethylamino)pyridine-4-carboxylic acid (100 mg, 0.602 mmol), 2-(piperidin-3-yl)-1-(propan-2-yl)-1H-1,3-benzodiazole dihydrochloride (CAS 1185300-76-8, 190 mg, 0.602 mmol) and triethylamine (0.335 ml, 2.407 mmol) in DCM (6 mL) was added 2,4,6-tripropyl-1,3,5,2,4,6-trioxatriphosphinane 2,4,6-trioxide (50 wt. % solution in EtOAc) (0.791 ml, 0.903 mmol). The reaction was stirred at ambient temperature overnight. The reaction mixture was diluted with DCM, washed with water and the solvent was removed in vacuo. The crude product was purified by column chromatography (silica gel) eluted with 0-100% ethyl acetate in petroleum ether 40-60 to afford the title compound.

$^1$H NMR (400 MHz, DMSO-$d_6$) δ ppm 1.11-1.56 (m, 3H) 1.57-2.18 (m, 7H) 2.82-3.31 (m, 9H) 3.46-3.68 (m, 1H) 4.34-5.00 (m, 2H) 6.40-6.67 (m, 2H) 7.04-7.25 (m, 2H) 7.46-7.76 (m, 2H) 8.03-8.24 (m, 1H)

MS $ES^+$:392

Example 2

N,N-Dimethyl-4-{3-[1-(propan-2-yl)-1H-1,3-benzodiazol-2-yl]piperidine-1-carbonyl}pyridin-2-amine (enantiomer 1)

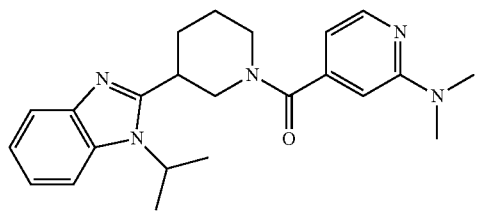 [SMILES: CC(C)n1c(C2CCCN(C(=O)c3ccnc(N(C)C)c3)C2)nc2ccccc21]

Chiral separation of N,N-dimethyl-4-{3-[1-(propan-2-yl)-1H-1,3-benzodiazol-2-yl]piperidin-1carbonyl}pyridin-2-amine (racemic) (Example 1) was performed using chiral SFC (Waters system fitted with Chiralpak AD-H column (10×250 mm, 5 μm Daicel); 100 mbar $CO_2$ with 26% EtOH; 40° C.) to afford the title compound as the first eluting compound.

MS $ES^+$:392

Chiral SFC (Jasco system fitted with Chiralpak AD-H (4.6×100 mm, 5 μm Daicel); 100 mbar $CO_2$ with 26% EtOH; 40° C.) Rt=2.6 mins

Example 3

N,N-Dimethyl-4-{3-[1-(propan-2-yl)-1H-1,3-benzodiazol-2-yl]piperidine-1-carbonyl}pyridin-2-amine (enantiomer 2)

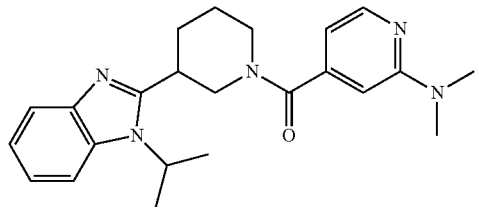 [SMILES: CC(C)n1c(C2CCCN(C(=O)c3ccnc(N(C)C)c3)C2)nc2ccccc21]

Chiral separation of N,N-dimethyl-4-{3-[1-(propan-2-yl)-1H-1,3-benzodiazol-2-yl]piperidin-1carbonyl}pyridin-2-amine (racemic) (Example 1) was performed using chiral SFC (Waters system fitted with Chiralpak AD-H column (10×250 mm, 5 μm Daicel); 100 mbar $CO_2$ with 26% EtOH; 40° C.) to afford the title compound as the second eluting compound.

MS $ES^+$:392

Chiral SFC (Jasco system fitted with Chiralpak AD-H (4.6×100 mm, 5 μm Daicel); 100 mbar $CO_2$ with 26% EtOH; 40° C.) Rt=6.75 mins

Example 4

N,N-Dimethyl-4-[3-(1-methyl-1H-1,3-benzodiazol-2-yl)piperidine-1-carbonyl]pyridin-2-amine

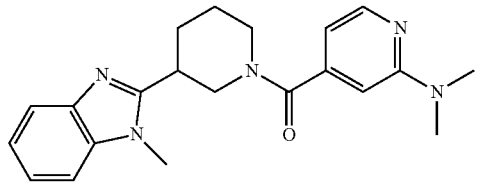 [SMILES: CN(C)c1cc(C(=O)N2CCCC(c3nc4ccccc4n3C)C2)ccn1]

To a stirred solution of 1-methyl-2-(piperidin-3-yl)-1H-1,3-benzodiazole (CAS 013-81-2, 50 mg, 0.232 mmol) dissolved in DCM (10 mL) was added 2-(dimethylamino)pyridine-4-carboxylic acid (CAS 77314-81-9, 38.6 mg, 0.232 mmol) followed by HOAt (37.9 mg, 0.279 mmol), EDC (53.4 mg, 0.279 mmol) and triethylamine (0.162 ml, 1.161 mmol). The reaction mixture was stirred at ambient temperature for 17 hours. Saturated sodium bicarbonate solution (10 mL) was added and the mixture was stirred for 30 minutes after which time the phases were separated using a phase separator cartridge. The organics were concentrated under vacuum and the residue was dissolved in DMSO and purified by preparative HPLC to afford the title compound.

$^1$H NMR (400 MHz, DCM-d$_2$) δ ppm 1.66-2.28 (m, 4H) 2.90-3.24 (m, 8H) 3.45-3.94 (m, 5H) 4.52-4.91 (m, 1H) 6.39-6.60 (m, 2H) 7.11-7.47 (m, 3H) 7.56-7.75 (m, 1H) 8.05-8.28 (m, 1H)

MS ES$^+$:364

Example 5

2-[1-(6-Chloropyridazine-4-carbonyl)piperidin-3-yl]-1-(propan-2-yl)-1H-1,3-benzodiazole

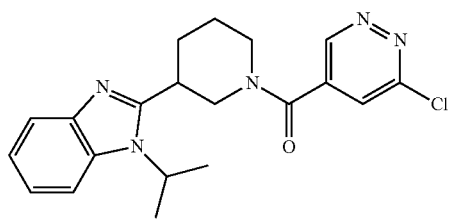

Prepared as described for N,N-dimethyl-4-{3-[1-(propan-2-yl)-1H-1,3-benzodiazol-2-yl]piperidin-1-carbonyl}pyridin-2-amine (Example 1) from 2-(piperidin-3-yl)-1-(propan-2-yl)-1H-1,3-benzodiazole dihydrochloride (CAS 1185300-76-8, 229 mg, 0.724 mmol) and 6-chloropyridazine-4-carboxylic acid (Intermediate 1; 130 mg, 0.820 mmol) and the reaction was quenched with saturated aqueous NaHCO$_3$ and the organic layer was filtered through a phase separation cartridge and evaporated to dryness. The crude product was purified using column chromatography (silica gel) eluted with 20-100% ethyl acetate in petroleum ether 40-60 then 0-20% methanol in ethyl acetate to afford the title compound.

$^1$H NMR (400 MHz, DMSO-d$_6$) δ ppm 1.11-2.17 (m, 10H) 3.03-3.62 (obscured m, 3H) 4.03 (m, 1H) 4.21-4.93 (m, 2H) 7.03-7.26 (m, 2H) 7.51-7.76 (m, 2H) 8.01-8.18 (m, 1H) 9.29-9.44 (m, 1H)

MS ES$^+$:384

Example 6

N-Methyl-5-{3-[1-(propan-2-yl)-1H-1,3-benzodiazol-2-yl]piperidine-1-carbonyl}pyridazin-3-amine

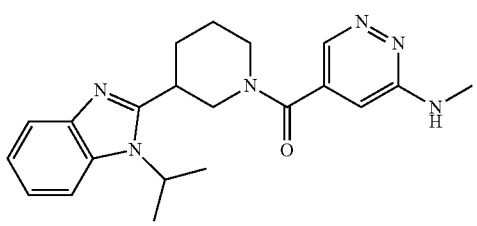 [SMILES: CNc1cc(C(=O)N2CCCC(c3nc4ccccc4n3C(C)C)C2)cnn1]

2-[1-(6-Chloropyridazine-4carbonyl)piperidin-3-yl}-1-(propan-2-yl)-1H-1,3-benzodiazole (Example 5) (161 mg, 0.419 mmol) was dissolved in methanamine solution (33% in ethanol, 1.97 g, 20.97 mmol) and was irradiated in a microwave reactor at 150° C. for 1 hour. The volatile components were removed in vacuo and the crude product was purified using column chromatography (silica gel) eluted with 20-100% ethyl acetate in petroleum ether 40-60 then 0-40% methanol in ethyl acetate to afford the title compound.

$^1$H NMR (400 MHz, DMSO-d$_6$) δ ppm 1.26-2.17 (m, 10H) 2.70-2.93 (m, 3H) 2.94-3.66 (obscured m, 3H) 4.02-4.14 (m, 1H) 4.33-4.98 (m, 2H) 6.79 (br. s., 1H) 6.91-7.23 (m, 3H) 7.50-7.76 (m, 2H) 8.38-8.77 (m, 1H)

MS ES$^+$:379

Example 7

2-[1-(1-Ethyl-1H-pyrazole-4-carbonyl)piperidin-3-yl]-1-(propan-2-yl)-1H-1,3-benzodiazole

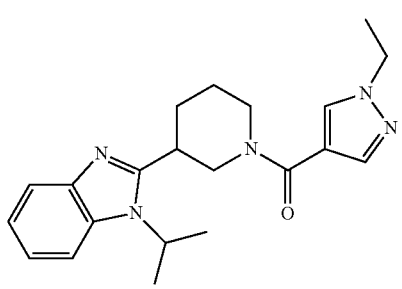 [SMILES: CCn1cc(C(=O)N2CCCC(c3nc4ccccc4n3C(C)C)C2)cn1]

Prepared as described for N,N-dimethyl-4-{3-[1-(propan-2-yl)-1H-1,3-benzodiazol-2-yl]piperidin-1-carbonyl}pyridin-2-amine (Example 1) from 2-(piperidin-3-yl)-1-(propan-2-yl)-1H-1,3-benzodiazole dihydrochloride (CAS 1185300-76-8, 0.15 g, 0.474 mmol) and 1-ethyl-1H-pyrazole-4-carboxylic acid (CAS 400858-54-0, 0.073 g, 0.522 mmol). The reaction was diluted with DCM and quenched with saturated aqueous NaHCO$_3$ and the organic layer was filtered through a phase separation cartridge and evaporated to dryness. The crude product was purified by column chromatography (silica gel) eluted with 0-10% methanol in DCM to afford the title compound.

$^1$H NMR (400 MHz, DMSO-d$_6$) δ ppm 1.38 (t, J=7.33 Hz, 3H) 1.47-1.75 (m, 7H) 1.79-2.16 (m, 3H) 2.86-3.19 (obscured m, 3H) 4.15 (q, J=7.07 Hz, 2H) 4.21-4.62 (m, 2H) 4.82 (br. s., 1H) 7.09-7.22 (m, 2H) 7.53-7.61 (m, 1H) 7.63-7.72 (m, 2H) 8.05 (s, 1H)
MS ES+:366

Example 8

N,N-Dimethyl-4-[3-(1-methyl-1H-indol-2-yl)piperidine-1-carbonyl]pyridin-2-amine

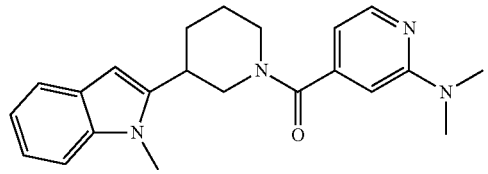 [SMILES: CN(C)c1cc(C(=O)N2CCCC(c3cc4ccccc4n3C)C2)ccn1]

To a stirred solution of 1-methyl-2-(piperidin-3-yl)-1H-indole (Intermediate 2; 0.02 g, 0.093 mmol) and 2-(dimethylamino)pyridine-4-carboxylic acid hydrochloride (0.023 g, 0.112 mmol) in DCM (1 mL) was added triethylamine (0.026 ml, 0.187 mmol) and then 2,4,6-tripropyl-1,3,5,2,4,6-trioxatriphosphinane 2,4,6-trioxide (50 wt. % solution in EtOAc) (0.139 ml, 0.233 mmol). The reaction mixture was stirred at room temperature. After 80 mins the reaction was quenched with saturated aqueous NaHCO$_3$ and was extracted into DCM. The crude product was purified by reverse phase preparative HPLC eluted with acetonitrile/water (with 0.1% ammonia) to afford the title compound.

$^1$H NMR (400 MHz, CD$_3$CN) δ ppm 1.52-2.00 (m, 4H) 2.75-3.22 (m, 9H) 3.37-3.88 (m, 4H) 4.46-4.85 (m, 1H) 6.21-6.65 (m, 3H) 6.94-7.61 (m, 4H) 8.06-8.24 (m, 1H)
MS ES+:363

Example 9

N-Methyl-5-[3-(1-methyl-1H-indol-2-yl)piperidine-1-carbonyl]pyridazin-3-amine

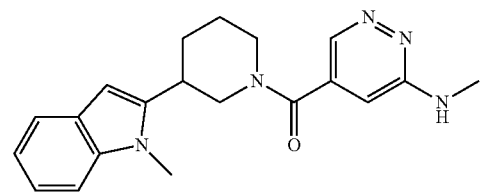 [SMILES: CNc1cc(C(=O)N2CCCC(c3cc4ccccc4n3C)C2)cnn1]

To a microwave vial charged with 2-{1-(6-chloropyridazine-4-carbonyl)piperidin-3-yl]-1-methyl-1H-indole (Intermediate 5; 0.037 g, 0.104 mmol) in 1,4-dioxane (2 mL) was added methanamine [2M solution in THF] (1.043 ml, 2.085 mmol). The vial was sealed and irradiated in the microwave at 140° C. for 5 hours and 20 minutes. Additional methanamine [2M solution in THF] (1.043 ml, 2.085 mmol) and NMP (1 mL) [to aid microwave absorption] were added and the reaction irradiated in the microwave at 160° C. for 1 hour. The volatile components were removed in vacuo and the crude product was purified by reverse phase preparative HPLC eluted with acetonitrile/water (with 0.1% ammonia) to afford the title compound.

$^1$H NMR (400 MHz, CD$_3$CN) δ ppm 1.53-1.93 (m, 4H) 2.79-3.32 (m, 6H) 3.45-3.86 (m, 4H) 4.42-4.80 (m, 1H) 5.43-5.59 (m, 1H) 6.28-6.36 (m, 1H) 6.60-6.73 (m, 1H) 6.94-7.11 (m, 1H) 7.11-7.24 (m, 1H) 7.25-7.43 (m, 1H) 7.45-7.60 (m, 1H) 8.44-8.49 (m, 1H)
MS ES+:350

Example 10

4-[3-(1-Ethyl-1H-indol-2-yl)piperidine-1-carbonyl]-N,N-dimethylpyridin-2-amine

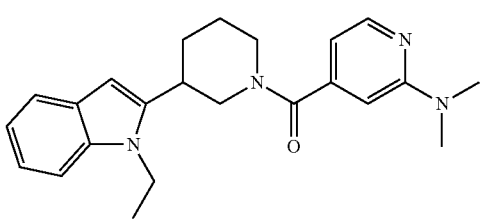 [SMILES: CCn1c(C2CCCN(C(=O)c3ccnc(N(C)C)c3)C2)cc2ccccc21]

Prepared as described for N,N-dimethyl-4-[3-(1-methyl-1H-indol-2-yl)piperidine-1-carbonyl]pyridin-2-amine (Example 8) from 2-(dimethylamino)pyridine-4-carboxylic acid hydrochloride (0.040 g, 0.197 mmol) and 1-ethyl-2-(piperidin-3-yl)-1H-indole (Intermediate 6; 0.045 g, 0.197 mmol). The reaction was quenched by addition of saturated aqueous NaHCO$_3$, extracted with EtOAc and washed with saturated aqueous NaHCO$_3$ then brine. The crude product was purified by reverse phase preparative HPLC eluted with acetonitrile/water (with 0.1% ammonia) to afford the title compound.

$^1$H NMR (400 MHz, CDCl$_3$) δ ppm 1.07-1.51 (m, 3H) 1.55-1.98 (m, 3H) 2.07-2.31 (m, 1H) 2.66-3.20 (m, 9H) 3.72-4.04 (m, 2H) 4.25-4.42 (m, 1H) 4.65-5.01 (m, 1H) 6.21-6.38 (m, 1H) 6.41-6.62 (m, 2H) 6.95-7.42 (m, 3H) 7.47-7.68 (m, 1H) 8.22 (dd, J=19.71, 4.80 Hz, 1H)
MS ES+:377

Example 11

5-[3-(1-Ethyl-1H-indol-2-yl)piperidine-1-carbonyl]-N,N-dimethylpyridazin-3-amine

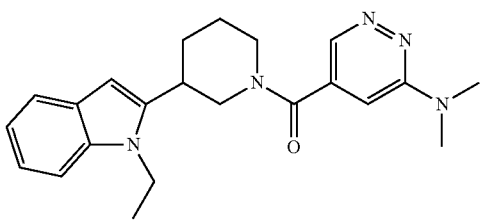 [SMILES: CCn1c(C2CCCN(C(=O)c3cnnc(N(C)C)c3)C2)cc2ccccc21]

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-ethyl-1H-indole (Intermediate 10; 0.042 g, 0.114 mmol) and dimethylamine [2.0M solution in THF] (1.139 ml, 2.277 mmol) using NMP (1 mL) as the solvent. The reaction mixture was irradiated in the microwave at 140° C. for 20 minutes to afford the title compound after purification by reverse phase preparative HPLC eluted with acetonitrile/water (with 0.1% ammonia).

$^1$H NMR (400 MHz, DMSO-d$_6$) δ ppm 0.87-1.40 (m, 3H) 1.59-1.96 (m, 3H) 2.04-2.15 (m, 1H) 2.75-2.97 (m, 1H)

2.99-3.25 (m, 8H) 3.51 (m, 1H) 3.90-4.09 (m, 1H) 4.27 (m, 1H) 4.42-4.72 (m, 1H) 6.17-6.39 (m, 1H) 6.86-7.16 (m, 3H) 7.29-7.54 (m, 2H) 8.54 (s, 1H)

MS ES+: m/z 378

Example 12

5-[3-(1-Ethyl-1H-indol-2-yl)piperidine-1-carbonyl]-N-methylpyridazin-3-amine

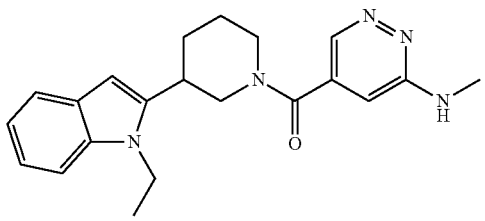 [SMILES: CCn1c(C2CCCN(C(=O)c3cnnc(NC)c3)C2)cc2ccccc21]

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-ethyl-1H-indole (Intermediate 10; 0.042 g, 0.114 mmol) and methanamine [2M solution in THF] (2.278 ml, 4.556 mmol) using NMP (1 mL) as the solvent and irradiated in the microwave at 140° C. for 2 hours 20 minutes to afford the title compound after purification by reverse phase preparative HPLC eluted with acetonitrile/water (with 0.1% ammonia).

$^1$H NMR (400 MHz, DMSO-$d_6$) δ ppm 0.91-1.39 (m, 3H) 1.56-1.95 (m, 3H) 1.99-2.18 (m, 1H) 2.74-2.93 (m, 4H) 2.97-3.12 (m, 1H) 3.12-3.26 (m, 1H) 3.46-3.61 (m, 1H) 3.91-4.10 (m, 1H) 4.16-4.33 (m, 1H) 4.43-4.69 (m, 1H) 6.17-6.38 (m, 1H) 6.69-6.83 (m, 1H) 6.90-7.17 (m, 3H) 7.28-7.56 (m, 2H) 8.49 (d, J=7.07 Hz, 1H)

MS ES+:364

Example 13

N,N-Dimethyl-5-{3-[1-(propan-2-yl)-1H-indol-2-yl]piperidine-1-carbonyl}pyridazin-3-amine

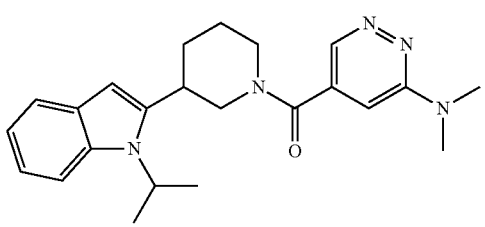 [SMILES: CC(C)n1c(C2CCCN(C(=O)c3cnnc(N(C)C)c3)C2)cc2ccccc21]

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-(propan-2-yl)-1H-indole (Intermediate 11; 0.065 g, 0.170 mmol) and dimethylamine [2.0M solution in THF] (1.698 ml, 3.40 mmol) using NMP (1 mL) as the solvent. The reaction mixture was irradiated in the microwave at 140° C. for 20 minutes to afford the title compound after purification by reverse phase preparative HPLC eluted with acetonitrile/water (with 0.1% ammonia).

$^1$H NMR (400 MHz, DMSO-$d_6$) δ ppm 1.02-1.50 (m, 3H) 1.54-1.96 (m, 6H) 2.02-2.19 (m, 1H) 2.76-2.95 (m, 1H) 3.03-3.22 (m, 8H) 3.38-3.62 (m, 1H) 4.18-4.91 (m, 2H) 6.11-6.34 (m, 1H) 6.86-7.17 (m, 3H) 7.35-7.66 (m, 2H) 8.54 (d, J=1.01 Hz, 1H)

MS ES+:392

Example 14

N-Methyl-5-{3-[1-(propan-2-yl)-1H-indol-2-yl]piperidine-1-carbonyl}pyridazin-3-amine

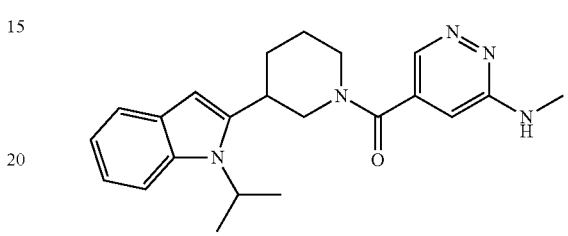

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-(propan-2-yl)-1H-indole (Intermediate 11; 0.065 g, 0.170 mmol) and methanamine [2M solution in THF] (1.698 ml, 3.40 mmol) using NMP (1 mL) as the solvent and irradiated in the microwave at 140° C. for 2 hours and 20 minutes. Additional methanamine [2M solution in THF] (1.698 ml, 3.40 mmol) was added and the reaction mixture was irradiated at 140° C. for another 1 hour to afford the title compound after purification by reverse phase preparative HPLC eluted with acetonitrile/water (with 0.1% ammonia).

$^1$H NMR (400 MHz, DMSO-$d_6$) δ ppm 1.07-1.51 (m, 3H) 1.54-1.95 (m, 6H) 2.02-2.20 (m, 1H) 2.75-2.97 (m, 4H) 2.98-3.24 (m, 2H) 3.44-3.63 (m, 1H) 4.22-4.91 (m, 2H) 6.14-6.33 (m, 1H) 6.72-6.86 (m, 1H) 6.86-7.14 (m, 3H) 7.36-7.67 (m, 2H) 8.40-8.52 (m, 1H)

MS ES+:378

Example 15

2-{1-[(1-Ethyl-1H-pyrazol-4-yl)carbonyl]piperidin-3-yl}-1-(propan-2-yl)-1H-indole

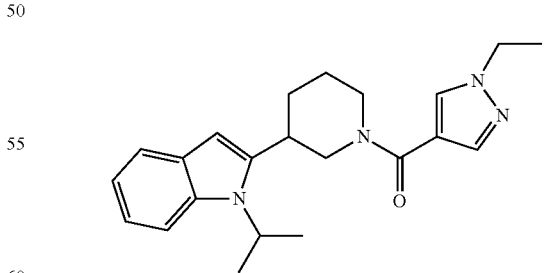

Prepared as described for N,N-dimethyl-4-[3-(1-methyl-1H-indol-2-yl)piperidine-1-carbonyl]pyridin-2-amine (Example 8) from 1-ethyl-1H-pyrazole-4-carboxylic acid (CAS 400858-54-0, 0.033 g, 0.238 mmol) and 2-(piperidin-3-yl)-1-(propan-2-yl)-1H-indole (Intermediate 12; 0.048 g, 0.198 mmol). The crude reaction mixture was extracted into EtOAc and purified by reverse phase preparative HPLC eluted with acetonitrile/water (with 0.1% ammonia) to afford the title compound.

¹H NMR (400 MHz, DMSO-d₆) δ ppm 1.26-1.91 (m, 12H) 2.01-2.18 (m, 1H) 2.5-3.4 (br., 3H) 4.05-4.20 (m, 2H) 4.21-4.99 (br., 3H) 6.26 (s, 1H) 6.85-7.00 (m, 1H) 7.01-7.08 (m, 1H) 7.47 (d, J=7.58 Hz, 1H) 7.57 (d, J=8.08 Hz, 1H) 7.70 (s, 1H) 8.11 (br. s., 1H)

¹H NMR (300 MHz, 90° C., DMSO-d₆) δ ppm 1.41 (t, J=7.27 Hz, 3H) 1.55 (d+d, J=6.89, 6H) 1.59-1.94 (m, 3H) 2.07-2.21 (m, 1H) 2.9-3.2 (m, 3H) 4.16 (q, J=7.18 Hz, 2H) 4.23-4.53 (m, 2H) 4.65-4.82 (m, 1H) 6.28 (s, 1H) 6.92-7.00 (m, 1H) 7.01-7.10 (m, 1H) 7.47 (d, J=7.74 Hz, 1H) 7.54 (d, J=8.31 Hz, 1H) 7.65 (s, 1H) 8.00 (s, 1H)

MS ES⁺:365

Example 16

1-Methyl-4-{3-[1-(propan-2-yl)-1H-indol-2-yl]piperidine-carbonyl}-1H-pyrazol-3-amine

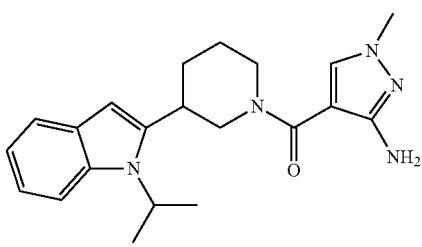 [SMILES: CC(C)n1c(C2CCCN(C(=O)c3cn(C)nc3N)C2)cc2ccccc21]

To a stirred suspension of tert-butyl N-(1-methyl-4-{3-[1-(propan-2-yl)-1H-indol-2-yl]piperidine-1-carbonyl}-1H-pyrazol-3-yl)carbamate (Intermediate 16; 0.072 g, 0.155 mmol) in methanol (1 mL) was added HCl [4.0 M in dioxane] (0.116 ml, 0.464 mmol). The reaction mixture was stirred at ambient temperature overnight. LCMS analysis showed that the reaction had not reached completion so the reaction mixture was concentrated in vacuo and re-dissolved in methanol (1 mL) and more HCl [4.0 M in dioxane] (0.116 ml, 0.464 mmol) was added. The reaction mixture was stirred at ambient temperature overnight. This process was repeated one more time until the reaction had reached completion. The volatile components were removed in vacuo and partitioned between DCM and saturated aqueous NaHCO₃. The organic phase was removed using a phase separator cartridge and the aqueous phase was extracted with more DCM. The organics were combined and the crude product was purified by reverse phase preparative HPLC eluted with acetonitrile/water (with 0.1% ammonia) to afford the title compound.

¹H NMR (400 MHz, DMSO-d₆) δ ppm 1.55 (m, 6H) 1.60-1.86 (m, 3H) 2.04-2.15 (m, 1H) 2.75-3.14 (m, 3H) 3.26-3.58 (m, 3H) 4.27 (m, 1H) 4.45 (m, 1H) 4.73 (m, 1H) 5.15 (s, 2H) 6.26 (s, 1H) 6.91-7.00 (m, 1H) 7.01-7.09 (m, 1H) 7.47 (d, J=7.83 Hz, 1H) 7.58 (d, J=8.08 Hz, 1H) 7.76 (s, 1H)

MS ES⁺:366

Example 17

1-Ethyl-2-{1-[(1-ethyl-1H-pyrazol-4-yl)carbonyl]piperidin-3-yl}-5-methyl-1H-indole

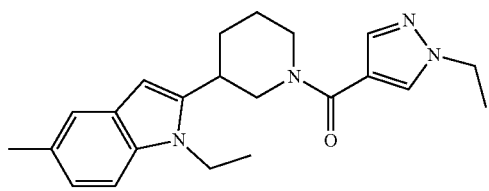 [SMILES: CCn1cc(C(=O)N2CCCC(c3cc4cc(C)ccc4n3CC)C2)cn1]

Prepared as described for N,N-dimethyl-4-[3-(1-methyl-1H-indol-2-yl)piperidine-1-carbonyl]pyridin-2-amine (Example 8) from 1-ethyl-5-methyl-2-(piperidin-3-yl)-1H-indole hemi-formate (Intermediate 19; 0.0782 g, 0.298 mmol) and 1-ethyl-1H-pyrazole-4-carboxylic acid (CAS 400858-54-0, 0.046 g, 0.328 mmol) in DCM (1 mL) with an additional step, whereby the crude product after work-up was passed through a pre-equlibrated SCX-2 (1 g) cartridge and was washed through with DCM before being purified by reverse phase preparative HPLC eluted with acetonitrile/water (with 0.1% ammonia) to afford the title compound.

¹H NMR (300 MHz, CD₃CN) δ ppm 1.26 (br. m, 3H) 1.44 (t, J=7.27 Hz, 3H) 1.56-1.92 (m, 3H) 2.17 (obscured, s, 1H) 2.41 (s, 3H) 2.51-3.51 (br. m, 3H) 4.16 (q, J=7.11 Hz, 4H) 4.35 (br. m, 2H) 6.23 (s, 1H) 6.98 (d, J=8.31 Hz, 1H) 7.17-7.37 (m, 2H) 7.65 (s, 1H) 7.80 (br. s, 1H)

MS ES⁺:365

Example 18

5-[3-(1-Ethyl-3-methyl-1H-indol-2-yl)piperidine-1-carbonyl]-N-methylpyridazin-3-amine

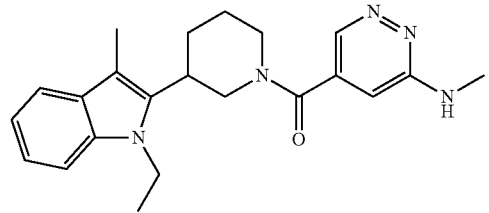 [SMILES: CCn1c(C2CCCN(C(=O)c3cnnc(NC)c3)C2)c(C)c2ccccc21]

Prepared as described for N-methyl-5-[3-(1-methyl-1H-indol-2-yl)piperidine-1-carbonyl]pyridazin-3-amine (Example 9) from 2-[1-(6-Chloropyridazine-4-carbonyl)piperidin-3-yl]-1-ethyl-3-methyl-1H-indole (Intermediate 23; 0.075 g, 0.196 mmol) and methanamine [2 M solution in THF] (3.92 ml, 7.84 mmol) using NMP (1 mL) as the solvent and irradiated in the microwave at 140° C. for 4 hours to afford the title compound after purification by reverse phase preparative HPLC eluted with acetonitrile/water (with 0.1% ammonia).

¹H NMR (400 MHz, CD₃CN) δ ppm 1.03-1.41 (m, 3H) 1.59-1.85 (m, 1H) 1.90-2.30 (obscured, m, 3H) 2.31-2.48 (m, 3H) 2.80-3.77 (m, 7H) 4.00-4.35 (m, 2H) 4.54-4.79 (m, 1H) 5.46-5.63 (m, 1H) 6.61-6.78 (m, 1H) 6.88-7.59 (m, 4H) 8.40-8.55 (m, 1H)

MS ES⁺:378

Example 19

5-[3-(1-Ethyl-5-methyl-1H-indol-2-yl)piperidine-1-carbonyl]-N-methylpyridazin-3-amine

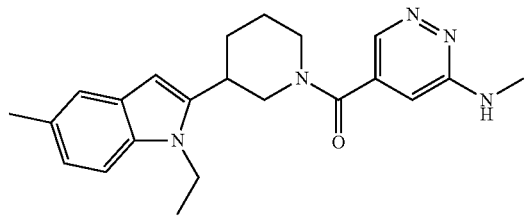

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-ethyl-5-methyl-1H-indole (Intermediate 28; 0.0575 g, 0.150 mmol) and methanamine [2M solution in THF] (3.00 ml, 6.01 mmol) using NMP (1 mL) as the solvent and irradiated in the microwave at 140° C. for 4 hours to afford the title compound after purification by reverse phase preparative HPLC eluted with acetonitrile/water (with 0.1% ammonia).

$^1$H NMR (400 MHz, CD$_3$CN) δ ppm 0.95-1.45 (m, 3H) 1.56-1.95 (m, 4H) 2.31-2.46 (m, 3H) 2.75-3.26 (m, 6H) 3.57-3.76 (m, 1H) 3.86-4.34 (m, 2H) 4.50-4.75 (m, 1H) 4.80-5.60 (m, 1H) 6.12-6.31 (m, 1H) 6.55-6.77 (m, 1H) 6.86-7.06 (m, 1H) 7.12-7.37 (m, 2H) 8.36-8.53 (m, 1H)

MS ES$^+$:378

Example 20

5-[3-(5-Chloro-1-ethyl-1H-indol-2-yl)piperidine-1-carbonyl]-N-methylpyridazin-3-amine

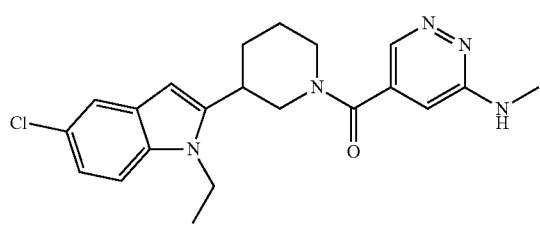 [SMILES: CCn1c(C2CCCN(C(=O)c3cnnc(NC)c3)C2)cc2cc(Cl)ccc21]

Prepared as described for N-methyl-5-[3-(1-methyl-1H-indol-2-yl)piperidine-1-carbonyl]pyridazin-3-amine (Example 9) from 5-chloro-2-[1-(6-chloropyridazine-4-carbonyl)piperidin-3-yl]-1-ethyl-1H-indole (Intermediate 29; 0.062 g, 0.154 mmol) and methanamine [2M solution in THF] (3.07 ml, 6.15 mmol) using NMP (1 mL) as the solvent and irradiated in the microwave at 140° C. for 4 hours to afford the title compound after purification by reverse phase preparative HPLC eluted with acetonitrile/water (with 0.1% ammonia).

$^1$H NMR (400 MHz, CD$_3$CN) δ ppm 1.02-1.41 (m, 3H) 1.52-1.90 (m, 3H) 2.11-2.17 (obscured m, 1H) 2.74-3.28 (m, 6H) 3.67 (m, 1H) 3.86-4.39 (m, 2H) 4.48-4.78 (m, 1H) 5.45-5.66 (m, 1H) 6.19-6.39 (m, 1H) 6.58-6.80 (m, 1H) 6.96-7.20 (m, 1H) 7.24-7.43 (m, 1H) 7.43-7.62 (m, 1H) 8.31-8.57 (m, 1H)

MS ES$^+$:398

Example 21

5-[3-(1-Ethyl-5-methyl-1H-indol-2-yl)piperidine-1-carbonyl]-N,N-dimethylpyridazin-3-amine

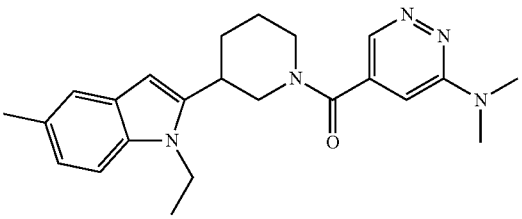

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-1-ethyl-5-methyl-1H-indole (Intermediate 28; 0.0575 g, 0.150 mmol) and dimethylamine [2.0M in THF] (1.502 ml, 3.00 mmol) using NMP (1 mL) as the solvent and irradiated in the microwave at 140° C. for 30 minutes. Purification by reverse phase preparative HPLC eluted with acetonitrile/water (with 0.1% ammonia) afforded the title compound.

$^1$H NMR (400 MHz, CD$_3$CN) δ ppm 0.96-1.45 (m, 3H) 1.53-1.95 (m, 3H) 2.08-2.22 (obscured m, 1H) 2.32-2.46 (m, 3H) 2.75-3.28 (m, 9H) 3.51-3.72 (m, 1H) 3.79-4.34 (m, 2H) 4.46-4.80 (m, 1H) 6.10-6.33 (m, 1H) 6.76-7.04 (m, 2H) 7.11-7.38 (m, 2H) 8.37-8.54 (m, 1H)

MS ES$^+$:392

Example 22

5-[3-(5-Chloro-1-ethyl-1H-indol-2-yl)piperidine-1-carbonyl]-N,N-dimethylpyridazin-3-amine

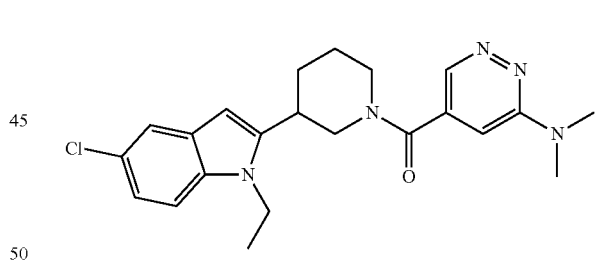

Prepared as described for N-methyl-5-[3-(1-methyl-1H-indol-2-yl)piperidine-1-carbonyl]pyridazin-3-amine (Example 9) from 5-chloro-2-[1-(6-chloropyridazine-4-carbonyl)piperidin-3-yl]-1-ethyl-1H-indole (Intermediate 29; 0.031 g, 0.077 mmol) and dimethylamine [2.0M in THF] (0.769 ml, 1.537 mmol) using NMP (1 mL) as the solvent and irradiated in the microwave at 140° C. for 1 hour to afford the title compound after purification by reverse phase preparative HPLC eluted with acetonitrile/water (with 0.1% ammonia).

$^1$H NMR (400 MHz, CD$_3$CN) δ ppm 1.00-1.47 (m, 3H) 1.57-1.94 (m, 3H) 2.18 (obscured m, 1H) 2.76-3.27 (m, 9H) 3.54-3.75 (m, 1H) 3.84-4.37 (m, 2H) 4.48-4.80 (m, 1H) 6.19-6.40 (m, 1H) 6.74-6.96 (m, 1H) 7.12 (m, 1H) 7.24-7.43 (m, 1H) 7.44-7.59 (m, 1H) 8.39-8.55 (m, 1H)

MS ES$^+$:412

Example 23

N-Methyl-5-[3-(3-methyl-1H-indol-2-yl)piperidine-1-carbonyl]pyridazin-3-amine

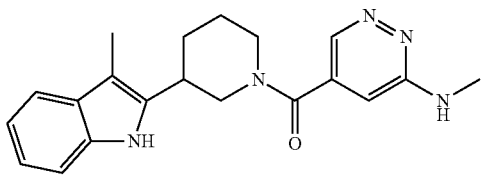 [SMILES: CNc1cc(C(=O)N2CCCC(c3[nH]c4ccccc4c3C)C2)cnn1]

Prepared as described for N-methyl-5-[3-(1-methyl-1H-indol-2-yl)piperidine-1-carbonyl]pyridazin-3-amine (Example 9) from 2-[1-(6-chloropyridazine-4-carbonyl)piperidin-3-yl]-3-methyl-1H-indole (Intermediate 34; 0.034 g, 0.096 mmol) and methanamine [2M solution in THF] (1.916 ml, 3.83 mmol) using NMP (1 mL) as the solvent and irradiated in a microwave at 140° C. for 1 hour. Additional methanamine [2M solution in THF] (1.916 ml, 3.83 mmol) was added and the reaction was irradiated in the microwave at 140° C. for a further 5 hours to afford the title compound after purification by reverse phase preparative HPLC eluted with acetonitrile/water (with 0.1% ammonia).

$^1$H NMR (400 MHz, CD$_3$CN) δ ppm 1.77 (m, 2H) 2.15-2.36 (obscured m, 5H) 2.74-3.06 (m, 4H) 3.08-3.28 (m, 2H) 3.52-3.74 (m, 1H) 4.51-4.70 (m, 1H) 5.35-5.62 (m, 1H) 6.59-6.79 (m, 1H) 6.89-7.17 (m, 2H) 7.20-7.55 (m, 2H) 8.39-8.54 (m, 1H) 8.89-9.16 (m, 1H)

MS ES$^+$:350

Example 24

N,N-Dimethyl-5-[3-(3-methyl-1H-indol-2-yl)piperidine-1-carbonyl]pyridazin-3-amine

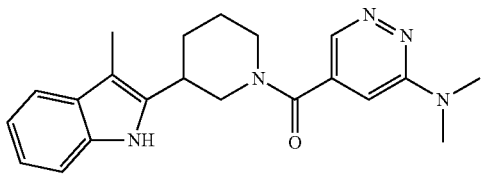 [SMILES: Cc1c(C2CCCN(C(=O)c3cnnc(N(C)C)c3)C2)[nH]c2ccccc12]

Prepared as described for N-methyl-5-[3-(1-methyl-1H-indol-2-yl)piperidine-1-carbonyl]pyridazin-3-amine (Example 9) from 2-[1-(6-Chloropyridazine-4-carbonyl)piperidin-3-yl]-3-methyl-1H-indole (Intermediate 34; 0.034 g, 0.096 mmol) and dimethylamine [2M solution in THF] (1.916 ml, 3.83 mmol) using NMP (1 mL) as the solvent and irradiated in a microwave at 140° C. for 30 minutes to afford the title compound after purification using reverse phase preparative HPLC eluted with acetonitrile/water (with 0.1% ammonia) followed by a second purification using reverse phase preparative HPLC eluted with acetonitrile/water (with 0.1% formic acid).

$^1$H NMR (400 MHz, CD$_3$CN) δ ppm 1.53-1.84 (m, 2H) 2.00-2.39 (m, 5H) 2.78-3.30 (m, 9H) 3.46-3.74 (m, 1H) 4.51-4.73 (m, 1H) 6.76-6.93 (m, 1H) 6.94-7.16 (m, 2H) 7.23-7.55 (m, 2H) 8.32-8.56 (m, 1H) 8.89-9.22 (m, 1H)

MS ES$^+$:364

Example 25

4-[3-(1-Ethyl-3-methyl-1H-indol-2-yl)piperidine-1-carbonyl]-1-methyl-1H-pyrazol-3-amine

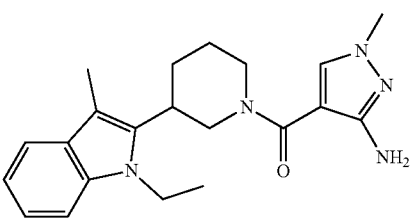 [SMILES: CCn1c(C2CCCN(C(=O)c3cn(C)nc3N)C2)c(C)c2ccccc21]

To a stirred solution of tert-butyl N-{4-[3-(1-ethyl-3-methyl-1H-indol-2-yl)piperidine-1-carbonyl]-1-methyl-1H-pyrazol-3-yl)carbamate (Intermediate 36; 234 mg, carried through from previous step without purification) in DCM (1 mL) was added TFA (0.1 ml, 1.298 mmol). The reaction mixture was stirred at ambient temperature for 90 hours. The volatile components were removed in vacuo and the crude product was purified by reverse phase preparative HPLC eluted with acetonitrile/water (with 0.1% ammonia) to afford the title compound.

$^1$H NMR (400 MHz, CD$_3$CN) δ ppm 0.94-1.31 (m, 3H) 1.53-1.91 (obscured m, 2H) 2.01-2.47 (obscured m, 5H) 3.01-3.15 (m, 2H) 3.25-3.41 (m, 1H) 3.63 (s, 3H) 4.22 (q, J=7.16 Hz, 2H) 4.36-4.51 (m, 2H) 4.75 (br. s., 2H) 6.96-7.08 (m, 1H) 7.15 (t, J=7.20 Hz, 1H) 7.33 (d, J=8.08 Hz, 1H) 7.42-7.54 (m, 2H)

MS ES$^+$:366

Example 26

4-[3-(1-Ethyl-5-methyl-1H-indol-2-yl)piperidine-1-carbonyl]-1-methyl-1H-pyrazol-3-amine

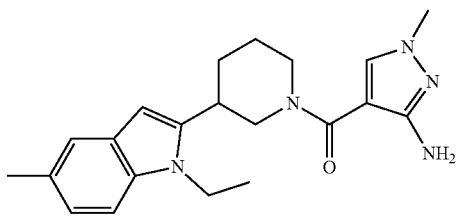 [SMILES: CCn1c(C2CCCN(C(=O)c3cn(C)nc3N)C2)cc2cc(C)ccc21]

Prepared as described for 4-[3-(1-ethyl-3-methyl-1H-indol-2-yl)piperidine-1-carbonyl]-1-methyl-1H-pyrazol-3-amine (Example 25) from tert-butyl N-{4-[3-(1-ethyl-5-methyl-1H-indol-2-yl)piperidine-1-carbonyl]-1-methyl-1H-pyrazol-3-yl}carbamate (Intermediate 37; 277 mg, carried through from previous step without purification) to afford the title compound.

$^1$H NMR (400 MHz, CD$_3$CN) δ ppm 1.22-1.47 (m, 3H) 1.55-1.91 (m, 3H) 2.04-2.13 (m, 1H) 2.37-2.57 (m, 3H) 2.87-3.20 (m, 3H) 3.64 (s, 3H) 4.20 (q, J=7.07 Hz, 2H) 4.30-4.41 (m, 1H) 4.45-4.59 (m, 1H) 4.74 (br. s., 2H) 6.23 (s, 1H) 6.98 (d, J=8.34 Hz, 1H) 7.20-7.35 (m, 2H) 7.48 (s, 1H)

MS ES$^+$:366

Example 27

4-[3-(5-Chloro-1-ethyl-1H-indol-2-yl)piperidine-1-carbonyl]-1-methyl-1H-pyrazol-3-amine

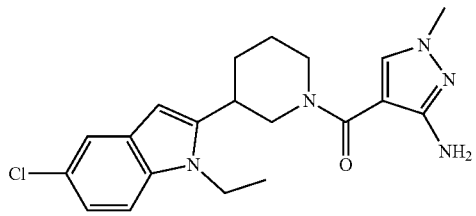 [SMILES: CCn1c(C2CCCN(C(=O)c3cn(C)nc3N)C2)cc2cc(Cl)ccc21]

Prepared as described for 4-[3-(1-ethyl-3-methyl-1H-indol-2-yl)piperidine-1-carbonyl]-1-methyl-1H-pyrazol-3-amine (Example 25) from tert-butyl N-{4-[3-(5-chloro-1-ethyl-1H-indol-2-yl)piperidine-1-carbonyl]-1-methyl-1H-pyrazol-3-yl}carbamate (Intermediate 38; 259 mg, carried through from previous step without purification) to afford the title compound.

$^1$H NMR (400 MHz, CD$_3$CN) δ ppm 1.31 (t, J=7.20 Hz, 3H) 1.60-1.93 (m, 3H) 2.08-2.13 (obscured m, 1H) 2.87-3.19 (m, 3H) 3.64 (s, 3H) 4.23 (q, J=7.07 Hz, 2H) 4.28-4.39 (m, 1H) 4.46-4.58 (m, 1H) 4.75 (br. s., 2H) 6.32 (s, 1H) 7.13 (dd, J=8.72, 1.89 Hz, 1H) 7.38 (d, J=8.84 Hz, 1H) 7.49 (s, 1H) 7.53 (d, J=2.02 Hz, 1H)

MS ES$^+$:386

Example 28

5-[3-(5-Chloro-3-methylpyridin-2-yl)piperidine-1-carbonyl]-N,N-dimethylpyridazin-3-amine

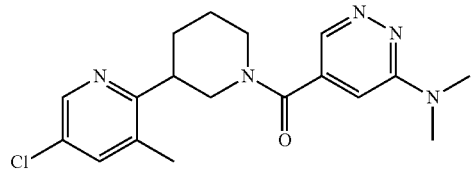 [SMILES: Cc1cc(Cl)cnc1C1CCCN(C(=O)c2cnnc(N(C)C)c2)C1]

A solution of 3-chloro-5-[3-(5-chloro-3-methylpyridin-2-yl)piperidine-1-carbonyl]pyridazine (Intermediate 39; 0.063 g, 0.179 mmol) and dimethylamine (2 M in THF) (1.794 ml, 3.59 mmol) in butan-1-ol (2 mL) was heated in a sealed tube to 135° C. for 2 hours. The solution was concentrated in vacuo and the crude product was purified by reverse phase preparative HPLC eluted with acetonitrile/water (with 0.1% ammonia) to afford the title compound.

$^1$H NMR (400 MHz, DMSO-d$_6$) δ ppm 1.56-1.97 (m, 4H) 2.17-2.42 (m, 3H) 2.78-3.19 (m, 8H) 3.33-3.56 (m, 2H) 4.43-4.56 (m, 1H) 7.03-7.09 (m, 1H) 7.61-7.81 (m, 1H) 8.30-8.54 (m, 2H)

MS ES$^+$:360

Example 29

4-{3-[5-Chloro-3-(trifluoromethyl)pyridin-2-yl]-3-methoxypiperidine-1-carbonyl}-N-methylpyridin-2-amine formate

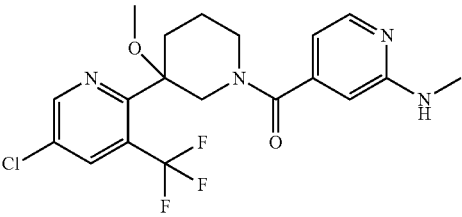 [SMILES: CNc1cc(C(=O)N2CCCC(OC)(c3ncc(Cl)cc3C(F)(F)F)C2)ccn1]

Prepared as described for N,N-dimethyl-4-[3-(1-methyl-1H-indol-2-yl)piperidine-1-carbonyl]pyridin-2-amine (Example 8) from 5-chloro-2-(3-methoxypiperidin-3-yl)-3-(trifluoromethyl)pyridine (Intermediate 43 (free base); 0.010 g, 0.026 mmol) and 2-(methylamino)pyridine-4-carboxylic acid hydrochloride hemi hydrate (CAS 876717-53-2, 7.75 mg, 0.039 mmol) in DCM (0.5 mL), except that the reaction was quenched by diluting in MeOH (3 mL) and stirred for 1 hour. The crude product was purified by reverse phase preparative HPLC eluted with acetonitrile/water (with 0.1% formic acid) to afford the title compound.

$^1$H NMR (400 MHz, Methanol-d$_4$) δ ppm 1.78-2.11 (m, 3H) 2.22-2.46 (m, 1H) 2.87-3.24 (m, 7H) 3.40-4.95 (obscured m, 3H) 6.47-6.68 (m, 2H) 7.84-8.35 (m, 3H) 8.81 (dd, J=13.77, 1.89 Hz, 1H)

MS ES$^+$:429

Example 30

5-({3-[5-Chloro-3-(trifluoromethyl)pyridin-2-yl]-3-methoxypiperidin-1-yl}carbonyl)-N-methyl-pyridazin-3-amine

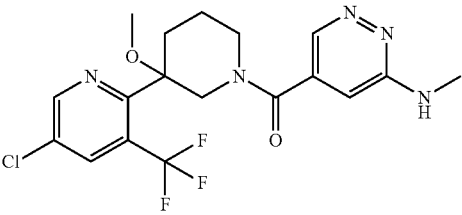 [SMILES: CNc1cc(C(=O)N2CCCC(OC)(c3ncc(Cl)cc3C(F)(F)F)C2)cnn1]

Prepared as described for N-methyl-5-[3-(1-methyl-1H-indol-2-yl)piperidine-1-carbonyl]pyridazin-3-amine (Example 9) from 3-chloro-5-{3-[5-chloro-3-(trifluoromethyl)pyridin-2-yl]-3-methoxypiperidine-1-carbonyl}pyridazine (Intermediate 48; 0.08 g, 0.184 mmol) and methanamine [2 M solution in THF] (3.68 ml, 7.35 mmol) using NMP (1 mL) as the solvent and irradiated in the microwave at 140° C. for 2.5 hours to afford the title compound after purification by reverse phase preparative HPLC eluted with acetonitrile/water (with 0.1% ammonia).

$^1$H NMR (400 MHz, CD$_3$CN) δ ppm 1.48-2.34 (obscured m, 4H) 2.83-3.13 (m, 7H) 3.20-4.88 (m, 3H) 5.36-5.54 (m, 1H) 6.53-6.65 (m, 1H) 8.04-8.24 (m, 1H) 8.28-8.41 (m, 1H) 8.65-8.76 (m, 1H)

MS ES$^+$:430

Example 31

5-{3-[5-Chloro-3-(trifluoromethyl)pyridin-2-yl]-3-methoxypiperidine-1-carbonyl}-N,N-dimethyl-pyridazin-3-amine

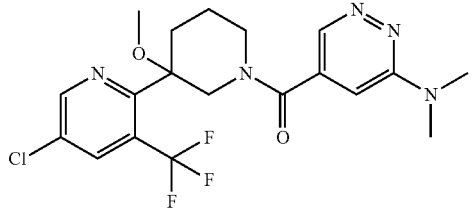 [SMILES: COC1(c2ncc(Cl)cc2C(F)(F)F)CCCN(C(=O)c2cnnc(N(C)C)c2)C1]

Prepared as described for N-methyl-5-[3-(1-methyl-1H-indol-2-yl)piperidine-1-carbonyl]pyridazin-3-amine (Example 9) from 3-chloro-5-{3-[5-chloro-3-(trifluoromethyl)pyridin-2-yl]-3-methoxypiperidine-1-carbonyl}pyridazine (Intermediate 48; 0.08 g, 0.184 mmol) and dimethylamine [2 M solution in THF] (3.68 ml, 7.35 mmol) using NMP (1 mL) as the solvent and irradiated in the microwave at 140° C. for 1 hour to afford the title compound after purification by reverse phase preparative HPLC eluted with acetonitrile/water (with 0.1% ammonia).

$^1$H NMR (300 MHz, CD$_3$CN) δ ppm 1.52-2.44 (obscured m, 4H) 2.84-3.23 (m, 10H) 3.23-4.97 (m, 3H) 6.77-6.90 (m, 1H) 8.05-8.31 (m, 1H) 8.34-8.48 (m, 1H) 8.69-8.85 (m, 1H)

MS ES$^+$:444

Example 32

5-Chloro-2-[1-(1-ethyl-1H-pyrazole-4-carbonyl)-3-methoxypiperidin-3-yl]-3-(trifluoromethyl)pyridine

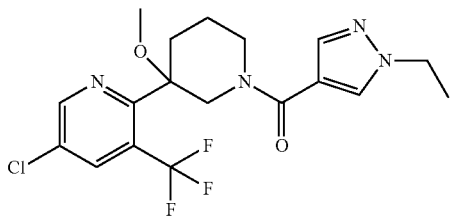 [SMILES: CCn1cc(C(=O)N2CCCC(OC)(c3ncc(Cl)cc3C(F)(F)F)C2)cn1]

Prepared as described for N,N-dimethyl-4-[3-(1-methyl-1H-indol-2-yl)piperidine-1-carbonyl]pyridin-2-amine (Example 8) from 5-chloro-2-(3-methoxypiperidin-3-yl)-3-(trifluoromethyl)pyridine hydrochloride (Intermediate 43; 66.2 mg, 0.2 mmol) and 1-ethyl-1H-pyrazole-4-carboxylic acid (CAS 400858-54-0, 0.031 g, 0.220 mmol) in DCM (0.5 mL) to afford the title compound after purification by reverse phase preparative HPLC eluted with acetonitrile/water (with 0.1% ammonia).

$^1$H NMR (400 MHz, CD$_3$CN) δ ppm 1.44 (t, J=7.20 Hz, 3H) 1.69-2.71 (obscured br. m, 4H) 2.84-3.64 (br. m, 5H) 4.03-5.04 (br. m+q, 4H) 7.62 (br. s., 1H) 7.79 (br. s., 1H) 8.22 (br. s., 1H) 8.77 (m, 1H)

MS ES$^+$:417

Example 33

4-{3-[5-Chloro-3-(trifluoromethyl)pyridin-2-yl]-3-methoxypiperidine-1-carbonyl}-N,N-dimethylpyridin-2-amine

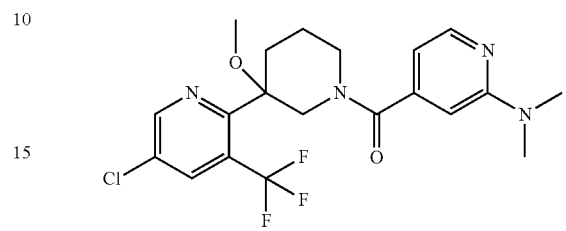

Prepared as described for N,N-dimethyl-4-[3-(1-methyl-1H-indol-2-yl)piperidine-1-carbonyl]pyridin-2-amine (Example 8) from 5-chloro-2-(3-methoxypiperidin-3-yl)-3-(trifluoromethyl)pyridine hydrochloride (Intermediate 43; 0.050 g, 0.151 mmol) and 2-(dimethylamino)pyridine-4-carboxylic acid hydrochloride (0.046 g, 0.226 mmol) in DCM (1 mL) except purified by reverse phase preparative HPLC eluted with acetonitrile/water (with 0.1% formic acid) to afford the title compound.

$^1$H NMR (400 MHz, CD$_3$CN) δ ppm 1.48-2.67 (obscured m, 4H) 2.90-3.16 (m, 9H) 3.19-4.96 (m, 4H) 6.35-6.59 (m, 2H) 8.00-8.32 (m, 2H) 8.68-8.83 (m, 1H)

MS ES$^+$:443

Example 34

4-[3-(5-Chloro-3-methylpyridin-2-yl)-3-methoxypiperidine-1-carbonyl]-N-methylpyridin-2-amine

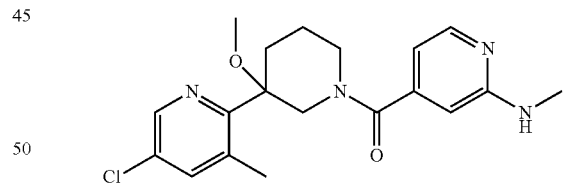

Prepared as described for N,N-dimethyl-4-[3-(1-methyl-1H-indol-2-yl)piperidine-1-carbonyl]pyridin-2-amine (Example 8) from 5-chloro-2-(3-methoxypiperidin-3-yl)-3-methylpyridine hydrochloride (Intermediate 49; 0.050 g, 0.180 mmol) and 2-(methylamino)pyridine-4-carboxylic acid hydrochloride hemi hydrate (CAS 876717-53-2, 0.053 g, 0.271 mmol) in DCM (1 mL) to afford the title compound.

$^1$H NMR (400 MHz, CD$_3$CN) δ ppm 1.37-1.90 (obscured m, 2H) 1.96-2.28 (obscured m, 2H) 2.35-2.52 (m, 3H) 2.69-3.03 (m, 6H) 3.13-3.40 (m, 2H) 3.44-4.83 (m, 2H) 5.04-5.24 (m, 1H) 6.16-6.43 (m, 2H) 7.34-7.60 (m, 1H) 7.96 (m, 1H) 8.17-8.33 (m, 1H)

MS ES$^+$:375

Example 35

4-[3-(5-Chloro-3-methylpyridin-2-yl)-3-fluoropiperidine-1-carbonyl]-N-methylpyridin-2-amine

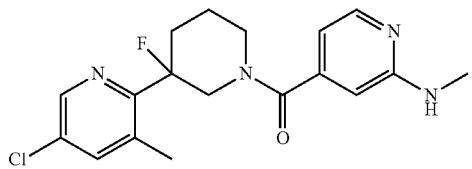 [SMILES: CNc1cc(C(=O)N2CCCC(F)(c3ncc(Cl)cc3C)C2)ccn1]

Prepared as described for N,N-dimethyl-4-[3-(1-methyl-1H-indol-2-yl)piperidine-1-carbonyl]pyridin-2-amine (Example 8) from 5-chloro-2-(3-fluoropiperidin-3-yl)-3-methylpyridine hydrochloride (Intermediate 52; 0.050 g, 0.189 mmol) and 2-(methylamino)pyridine-4-carboxylic acid hydrochloride hemi hydrate (CAS 876717-53-2, 0.056 g, 0.283 mmol) in DCM (1 mL) to afford the title compound after purification by reverse phase preparative HPLC eluted with acetonitrile/water (with 0.1% formic acid).

$^1$H NMR (400 MHz, CD$_3$CN) δ ppm 1.59-1.97 (obscured m, 3H) 2.13-2.29 (obscured m, 1H) 2.43-2.59 (m, 3H) 2.77-4.94 (m, 7H) 5.17-5.39 (m, 1H) 6.31-6.41 (m, 1H) 6.44-6.56 (m, 1H) 7.53-7.75 (m, 1H) 7.94-8.15 (m, 1H) 8.25-8.45 (m, 1H) MS ES$^+$:363

Example 36

5-[3-(5-Chloro-3-methylpyridin-2-yl)-3-methoxypiperidine-1-carbonyl]-N-methylpyridazin-3-amine

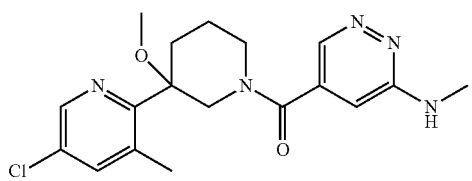 [SMILES: CNc1cc(C(=O)N2CCCC(OC)(c3ncc(Cl)cc3C)C2)cnn1]

Prepared as described for N-methyl-5-[3-(1-methyl-1H-indol-2-yl)piperidine-1-carbonyl]pyridazin-3-amine (Example 9) from 3-chloro-5-[3-(5-chloro-3-methylpyridin-2-yl)-3-methoxypiperidine-1-carbonyl]pyridazine (Intermediate 54; 0.057 g, 0.150 mmol) and methanamine [2 M solution in THF] (4.50 ml, 9.00 mmol) using NMP (1.5 mL) as the solvent and irradiated in the microwave at 140° C. for 3 hours to afford the title compound after purification by reverse phase preparative HPLC eluted with acetonitrile/water (with 0.1% ammonia).

$^1$H NMR (400 MHz, Methanol-d$_4$) δ ppm 1.55-2.06 (m, 3H) 2.14-2.67 (m, 4H) 2.89-3.28 (m, 7H) 3.38-4.97 (m, 3H) 6.76-6.92 (m, 1H) 7.48-7.73 (m, 1H) 8.30-8.45 (m, 2H).

MS ES$^+$:376

Example 37

5-[3-(5-Chloro-3-methylpyridin-2-yl)-3-methoxypiperidine-1-carbonyl]-N,N-dimethylpyridazin-3-amine

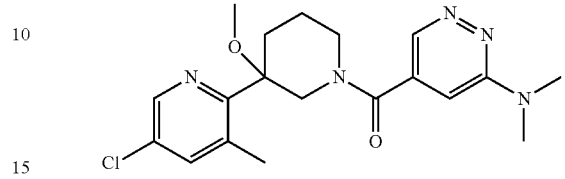

Prepared as described for N-methyl-5-[3-(1-methyl-1H-indol-2-yl)piperidine-1-carbonyl]pyridazin-3-amine (Example 9) from 3-chloro-5-[3-(5-chloro-3-methylpyridin-2-yl)-3-methoxypiperidine-1-carbonyl]pyridazine (Intermediate 54; 0.057 g, 0.150 mmol) and dimethylamine [2 M solution in THF] (6.3 ml, 12.6 mmol) using NMP (1.5 mL) as the solvent and irradiated in the microwave at 140° C. for 90 minutes to afford the title compound after purification by reverse phase preparative HPLC eluted with acetonitrile/water (with 0.1% ammonia).

$^1$H NMR (400 MHz, CD$_3$CN) δ ppm 1.51-2.64 (obscured m, 7H) 2.87-4.97 (m, 13H) 6.75-6.90 (m, 1H) 7.46-7.69 (m, 1H) 8.30-8.48 (m, 2H)

MS ES$^+$:390

Example 38

5-[3-(5-Chloro-3-methylpyridin-2-yl)-3-fluoropiperidine-1-carbonyl]-N-methylpyridazin-3-amine

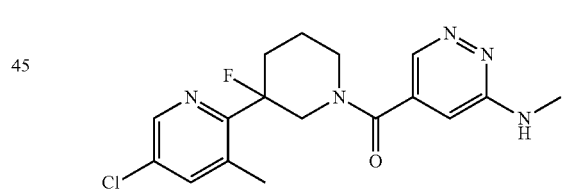

Prepared as described for N-methyl-5-[3-(1-methyl-1H-indol-2-yl)piperidine-1-carbonyl]pyridazin-3-amine (Example 9) from 3-chloro-5-{[3-(5-chloro-3-methylpyridin-2-yl)-3-fluoropiperidin-1-yl]carbonyl}pyridazine (Intermediate 55; 0.087 g, 0.236 mmol) and methanamine [2 M solution in THF] (4.71 ml, 9.43 mmol) using NMP (1 mL) as the solvent and irradiated in the microwave at 140° C. for 2.5 hours to afford the title compound after purification by reverse phase preparative HPLC eluted with acetonitrile/water (with 0.1% ammonia).

$^1$H NMR (400 MHz, CD$_3$CN) δ ppm 1.63-2.57 (obscured m, 7H) 2.88-4.93 (m, 7H) 5.49-5.65 (m, 1H) 6.69 (m, 1H) 7.55-7.73 (m, 1H) 8.25-8.49 (m, 2H)

MS ES$^+$:364

Example 39

5-[3-(5-Chloro-3-methylpyridin-2-yl)-3-fluoropiperidine-1-carbonyl]-N,N-dimethylpyridazin-3-amine

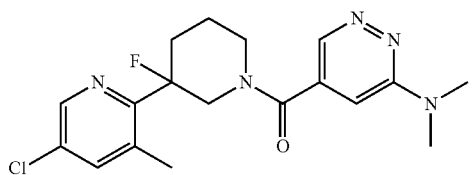 [SMILES: Cc1cc(Cl)cnc1C1(F)CCCN(C(=O)c2cnnc(N(C)C)c2)C1]

Prepared as described for N-methyl-5-[3-(1-methyl-1H-indol-2-yl)piperidine-1-carbonyl]pyridazin-3-amine (Example 9) from 3-chloro-5-{[3-(5-chloro-3-methylpyridin-2-yl)-3-fluoropiperidin-1-yl]carbonyl}pyridazine (Intermediate 55; 0.087 g, 0.236 mmol) and dimethylamine [2 M solution in THF] (4.7 ml, 9.4 mmol) using NMP (1 mL) as the solvent and irradiated in the microwave at 140° C. for 1 hour to afford the title compound after purification by reverse phase preparative HPLC eluted with acetonitrile/water (with 0.1% ammonia).

$^1$H NMR (400 MHz, CD$_3$CN) δ ppm 1.62-2.59 (obscured m, 7H) 2.90-4.97 (m, 10H) 6.77-6.90 (m, 1H) 7.55-7.73 (m, 1H) 8.26-8.48 (m, 2H)

MS ES$^+$:378

Example 40

5-Chloro-2-[1-(1-ethyl-1H-pyrazole-4-carbonyl)-3-methoxypiperidin-3-yl]-3-methylpyridine

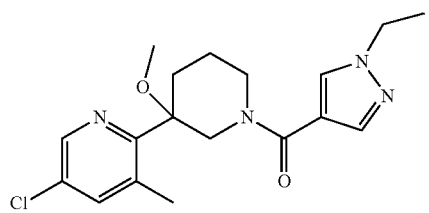 [SMILES: CCn1cc(C(=O)N2CCCC(OC)(c3ncc(Cl)cc3C)C2)cn1]

Prepared as described for N,N-dimethyl-4-[3-(1-methyl-1H-indol-2-yl)piperidine-1-carbonyl]pyridin-2-amine (Example 8) from 5-chloro-2-(3-methoxypiperidin-3-yl)-3-methylpyridine hydrochloride (Intermediate 49; 0.050 g, 0.180 mmol) and 1-ethyl-1H-pyrazole-4-carboxylic acid (CAS 400858-54-0, 0.033 g, 0.234 mmol) in DCM (1 mL) to afford the title compound.

$^1$H NMR (400 MHz, CD$_3$CN) δ ppm 1.45 (t, J=7.33 Hz, 3H) 1.61-2.69 (obscured br. m, 7H) 2.75-3.68 (br. m, 5H) 4.04-5.02 (br. m+q, 4H) 7.44-7.68 (m, 2H) 7.79 (s, 1H) 8.29-8.44 (m, 1H)

MS ES$^+$:363

Example 41

5-Chloro-2-[1-(1-ethyl-1H-pyrazole-4-carbonyl)-3-fluoropiperidin-3-yl]-3-methylpyridine

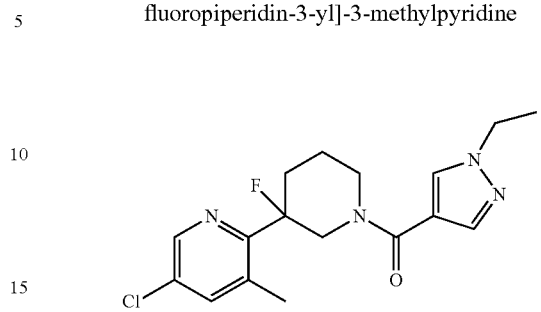

Prepared as described for N,N-dimethyl-4-[3-(1-methyl-1H-indol-2-yl)piperidine-1-carbonyl]pyridin-2-amine (Example 8) from 5-chloro-2-(3-fluoropiperidin-3-yl)-3-methylpyridine hydrochloride (Intermediate 52; 0.050 g, 0.189 mmol) and 1-ethyl-1H-pyrazole-4-carboxylic acid (CAS 400858-54-0, 0.034 g, 0.245 mmol) in DCM (1 mL) to afford the title compound.

$^1$H NMR (400 MHz, CD$_3$CN) δ ppm 1.43 (t, J=7.07 Hz, 3H) 1.66-2.02 (obscured m, 2H) 2.23-2.62 (m, 5H) 2.68-4.05 (br. m, 2H) 4.16 (q, J=6.82 Hz, 2H) 4.24-5.16 (br. m, 2H) 7.54-7.70 (m, 2H) 7.80 (br. s., 1H) 8.37 (s, 1H)

MS ES$^+$:351

Example 42

4-[3-(5-Chloro-3-methylpyridin-2-yl)-3-methoxypiperidine-1-carbonyl]-1-methyl-1H-pyrazol-3-amine

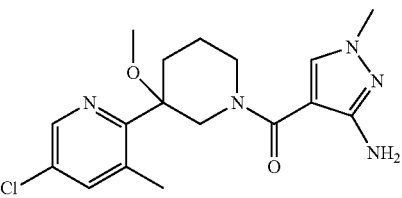 [SMILES: COC1(c2ncc(Cl)cc2C)CCCN(C(=O)c2cn(C)nc2N)C1]

To a stirred solution of tert-butyl N-{4-[3-(5-chloro-3-methylpyridin-2-yl)-3-methoxypiperidine-1-carbonyl]-1-methyl-1H-pyrazol-3-yl}carbamate (Intermediate 56; 84 mg, 0.18 mmol) in DCM (1 mL) was added TFA (0.25 ml, 3.24 mmol). The reaction was stirred at ambient temperature for 140 minutes and then quenched with saturated aqueous NaHCO$_3$. The resulting mixture was extracted into DCM, then loaded onto a strong cation exchange cartridge (SCX-2, 1 g), washed with DCM/MeOH (4:1) and eluted off with DCM/[2M NH$_3$ in MeOH] (4:1). The crude product was purified by reverse phase preparative HPLC eluted with acetonitrile/water (with 0.1% ammonia) to afford the title compound.

$^1$H NMR (400 MHz, CD$_3$CN) δ ppm 1.56-2.37 (obscured m, 4H) 2.51 (s, 3H) 2.95 (s, 3H) 3.02-3.17 (m, 1H) 3.37-3.53 (m, 1H) 3.65 (s, 3H) 4.12-4.27 (m, 1H) 4.58-4.84 (m, 3H) 7.50 (s, 1H) 7.62 (d, J=2.02 Hz, 1H) 8.39 (d, J=2.02 Hz, 1H)

MS ES$^+$:364

Example 43

4-[3-(5-Chloro-3-methylpyridin-2-yl)-3-fluoropiperidine-1-carbonyl]-1-methyl-1H-pyrazol-3-amine

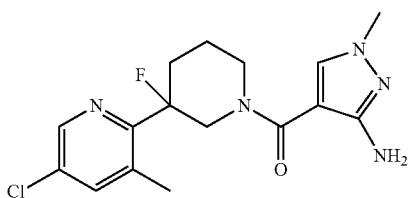 [SMILES: Cc1cc(Cl)cnc1C1(F)CCCN(C(=O)c2cn(C)nc2N)C1]

Prepared as described for 4-[3-(5-chloro-3-methylpyridin-2-yl)-3-methoxypiperidine-1-carbonyl]-1-methyl-1H-pyrazol-3-amine (Example 42) from tert-butyl N-(4-{[3-(5-chloro-3-methylpyridin-2-yl)-3-fluoropiperidin-1-yl]carbonyl}-1-methyl-1H-pyrazol-3-yl)carbamate (Intermediate 57; 0.076 g, 0.168 mmol) using TFA (0.25 ml, 3.24 mmol) in DCM (1 mL) to afford the title compound.

$^1$H NMR (400 MHz, CD$_3$CN) δ ppm 1.68-2.03 (obscured m, 3H) 2.25-2.34 (m, 1H) 2.40-2.53 (m, 3H) 3.04 (br. s., 1H) 3.63 (s, 4H) 4.33-4.83 (m, 4H) 7.47 (s, 1H) 7.67 (s, 1H) 8.38 (s, 1H)

MS ES$^+$:352

3. BIOLOGICAL ASSAY

Prokineticin receptor 1 (PKR1) antagonists may be functionally assessed by measurement of change in intracellular calcium levels induced by Gq mediated increase in inositol triphosphate (IP3) levels. The ability of a compound to block the intracellular release of calcium mediated by PK1 in RBL2H3 cells expressing human PKR1 receptors is determined as a measure of the compound's antagonist activity in vitro.

Approximately 10,000 cells per assay well are seeded in normal culture medium in a 384 well plate (Corning). Twenty-four hours after seeding, the cells are loaded with a calcium sensitive fluorescent dye by replacing the culture medium with assay buffer (1× Hanks buffered saline, 25 mM HEPES, 0.1% w/v fatty acid free BSA (bovine serum albumin), pH 7.4) containing 1 mM probenecid and 1× Calcium 5 Reagent (Molecular Devices). Cells are incubated at 37° C. for 1 hour to allow for dye uptake.

To test for antagonist activity, test compounds at a final concentration range between 0.32 nM-10 µM (diluted in assay buffer) are added to duplicate assay wells and and allowed to incubate for 10 minutes prior to stimulation with PK1. After incubation with test compounds the assay plate is placed in a FLIPR Tetra (Molecular Devices) and PK1 (diluted in assay buffer) is added at the determined EC80 concentration (final). Ligand-dependent changes in intracellular calcium levels are determined by measuring changes in fluorescence of the dye at 525 nM following excitation at 485 nM. Readings from wells that do not contain antagonist enable percentage inhibition curves to be plotted using 4-parameter fit algorithm and IC$_{50}$ values are calculated for each test compound. A minimum of two IC$_{50}$ values determined from independent assays are generated for each compound.

Results

| Compound of Example No. | Mean IC$_{50}$ (µM) | Compound of Example No. | Mean IC$_{50}$ (µM) |
|---|---|---|---|
| 1 | 0.32 | 2 | 0.33 |
| 3 | 9.06 | 4 | 1.22 |
| 5 | 7.46 | 6 | 1.74 |
| 7 | 1.82 | 8 | 1.07 |
| 9 | 1.08 | 10 | 0.39 |
| 11 | 0.94 | 12 | 0.48 |
| 13 | 0.76 | 14 | 0.54 |
| 15 | 0.33 | 16 | 1.44 |
| 17 | 2.59 | 18 | 2.17 |
| 19 | 2.69 | 20 | 1.25 |
| 21 | 5.34 | 22 | 1.73 |
| 23 | 7.41 | 24 | 7.41 |
| 25 | 7.86 | 26 | 3.12 |
| 27 | 0.91 | 28 | 1.04 |
| 29 | 0.48 | 30 | 2.08 |
| 31 | 1.62 | 32 | 1.88 |
| 33 | 0.51 | 34 | 0.47 |
| 35 | 0.29 | 36 | 1.49 |
| 37 | 0.92 | 38 | 1.25 |
| 39 | 0.40 | 40 | 3.41 |
| 41 | 2.39 | 42 | >9 |
| 43 | >5 | | |

Generally, the compounds tested above exhibit IC$_{50}$ values less than 10 µM, with the most potent compounds showing antagonist activity at the prokineticin receptor with IC$_{50}$ values<1 µM. Accordingly, the compounds of the invention are expected to be useful in the prevention or treatment of conditions in which prokineticin receptor modulation is implicated.

The invention claimed is:
1. A compound of formula

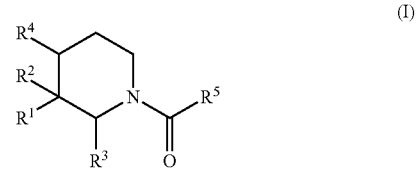

(I)

wherein
R$^1$ represents
(i) 1-(methyl)-1,3-benzodiazol-2-yl,
(ii) 1-(isopropyl)-1,3-benzodiazol-2-yl,
(iii) 1-(methyl)-indol-2-yl,
(iv) 1-(ethyl)-indol-2-yl,
(v) 1-(isopropyl)-indol-2-yl,
(vi) (1-ethyl-5-methyl)-indol-2-yl,
(vii) (1-ethyl-3-methyl)-indol-2-yl,
(viii) (1-ethyl-5-chloro)-indol-2-yl,
(ix) (3-methyl-5-chloro)-pyridin-2-yl, or
(x) (3-trifluoromethyl-5-chloro)-pyridin-2-yl;
R$^2$ represents a hydrogen atom;
R$^3$ represents a hydrogen atom;
R$^4$ represents a hydrogen atom; and
R$^5$ represents
(i) 2-(methylamino)-pyridin-4-yl,
(ii) 2-(dimethylamino)-pyridin-4-yl,
(iii) 6-chloro-pyridazin-4-yl,
(iv) 3-(methylamino)-pyridazin-5-yl,
(v) 3-(dimethylamino)-pyridazin-5-yl,
(vi) 1-(ethyl)-pyrazol-4-yl, or
(vii) (1-methyl-3-amino)-pyrazol-4-yl;
or a pharmaceutically acceptable salt thereof.

2. The compound according to claim 1 being selected from:
N,N-Dimethyl-4-{3-[1-(propan-2-yl)-1H-1,3-benzodiazol-2-yl]piperidin-1-carbonyl}pyridin-2-amine,
(R)—N,N-Dimethyl-4-{3-[1-(propan-2-yl)-1H-1,3-benzodiazol-2-yl]piperidine-1-carbonyl}pyridin-2-amine
(S)—N,N-Dimethyl-4-{3-[1-(propan-2-yl)-1H-1,3-benzodiazol-2-yl]piperidine-1-carbonyl}pyridin-2-amine,
2-[1-(1-Ethyl-1H-pyrazole-4-carbonyl)piperidin-3-yl]-1-(propan-2-yl)-1H-1,3-benzodiazole,
4-}3-(5-Chloro-1-ethyl-1H-indol-2-yl)piperidine-1-carbonyl]-1-methyl-1H-pyrazol-3-amine,
or a pharmaceutically acceptable salts thereof.

3. A process for the preparation of a compound of formula (I) as defined in claim 1 or a pharmaceutically acceptable salt thereof which comprises reacting a compound of formula

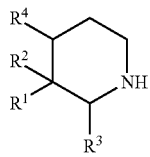
(II)

wherein $R^1$, $R^2$, $R^3$ and $R^4$ are as defined in formula (I) or a salt thereof, with a compound of formula

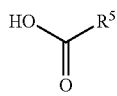
(III)

wherein $R^5$ is as defined in formula (I);
and optionally thereafter carrying out one or more of the following procedures:
   removing any protecting groups
   converting a compound of formula (I) into another compound of formula (I)
   forming a pharmaceutically acceptable salt.

4. A pharmaceutical composition comprising a compound of formula (I) or a pharmaceutically acceptable salt thereof according to claim 1 in association with a pharmaceutically acceptable adjuvant, diluent or carrier, and optionally one or more other therapeutic agents.

5. A method of therapeutically treating an inflammatory bowel disease or irritable bowel syndrome, comprising administering to a subject a compound of formula (I) or a pharmaceutically acceptable salt thereof as claimed in claim 1, wherein the subject is suffering from inflammatory bowel disease or irritable bowel syndrome.

6. A method of therapeutically treating a cognitive disorders or pain, comprising administering to a subject a compound or a pharmaceutically acceptable salt thereof as claimed in claim 1, wherein the subject is suffering from a cognitive disorder or pain.

7. A compound according to claim 1, wherein the compound is a racemic mixture of the R and S enantiomer of N,N-dimethyl-4-{3-[1-(propan-2-yl)-1H-1,3-benzodiazol-2-yl]piperidin-1-carbonyl}pyridin-2-amine or a pharmaceutically acceptable salt thereof.

8. A compound according to claim 1, wherein the compound is a racemic mixture of the R and S enantiomer of N,N-dimethyl-4-{3-[1-(propan-2-yl)-1H-1,3-benzodiazol-2-yl]piperidin-1-carbonyl}pyridin-2-amine.

9. A compound according to claim 1, wherein the compound is the R enantiomer of N,N-dimethyl-4-{3-[1-(propan-2-yl)-1H-1,3-benzodiazol-2-yl]piperidin-1-carbonyl}pyridin-2-amine or a pharmaceutically acceptable salt thereof.

10. A compound according to claim 1, wherein the compound is the S enantiomer of N,N-dimethyl-4-{3-[1-(propan-2-yl)-1H-1,3-benzodiazol-2-yl]piperidin-1-carbonyl}pyridin-2-amine or a pharmaceutically acceptable salt thereof.

11. A compound according to claim 1, wherein the compound is N,N-dimethyl-4-{3-[1-(propan-2-yl)-1H-1,3-benzodiazol-2-yl]piperidin-1-carbonyl}pyridin-2-amine or a pharmaceutically acceptable salt thereof.

12. A compound according to claim 1, wherein the compound is 2-[1-(1-ethyl-1H-pyrazole-4-carbonyl)piperidin-3-yl]-1-(propan-2-yl)-1H-1,3-benzodiazole or a pharmaceutically acceptable salt thereof.

13. A compound according to claim 1, wherein the compound is 4-[3-(5-chloro-1-ethyl-1H-indol-2-yl)piperidine-1-carbonyl]-1-methyl-1H-pyrazol-3-amine or a pharmaceutically acceptable salt thereof.

14. A pharmaceutical composition comprising a compound or a pharmaceutically acceptable salt thereof according to claim 2 in association with a pharmaceutically acceptable adjuvant, diluent or carrier, and optionally one or more other therapeutic agents.

15. A method of therapeutically treating an inflammatory bowel disease or irritable bowel syndrome, comprising administering to a subject a compound or a pharmaceutically acceptable salt thereof as claimed in claim 2, wherein the subject is suffering from inflammatory bowel disease or irritable bowel syndrome.

16. A method of therapeutically treating a cognitive disorder or pain, comprising administering to a subject a compound or a pharmaceutically acceptable salt thereof as claimed in claim 2, wherein the subject is suffering from a cognitive disorder or pain.

* * * * *